(12) United States Patent
McHale et al.

(10) Patent No.: US 10,736,839 B2
(45) Date of Patent: *Aug. 11, 2020

(54) TOPICAL ANTIVIRAL COMPOSITIONS, DELIVERY SYSTEMS, AND METHODS OF USING THE SAME

(71) Applicant: Novan, Inc., Morrisville, NC (US)

(72) Inventors: Kimberly McHale, Hillsborough, NC (US); Ryan Doxey, Raleigh, NC (US); Nathan Stasko, Chapel Hill, NC (US)

(73) Assignee: Novan, Inc., Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/431,214

(22) Filed: Jun. 4, 2019

(65) Prior Publication Data

US 2019/0290577 A1   Sep. 26, 2019

Related U.S. Application Data

(63) Continuation of application No. 15/713,185, filed on Sep. 22, 2017, now Pat. No. 10,322,082, which is a continuation-in-part of application No. 15/324,332, filed as application No. PCT/US2015/039908 on Jul. 10, 2015, now Pat. No. 10,322,081, said application No. 15/713,185 is a continuation of application No. PCT/US2016/012668, filed on Jan. 8, 2016, which is a continuation-in-part of application No. PCT/US2015/039908, filed on Jul. 10, 2015, application No. 16/431,214, which is a continuation of application No. 15/324,332, filed as application No. PCT/US2015/039908 on Jul. 10, 2015, now Pat. No. 10,322,081.

(60) Provisional application No. 62/139,176, filed on Mar. 27, 2015, provisional application No. 62/023,587, filed on Jul. 11, 2014.

(51) Int. Cl.
| | |
|---|---|
| *A61K 9/00* | (2006.01) |
| *A61K 33/00* | (2006.01) |
| *A61K 47/10* | (2017.01) |
| *A61K 47/14* | (2017.01) |
| *A61K 47/02* | (2006.01) |
| *A61K 47/26* | (2006.01) |
| *A61K 47/44* | (2017.01) |
| *A61K 47/24* | (2006.01) |
| *A61K 9/06* | (2006.01) |
| *A61K 31/675* | (2006.01) |

(52) U.S. Cl.
CPC .............. *A61K 9/0014* (2013.01); *A61K 9/06* (2013.01); *A61K 31/675* (2013.01); *A61K 33/00* (2013.01); *A61K 47/02* (2013.01); *A61K 47/10* (2013.01); *A61K 47/14* (2013.01); *A61K 47/24* (2013.01); *A61K 47/26* (2013.01); *A61K 47/44* (2013.01)

(58) Field of Classification Search
CPC .... A61K 9/0014; A61K 47/44; A61K 31/675; A61K 47/14; A61K 47/02; A61K 47/26; A61K 47/24; A61K 33/00; A61K 47/10; A61K 9/06

See application file for complete search history.

(56) References Cited

U.S. PATENT DOCUMENTS

| | | | |
|---|---|---|---|
| 4,822,604 | A | 4/1989 | Knoll et al. |
| 5,840,759 | A | 11/1998 | Mitchell et al. |
| 5,912,008 | A | 6/1999 | Horstmann et al. |
| 5,968,001 | A | 10/1999 | Freeman |
| 5,968,528 | A | 10/1999 | Deckner et al. |
| 6,103,266 | A | 8/2000 | Tapolsky et al. |
| 6,103,275 | A | 8/2000 | Seitz et al. |
| 6,319,913 | B1 | 11/2001 | Mak et al. |
| 6,465,445 | B1 | 10/2002 | Labrie |
| 6,479,058 | B1 | 11/2002 | McCadden |
| 6,565,445 | B1 | 5/2003 | Miller |
| 6,709,681 | B2 | 3/2004 | Benjamin et al. |
| 6,719,997 | B2 | 4/2004 | Hsu et al. |
| 7,048,951 | B1 | 5/2006 | Seitz et al. |
| 7,704,518 | B2 | 4/2010 | Tamarkin et al. |
| 8,114,442 | B2 | 2/2012 | Tucker et al. |
| 8,128,964 | B2 | 3/2012 | Tucker et al. |
| 8,241,650 | B2 | 8/2012 | Peters |
| 8,282,967 | B2 | 10/2012 | Schoenfisch et al. |
| 8,343,945 | B2 | 1/2013 | Tamarkin et al. |
| 8,362,091 | B2 | 1/2013 | Tamarkin et al. |
| 8,399,005 | B2 | 3/2013 | Schoenfisch et al. |
| 8,486,374 | B2 | 7/2013 | Tamarkin et al. |
| 8,591,876 | B2 | 11/2013 | Bauman et al. |
| 8,617,100 | B2 | 12/2013 | Eini et al. |
| 8,636,982 | B2 | 1/2014 | Tamarkin et al. |
| 8,795,635 | B2 | 8/2014 | Tamarkin et al. |
| 8,795,693 | B2 | 8/2014 | Tamarkin et al. |
| 8,900,553 | B2 | 12/2014 | Tamarkin et al. |

(Continued)

FOREIGN PATENT DOCUMENTS

| | | |
|---|---|---|
| CA | 2 594 407 A1 | 8/2006 |
| EP | 1 707 224 A1 | 10/2006 |

(Continued)

OTHER PUBLICATIONS

Al-Sa'Doni et al. "S-Nitrosothiols: a class of nitric oxide-donor drugs" *Clinical Science* 98:507-520 (2000).

Banerjee et al. "Antiviral Effects of Nitric Oxide-Releasing Drug Candidates in Suppressing Productive Infection of HPV-18 in an Organotypic Epithelial Raft Culture Model System" *Poster* (1 page) (Mar. 2, 2017).

Brendle et al. "Pathogenesis of Infection by Human Papillomavirus" *Current Problems in Dermatology* 45:47-57 (2014).

Butsch et al. "Topical treatment with a two-component gel releasing nitric oxide cures C57BL/6 mice from cutaneous leishmaniasis caused by *Leishmania major*" *Experimental Dermatology* 25(11):914-916 (2016).

(Continued)

*Primary Examiner* — Snigdha Maewall
(74) *Attorney, Agent, or Firm* — Myers Bigel, P.A.

(57) ABSTRACT

The present invention relates generally to topical antiviral compositions, delivery systems, and methods of using the same.

20 Claims, 28 Drawing Sheets

(56) References Cited

U.S. PATENT DOCUMENTS

| | | | |
|---|---|---|---|
| 8,956,658 B2 | 2/2015 | Schoenfisch et al. |
| 8,962,029 B2 | 2/2015 | Schoenfisch et al. |
| 9,101,662 B2 | 8/2015 | Tamarkin et al. |
| 9,161,916 B2 | 10/2015 | Tamarkin et al. |
| 9,187,501 B2 | 11/2015 | Schoenfisch et al. |
| 9,265,725 B2 | 2/2016 | Tamarkin et al. |
| 9,320,705 B2 | 4/2016 | Tamarkin et al. |
| 9,381,381 B2 | 7/2016 | Benjamin |
| 9,427,605 B2 | 8/2016 | Peters |
| 2002/0013304 A1 | 1/2002 | Wilson et al. |
| 2002/0028223 A1 | 3/2002 | Vatter et al. |
| 2002/0082221 A1 | 6/2002 | Herrmann et al. |
| 2003/0077243 A1 | 4/2003 | Fitzhugh |
| 2003/0219854 A1 | 11/2003 | Guarna et al. |
| 2004/0037897 A1 | 2/2004 | Benjamin et al. |
| 2004/0105898 A1 | 6/2004 | Benjamin et al. |
| 2004/0202684 A1 | 10/2004 | Djerassi |
| 2005/0037093 A1 | 2/2005 | Benjamin |
| 2005/0038473 A1 | 2/2005 | Tamarkin et al. |
| 2005/0232869 A1 | 10/2005 | Tamarkin et al. |
| 2005/0271596 A1 | 12/2005 | Friedman et al. |
| 2006/0159734 A1 | 7/2006 | Shudo |
| 2006/0269620 A1 | 11/2006 | Morris et al. |
| 2006/0275218 A1 | 12/2006 | Tamarkin et al. |
| 2007/0166255 A1 | 7/2007 | Gupta |
| 2007/0243224 A1 | 10/2007 | Ludwig et al. |
| 2007/0292359 A1 | 12/2007 | Friedman et al. |
| 2007/0292461 A1 | 12/2007 | Tamarkin et al. |
| 2008/0031907 A1 | 2/2008 | Tamarkin et al. |
| 2008/0044444 A1 | 2/2008 | Tamarkin et al. |
| 2008/0063607 A1 | 3/2008 | Tamarkin et al. |
| 2008/0069779 A1 | 3/2008 | Tamarkin et al. |
| 2008/0138296 A1 | 6/2008 | Tamarkin et al. |
| 2008/0152596 A1 | 6/2008 | Friedman et al. |
| 2008/0166303 A1 | 7/2008 | Tamarkin et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0253973 A1 | 10/2008 | Tamarkin et al. |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0068248 A1* | 3/2009 | Waterhouse ......... C07D 255/00 424/423 |
| 2009/0130029 A1 | 5/2009 | Tamarkin et al. |
| 2009/0175799 A1 | 7/2009 | Tamarkin et al. |
| 2009/0214618 A1 | 8/2009 | Schoenfisch et al. |
| 2009/0297634 A1 | 12/2009 | Friedman et al. |
| 2010/0015253 A1 | 1/2010 | Benjamin |
| 2010/0098733 A1 | 4/2010 | Stasko |
| 2010/0129474 A1 | 5/2010 | Benjamin et al. |
| 2010/0215775 A1 | 8/2010 | Schmaus et al. |
| 2010/0221195 A1 | 9/2010 | Tamarkin et al. |
| 2010/0239512 A1 | 9/2010 | Morris et al. |
| 2010/0266510 A1 | 10/2010 | Tamarkin et al. |
| 2010/0310476 A1 | 12/2010 | Tamarkin et al. |
| 2010/0331968 A1 | 12/2010 | Morris et al. |
| 2011/0045037 A1 | 2/2011 | Tamarkin et al. |
| 2011/0052650 A1 | 3/2011 | Morris et al. |
| 2011/0086234 A1 | 4/2011 | Stasko et al. |
| 2011/0097279 A1 | 4/2011 | Tamarkin et al. |
| 2011/0212033 A1 | 9/2011 | Tamarkin et al. |
| 2011/0263526 A1 | 10/2011 | Satyam |
| 2012/0134951 A1 | 5/2012 | Stasko et al. |
| 2012/0136323 A1* | 5/2012 | Stasko ................. A61L 15/225 604/290 |
| 2012/0141384 A1 | 6/2012 | Tamarkin et al. |
| 2012/0156163 A1 | 6/2012 | Bauman et al. |
| 2012/0237453 A1 | 9/2012 | Tamarkin et al. |
| 2013/0164225 A1 | 6/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0310533 A1 | 11/2013 | Bao et al. |
| 2014/0058124 A1 | 2/2014 | Schoenfisch et al. |
| 2014/0134321 A1 | 5/2014 | Stasko et al. |
| 2014/0193502 A1 | 7/2014 | Tamarkin et al. |
| 2014/0242023 A1 | 8/2014 | Doxey et al. |
| 2014/0248219 A1 | 9/2014 | Tamarkin et al. |
| 2014/0255318 A1 | 9/2014 | Stasko et al. |
| 2014/0271494 A1 | 9/2014 | Tamarkin et al. |
| 2015/0017103 A1 | 1/2015 | Tamarkin et al. |
| 2015/0024052 A1 | 1/2015 | Doxey |
| 2015/0025060 A1 | 1/2015 | Tamarkin et al. |
| 2015/0111973 A1 | 4/2015 | Bauman et al. |
| 2015/0118164 A1 | 4/2015 | Tamarkin et al. |
| 2015/0225488 A1 | 8/2015 | Schoenfisch et al. |
| 2016/0008275 A1 | 1/2016 | Doxey et al. |
| 2016/0199295 A1 | 7/2016 | Doxey et al. |
| 2016/0256484 A1 | 9/2016 | Doxey et al. |

FOREIGN PATENT DOCUMENTS

| | | |
|---|---|---|
| EP | 1 861 130 B1 | 9/2008 |
| EP | 1 871 433 B1 | 4/2009 |
| EP | 1 846 058 B1 | 7/2009 |
| EP | 2 119 459 A1 | 11/2009 |
| EP | 2 142 179 A1 | 1/2010 |
| EP | 2 142 181 A1 | 1/2010 |
| EP | 1 917 005 B1 | 9/2010 |
| JP | H07-039748 | 2/1995 |
| JP | 2003-286153 | 10/2003 |
| JP | 2012-197300 | 10/2012 |
| WO | WO 93/10754 A1 | 6/1993 |
| WO | WO 99/44622 A1 | 9/1999 |
| WO | WO 99/63974 A2 | 12/1999 |
| WO | WO 00/02593 A2 | 1/2000 |
| WO | WO 00/33877 A1 | 6/2000 |
| WO | WO 02/41902 A1 | 5/2002 |
| WO | WO 03/095398 A2 | 11/2003 |
| WO | WO 2005/004984 A1 | 1/2005 |
| WO | WO 2006/084910 A2 | 8/2006 |
| WO | WO 2006/084912 A1 | 8/2006 |
| WO | WO 2006/100154 A1 | 9/2006 |
| WO | WO 2007/007208 A2 | 1/2007 |
| WO | WO 2007/023005 A1 | 3/2007 |
| WO | WO 2007/023396 A2 | 3/2007 |
| WO | WO 2007/054818 A2 | 5/2007 |
| WO | WO 2008/032212 A2 | 3/2008 |
| WO | WO 2008/038140 A2 | 4/2008 |
| WO | WO 2008/038147 A2 | 4/2008 |
| WO | WO 2008/110872 A2 | 9/2008 |
| WO | WO 2008/116497 A1 | 10/2008 |
| WO | WO 2008/116925 A1 | 10/2008 |
| WO | WO 2008/152444 A2 | 12/2008 |
| WO | WO 2009/007785 A2 | 1/2009 |
| WO | WO 2009/049208 A1 | 4/2009 |
| WO | WO 2009/056991 A2 | 5/2009 |
| WO | WO 2009/067095 A1 | 5/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/098595 A2 | 8/2009 |
| WO | WO 2010/044875 A2 | 4/2010 |
| WO | WO 2011/022652 A1 | 2/2011 |
| WO | WO 2011/022680 A2 | 2/2011 |
| WO | WO 2011/047013 A1 | 4/2011 |
| WO | WO 2011/073998 A1 | 6/2011 |
| WO | WO 2011/085484 A1 | 7/2011 |
| WO | WO 2012/082976 A1 | 6/2012 |
| WO | WO 2012/100174 A1 | 7/2012 |
| WO | WO 2012/118819 A2 | 9/2012 |
| WO | WO 2012/118829 A2 | 9/2012 |
| WO | WO 2012/153331 A1 | 11/2012 |
| WO | WO 2013/006608 A1 | 1/2013 |
| WO | WO 2013/006613 A1 | 1/2013 |
| WO | WO 2013/029009 A1 | 2/2013 |
| WO | WO 2013/063354 A1 | 5/2013 |
| WO | WO 2013/138073 A1 | 9/2013 |
| WO | WO 2013/138075 A1 | 9/2013 |
| WO | WO 2014/028847 A1 | 2/2014 |

(56) References Cited

FOREIGN PATENT DOCUMENTS

| WO | WO 2014/134502 A1 | 9/2014 |
|---|---|---|
| WO | WO 2015/021382 A2 | 2/2015 |
| WO | WO 2016/010988 A1 | 1/2016 |
| WO | WO 2016/022170 A1 | 2/2016 |
| WO | WO 2016/160089 A1 | 10/2016 |
| WO | WO 2017/011031 A1 | 1/2017 |

OTHER PUBLICATIONS

Cladel et al. "Wounding Prior to Challenge Substantially Improves Infectivity of Cottontail Rabbit Papillomavirus and Allows for Standardization of Infection" *Journal of Virological Methods* 148(1-2):34-39 (2008).

ClinicalTrials.gov "A Trial of the Efficacy and Safety of Topical Nitric Oxide in Patients With Anogenital Warts" clinicaltrials.gov/ct2/show/NCT02015260 (4 pages) (Mar. 27, 2017).

Coggan et al. "Antiviral Efficacy of Nitric Oxide-Releasing Drug Candidates In Vivo Utilizing the Cottontail Rabbit Papillomavirus Model" www.novantherapeutics.com (1 page) (Aug. 28, 2014).

Colasanti et al. "S-Nitrosylation of Viral Proteins: Molecular Bases for Antiviral Effect of Nitric Oxide" *IUBMB Life* 48:25-31 (1999).

Croen, Kenneth D. "Evidence for an Antiviral Effect of Nitric Oxide: Inhibition of Herpes Simplex Virus Type 1 Replication" *Journal of Clinical Investigation* 91:2446-2452 (1993).

De Groote et al. "NO Inhibitions: Antimicrobial Properties of Nitric Oxide" *Clinical Infectious Diseases* 21(Supp. 2):S162-S165 (1995).

De Marco et al. "Oxidative Stress and HPV Carcinogenesis" *Viruses* 5:708-731 (2013).

Extended European Search Report corresponding to related European Patent Application No. 15819451.4 (7 pages) (dated Jan. 8, 2018).

Hrabie et al. "Chemistry of the Nitric Oxide-Releasing Diazeniumdiolate ("Nitrosohydroxylamine") Functional Group and Its Oxygen-Substituted Derivatives" *Chemical Reviews* 102:1135-1154 (2002).

International Search Report and the Written Opinion of the International Searching Authority corresponding to International Patent Application No. PCT/US2015/039908 (12 pages) (dated Oct. 9, 2015).

International Search Report and the Written Opinion of the International Searching Authority corresponding to International Patent Application No. PCT/US2016/012668 (10 pages) (dated Mar. 16, 2016).

Kandavilli et al. "Polymers in Transdermal Drug Delivery Systems" *Pharmaceutical Technology* 26:62-80 (2002).

Karupiah et al. "Inhibition of Viral Replication by Interferon-γ-Induced Nitric Oxide Synthase" *Science* 261(5127):1445-1448 (1993).

McHale et al. "In Vitro and in Vivo Efficacy of Nitric Oxide-Releasing Antiviral Therapeutic Agents" *Antiviral Poster*—www.novantherapeutics.com Abstract # 536 (1 page) (2016).

McHale, Kimberly "In Vitro and in Vivo Efficacy of Nitric Oxide-Releasing Antiviral Therapeutic Agents" Antiviral Presentation—www.novantherapeutics.com (15 pages) (2016).

Novan, Inc. Press Release "Novan to Present Antiviral Preclinical Results of Nitric Oxide-Releasing Drug Candidates for the Treatment of Papillomavirus: Abstract Accepted for Presentation at the 2014 Interscience Conference on Antimicrobial Agents and Chemotherapy Sep. 8, 2014" http://investors.novan.com (2 pages) (Aug. 14, 2014).

Novan, Inc. Press Release "Novan's Nitric Oxide Drug Candidate Inhibits Growth of Papillomavirus in Translational Animal Model: Topical Anti-Viral Could Lead to Treatment for HPV Infections and Help Prevent Cancer" http://investors.novan.com (3 pages) (Sep. 8, 2014).

Novan, Inc. Press Release "Novan to Present Anti-viral Data for Nitric Oxide Product Candidate SB206: Preclinical Data Demonstrating Novel Mechanism of Action for the Treatment of HPV-Associated Warts to be Presented During Society for Investigative Dermatology Annual Meeting" http://investors.novan.com (4 pages) (May 10, 2016).

Novan, Inc. Press Release "Novan Announces Statistically Significant Phase 2 Clinical Trials Results for SB206" http://investors.novan.com (5 pages) (Nov. 29, 2016).

Novan, Inc. Press Release "Novan Announces Presentation of Anti-viral Data at International Papillomavirus Conference: Preclinical Data Showed Significant Inhibition of High-Risk HPV-18 and Reduction of E6 Viral Protein" http://investors.novan.com (4 pages) (Mar. 1, 2017).

Ormerod et al. "The Inflammatory and Cytotoxic Effects of a Nitric Oxide Releasing Cream on Normal Skin" *Journal of Investigative Dermatology* 113(3):392-397 (1999).

Ormerod et al. "An observational prospective study of topical acidified nitrite for killing methicillin-resistant *Staphylococcus aureus* (MRSA) in contaminated wounds" *BMC Research Notes* 4(458):1-7 (2011).

Sangster, James "Octanol-Water Partition Coefficients of Simple Organic Compounds" Journal of Physical and Chemical Reference Data 18(3):1111-1227 (1988).

Saura et al. "An Antiviral Mechanism of Nitric Oxide: Inhibition of a Viral Protease", *Immunity* 10:21-28 (1999).

Stern et al. "Therapy of Human Papillomavirus-Related Disease" *Vaccine* 30(0 5):F71-F82 (2012).

Takhampunya et al. "Antiviral action of nitric oxide on dengue virus type 2 replication" *Journal of General Virology* 87:3003-3011 (2006).

Trying et al. "Results From Phase II Study of Nitric Oxide-Releasing SB206 Once Daily Administration Show Favorable Efficacy and Safety in Genital Warts" *2017 American Academy of Dermatology (AAD) Annual Meeting*, Orlando, Florida Mar. 3-7, 2017 (14 pages).

Wang et al. "Nitric Oxide Donors: Chemical Activities and Biological Applications" *Chemical Reviews* 102:1091-1134 (2002).

Wei et al. "Nitric Oxide Induces Early Viral Transcription Coincident with Increased DNA Damage and Mutation Rates in Human Papillomavirus-Infected Cells" *Cancer Research* 69(11):4878-4884 (2009).

Weller et al. "A randomized trial of acidified nitrite cream in the treatment of tinea pedis" *Journal of the American Academy of Dermatology* 38(4):559-563 (1998).

Extended European Search Report corresponding to European Patent Application No. 20168974.2 (7 pages) (dated May 15, 2020).

Akaike et al. "Nitric oxide and virus infection" Immunology, 101(3):300-308 (2000).

Baldwin et al. "Results of a Phase 2 Efficacy and Safety Study with SB204, an Investigational Topical Nitric Oxide-releasing Drug for the Treatment of Acne Vulgaris" the Journal of Clinical and Aesthetic Dermatology, 9(8):12-18 (2016).

Banerjee et al. "NVN1000, a novel nitric oxide-releasing compound, inhibits HPV-18 virus production by interfering with E6 and E7 oncoprotein functions" Antiviral Research, 170:104559 (2019).

Eichenfield et al. "Results of a Phase 2, Randomized, Vehicle-Controlled Study Evaluating the Efficacy, Tolerability, and Safety of Daily or Twice Daily SB204 for the Treatment of Acne Vulgaris" Journal of Drugs in Dermatology, 15(12):1496-1502 (2016).

Herbert et al. "Efficacy and tolerability of an investigational nitric oxide-releasing topical gel in patients with molluscum contagiosum: a randomized clinical trial" Journal of the American Academy of Dermatology, 82(4):887-894 (2020).

Rahkola et al. "Cervical nitric oxide release and persistence of high-risk human papillomavirus in women" International Journal of Cancer, 128(12):2933-2937 (2011).

Riccio et al. "Nitric Oxide Release: Part I. Macromolecular Scaffolds" Chemical Society Reviews, 41(10):3731-3741 (2012).

Shin et al. "Inorganic/Organic Hybrid Silica Nanoparticles as a Nitric Oxide Delivery Scaffold" Chemistry of Materials, (2008) 20(1):239-249.

Stasko et al. "Nitric Oxide-Releasing Macromolecule Exhibits Broad-Spectrum Antifungal Activity and Utility as a Topical Treatment for Superficial Fungal Infections" Antimicrobial Agents and Chemotherapy, 62(7):e01026-17 (2018).

Sudhesh et al. "Nitric Oxide Releasing Photoresponsive Nanohybrids As Excellent Therapeutic Agent for Cervical Cancer Cell Lines" ACS Applied Materials & Interfaces, 5(17):8263-8266 (2013).

(56) References Cited

OTHER PUBLICATIONS

Tyring et al. "A Phase 2 Controlled Study of SB206, a Topical Nitric Oxide-Releasing Drug for Extragenital Wart Treatment" Journal of Drugs in Dermatology, 17(10):1100-1105 (2018).
Yu et al. "Nitric oxide inhibits the transcription of E6 gene of human papillomavirus" Acta Virologica, 62(4):447-453 (2018).
Mchale et al. "536: in vitro and in vivo efficacy of nitric oxide-releasing antiviral therapeutic agents" Journal of Investigative Dermatology, 136(5):S95 (2016).

* cited by examiner

Group B
1% Nitricil™ NVN1

Group C
1.6% Nitricil™ NVN4

Group E
16.3% Nitricil™ NVN4

Group F
Placebo Ointment

Group H
Cidofovir (0.3% formulated in cremophor; positive control)

Group B
2% Nitricil™ NVN1

Group C
4% Nitricil™ NVN1

TOPICAL ANTIVIRAL COMPOSITIONS, DELIVERY SYSTEMS, AND METHODS OF USING THE SAME

RELATED APPLICATION INFORMATION

This application is a continuation of U.S. application Ser. No. 15/713,185, filed Sep. 22, 2017, which is a continuation-in-part of U.S. application Ser. No. 15/324,332, filed Jan. 6, 2017, which is a 35 U.S.C. § 371 national phase application of International Application Serial No. PCT/US2015/039908, filed Jul. 10, 2015, which claims the benefit of and priority to U.S. Application Ser. No. 62/023,587, filed Jul. 11, 2014, and U.S. Application Ser. No. 62/139,176, filed Mar. 27, 2015, and U.S. application Ser. No. 15/713,185 is a continuation of International Application Serial No. PCT/US2016/012668, filed Jan. 8, 2016, which claims the benefit of and priority to International Application Serial No. PCT/US2015/039908, filed Jul. 10, 2015, which claims the benefit of and priority to U.S. Application Ser. No. 62/023,587, filed Jul. 11, 2014, and U.S. Application Ser. No. 62/139,176, filed Mar. 27, 2015; and this application is a continuation of U.S. application Ser. No. 15/324,332, filed Jan. 6, 2017, which is a 35 U.S.C. § 371 national phase application of International Application Serial No. PCT/US2015/039908, filed Jul. 10, 2015, which claims the benefit of and priority to. U.S. Application Ser. No. 62/023,587, filed Jul. 11, 2014, and U.S. Application Ser. No. 62/139,176, filed Mar. 27, 2015; the disclosure of each of which are incorporated herein by reference in their entirety.

FIELD

The present invention relates generally to topical antiviral compositions, delivery systems, and methods of using the same. Delivery systems may include a topical antiviral composition. Methods of using the topical antiviral compositions and/or delivery systems include methods of treating and/or preventing a viral infection.

BACKGROUND

Viruses cause a number of diseases that can be treated topically. For example, warts can be caused by human papillomavirus and can be treated topically. However, viruses can be difficult to treat since they invade host cells and replicate. In addition, new viral strains have emerged, including antiviral resistant strains.

SUMMARY

It is noted that aspects described with respect to one embodiment may be incorporated in different embodiments although not specifically described relative thereto. Some embodiments are directed to compositions, kits, and/or methods for treating and/or preventing a viral infection. In some embodiments, a method of treating and/or preventing a viral infection in a subject in need thereof is provided.

In some embodiments, the method includes administering a topical composition to the skin of a subject, wherein the topical composition comprises a nitric oxide-releasing active pharmaceutical ingredient in an amount of about 0.5% to about 20% by weight of the composition, thereby treating and/or preventing the viral infection in the subject.

In some embodiments, the method includes administering a topical composition to the skin of a subject, wherein the topical composition comprises a nitric oxide-releasing active pharmaceutical ingredient that releases nitric oxide to the skin of the subject, and wherein the topical composition maintains a real time concentration of nitric oxide of at least about 7 pmol of NO/mg of the composition for at least 1 hour after administration, as measured by real time in vitro release testing, thereby treating and/or preventing the viral infection in the subject.

In some embodiments, the method includes administering a topical composition to the skin of a subject, wherein the topical composition comprises a nitric oxide-releasing active pharmaceutical ingredient that releases nitric oxide to the skin of the subject, and wherein the topical composition maintains a real time concentration of nitric oxide of at least about 104 pmol of NO/cm$^2$ over a time period of at least 1 hour after administration of the composition to the skin of the subject, as measured by real time in vitro release testing, thereby treating and/or preventing a viral infection in the subject.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION

Figure 1:
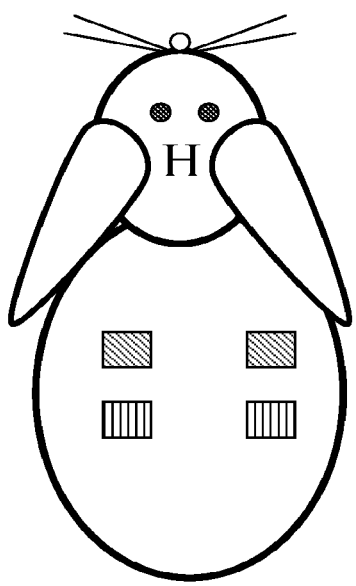
FIG. 1 shows the outline of experimental infections on a rabbit.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value, such as an amount or concentration and the like, is meant to refer to variations of up to ±20% of the specified value, such as, but not limited to, ±10%, ±5%, ±1%, ±0.5%, or even±0.1% of the specified value, as well as the specified value. For example, "about X" where X is the measurable value, is meant to include X as well as variations of ±20%, ±10%, ±5%, ±1%, ±0.5%, or even±0.1% of X. A range provided herein for a measureable value may include any other range and/or individual value therein.

According to some embodiments of the present invention, provided herein are methods of treating and/or preventing a viral infection. A method of treating and/or preventing a viral infection may comprise administering a topical antiviral composition (i.e., a composition of the present invention) to the skin of a subject, thereby treating and/or preventing the viral infection in the subject. In some embodiments, the topical antiviral composition may be administered and/or applied to virally infected skin of the subject. In some embodiments, a method of the present invention may suppress and/or inhibit viral replication of a virus and/or enhance the local immune response of a subject. In some embodiments, administration of the topical antiviral composition to the skin of a subject may provide for topical and/or transdermal delivery of nitric oxide (NO) to the subject. In some embodiments, a method of the present invention may provide for targeted delivery of NO to an area of skin of a subject and/or may provide for local, systemic delivery of NO to the skin and/or surrounding tissues and/or organs of the subject. In some embodiments, a method of administering a composition of the present invention may administer NO to the skin of a subject and/or through the skin to a localized area.

In some embodiments, a drug delivery system may be used to administer a topical antiviral composition of the present invention and/or a nitric oxide (NO)-releasing active pharmaceutical ingredient to the skin of a subject, thereby treating and/or preventing a viral infection in a subject. A drug delivery system of the present invention may comprise a composition of the present invention. Example drug delivery systems may include, but are not limited to, substrates, such as a cloth, dressing, membrane, sponge, ring, suppository, and the like, which may be in contact with a composition of the present invention. In some embodiments, a composition of the present invention and/or a nitric oxide (NO)-releasing active pharmaceutical ingredient may be in and/or on a substrate and/or formed into a substrate (e.g., film, suppository, etc.). The substrate may be placed in contact with the skin of a subject to administer the composition and/or a nitric oxide (NO)-releasing active pharmaceutical ingredient to the skin of a subject.

Exemplary viral infections include, but are not limited to, a viral infection caused by cytomegalovirus (CMV), epstein-barr virus, varicella zoster virus (VZV), vaccinia virus, cowpox virus, monkeypox virus, herpes simplex virus (HSV 1+2), herpes zoster, human herpes virus 6 (HHV-6), human herpes virus 8 (HHV-8), papillomavirus, molluscum contagiosum, orf, variola, and/or coxsackie virus. In some embodiments, the viral infection may be caused by a papillomavirus, such as a human papillomavirus. The human papillomavirus (HPV) may be HPV type 1, 2, 3, 4, 6, 10, 11, 16, 18, 31, 33, 35, 39, 45, 51, 52, 56, 58, and/or 59. In some embodiments, the viral infection may be caused by a herpes simplex virus, such as herpes simplex type 1 and/or herpes simplex type 2. In some embodiments, the viral infection may infect the skin, including mucosa, of the subject. In certain embodiments, the virus may be a human virus.

According to some embodiments of the present invention, provided herein are methods of treating and/or preventing virus-related cutaneous conditions. A method of treating and/or preventing a virus-related cutaneous condition may comprise administering a topical antiviral composition (i.e., a composition of the present invention) to the skin of a subject, thereby treating and/or preventing the virus-related cutaneous condition in the subject. Virus-related cutaneous conditions that may be treated and/or prevented include, but are not limited to, cutaneous conditions associated with bowenoid papulosis, buffalopox, butcher's wart, condylomata acuminate, cowpox, cytomegalovirus, disseminated herpes zoster, eczema herpeticum (Kaposi's varicelliform eruption), eczema vaccinatum, epidermodysplasia verruciformis, erythema infectiosum (fifth disease, slapped cheek disease), farmyard pox, generalized vaccinia, genital herpes (herpes genitalis, herpes progenitalis), Buschke-Löwenstein tumor, hand-foot-and-mouth disease (Coxsackie), Heck's disease (focal epithelial hyperplasia), herpangina, herpes gladiatorum (scrum pox), herpes simplex, herpetic keratoconjunctivitis, herpetic sycosis, herpetic whitlow, human monkeypox, human T-lymphotropic virus 1 infection, human tanapox, intrauterine herpes simplex, Kaposi sarcoma, Lipschtltz ulcer (ulcus vulvae acutum), Milker's nodule, molluscum contagiosum, neonatal herpes simplex, ophthalmic zoster, orf (contagious pustular dermatosis, ecthyma contagiosum, infectious labial dermatitis, sheep pox), oral florid papillomatosis, oral hairy leukoplakia (EBV), orolabial herpes (herpes labialis), progressive vaccinia (vaccinia gangrenosum, vaccinia necrosum), pseudocowpox, recurrent respiratory papillomatosis (laryngeal papillomatosis), sealpox, varicella (chickenpox), variola major (smallpox), verruca plana (flat warts), verruca plantaris (plantar wart), verruca vulgaris (wart), verrucae palmares et plantares, and/or zoster (herpes zoster, shingles).

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom associated with a viral infection is achieved and/or there is a delay in the progression of the viral infection and/or condition. In some embodiments, the severity of a viral infection (e.g., a viral infection caused by human papillomavirus) may be reduced in a subject compared to the severity of the viral infection in the absence of a method of the present invention. In certain embodiments, a method of the present invention treats a viral infection in a subject, such as a viral infection that has affected the skin of the subject. In some embodiments, a method of the present invention may treat a viral infection by eliminating and/or reducing the size and/or appearance of at least one clinical symptom associated with the viral infection (e.g., a benign lesion). In some embodiments, a method of the present invention may treat a viral infection by eliminating at least one clinical symptom associated with the viral infection (e.g., a benign lesion) for a given period of time (e.g., 1, 2, 3, 4, 5, or 6 day(s), or 1, 2, 3, 4, or more weeks, etc.).

In some embodiments, a topical antiviral composition of the present invention is administered in a treatment effective amount. A "treatment effective" amount as used herein is an amount that is sufficient to treat (as defined herein) a subject. Those skilled in the art will appreciate that the therapeutic effects need not be complete or curative, as long as some benefit is provided to the subject. In some embodiments, a treatment effective amount of a topical antiviral composition of the present invention may be administered and may include administering a treatment effective amount of a nitric oxide-releasing active pharmaceutical ingredient. In some embodiments, a treatment effective amount of nitric oxide may be administered and/or applied in a method of the present invention. In some embodiments, a method of the present invention is carried out in a manner such that the administration of a topical antiviral composition comprising a nitric oxide (NO)-releasing active pharmaceutical ingredient (API) does not produce systemic effects (e.g., adverse systemic effects) from the administration of nitric oxide, such as, for example, when the composition, NO-releasing API, and/or NO is administered in a treatment effective amount. In some embodiments, a method of the present invention is carried out in a manner such that the administration of a topical antiviral composition comprising a nitric oxide-releasing active pharmaceutical ingredient produces a local, systemic effect from the administration of nitric oxide, such as, for example, when the composition, NO-releasing API, and/or NO is administered in a treatment effective amount.

The terms "prevent," "preventing" and "prevention" (and grammatical variations thereof) refer to avoidance, reduction and/or delay of the onset of a viral infection and/or a clinical symptom associated therewith in a subject and/or a reduction in the severity of the onset of the viral infection and/or clinical symptom relative to what would occur in the absence of a method of the present invention. The prevention can be complete, e.g., the total absence of the viral infection and/or clinical symptom. The prevention can also be partial, such that the occurrence of the viral infection and/or clinical symptom in the subject and/or the severity of onset is less than what would occur in the absence of a method of the present invention. In certain embodiments, a method of the present invention prevents a viral infection in a subject, such as a viral infection that can affect the skin of the subject.

In some embodiments, a topical antiviral composition of the present invention is administered in a prevention effective amount. A "prevention effective" amount as used herein is an amount that is sufficient to prevent (as defined herein) the viral infection and/or clinical symptom in the subject. Those skilled in the art will appreciate that the level of prevention need not be complete, as long as some benefit is provided to the subject. In some embodiments, a prevention effective amount of a topical antiviral composition of the present invention may be administered and may include administering a prevention effective amount of a nitric oxide-releasing active pharmaceutical ingredient. In some embodiments, a prevention effective amount of nitric oxide may be administered and/or applied in a method of the present invention. In some embodiments, a method of the present invention is carried out in a manner such that the administration of a topical antiviral composition comprising a NO-releasing API does not produce systemic effects (e.g., adverse systemic effects) from the administration of nitric oxide, such as, for example, when the composition, NO-releasing API, and/or NO is administered in a prevention effective amount. In some embodiments, a method of the present invention is carried out in a manner such that the administration of a topical antiviral composition comprising a nitric oxide-releasing active pharmaceutical ingredient produces a local, systemic effect from the administration of nitric oxide, such as, for example, when the composition, NO-releasing API, and/or NO is administered in a prevention effective amount.

The topical antiviral composition may be topically applied to a subject using any method known to those of skill in the art. In some embodiments, the composition may be topically applied to the subject at least 1, 2, 3, or more times per day. In some embodiments, the composition may be topically applied to the subject at least 1, 2, 3, 4, 5, 6, 7, 8, or more times per week and/or month. In certain embodiments, the composition may be topically applied to the subject once daily, twice daily, every other day, every third day, once per week, or twice per week. In some embodiments, the composition may be applied at least once daily for an extended period of time (e.g., a week, month, 2 months, etc.) and/or until the viral infection and/or clinical symptom associated therewith has been treated and/or prevented. In some embodiments, the composition may be applied on an as needed basis.

The present invention finds use in both veterinary and medical applications. Suitable subjects of the present invention include, but are not limited to avians and mammals. The term "avian" as used herein includes, but is not limited to, chickens, ducks, geese, quail, turkeys, pheasants, parrots, parakeets, macaws, cockatiels, canaries, and finches. The term "mammal" as used herein includes, but is not limited to, primates (e.g., simians and humans), non-human primates (e.g., monkeys, baboons, chimpanzees, gorillas), bovines, ovines, caprines, ungulates, porcines, equines, felines, canines, lagomorphs, pinnipeds, rodents (e.g., rats, hamsters, and mice), etc. In some embodiments of the present invention, the subject is a mammal and in certain embodiments the subject is a human. Human subjects include both males and females and subjects of all ages including fetal, neonatal, infant, juvenile, adolescent, adult, and geriatric subjects.

The methods of the present invention may also be carried out on animal subjects, particularly mammalian subjects such as mice, rats, dogs, cats, livestock and horses for veterinary purposes, and/or for drug screening and drug development purposes.

In some embodiments, the subject is "in need of" or "in need thereof" a method of the present invention, for example, the subject is in an at-risk population (e.g. the subject may be at-risk for or more susceptible to a viral infection), the subject has findings typically associated with a viral infection, and/or the subject is suspected to be or to have been exposed to a virus. In some embodiments, a subject in need thereof has a viral infection and/or a clinical sign or symptom associated therewith that may be treated with a method of the present invention. The present invention may be particularly suitable for children, adolescents, adults, and/or geriatric subjects.

A topical antiviral composition of the present invention may be administered and/or applied topically to any portion of a subject's skin, including mucosa. For example, the composition may be topically administered to a subject's hand, finger, foot, toe, arm, leg, trunk, anus, genitals, face, a mucous membrane (including a body cavity), nail, etc. In some embodiments, an antiviral composition of the present invention may be topically administered to at least a portion of a subject's hand, finger, foot, and/or toe. In some embodiments, an antiviral composition of the present invention may be topically administered to at least a portion of a subject's anus, genitals, and/or a mucous membrane (e.g., urethra, cervix, and/or vagina). In some embodiments, an antiviral composition of the present invention may be topically administered to at least a portion of a subject's face, lips, and/or a mucous membrane (e.g., nostrils, mouth, tongue, and/or pharynx).

In some embodiments, a method of the present invention may prevent and/or reduce the appearance and/or size of a benign lesion. Exemplary benign lesions include, but are not limited to, a wart (e.g., common warts (verruca vulgaris), flat warts, plantar warts, subungual and/or periungal warts, anal/genital warts, etc.), oral and/or laryngeal papilloma, anogenital mucosal condylomata, focal epithelial hyperplasic, oral florid papillomatosis, condyloma accuminata, papillomata, molluscum contagiosum, herpetic lesions, orf, and/or cowpow. In some embodiments, the benign lesion may be an external genital wart and/or anal wart (e.g., a perianal wart). In some embodiments, the benign lesion may be a nongenital wart. In some embodiments, the benign lesion may be induced and/or caused by a papillomavirus, such as a human papillomavirus.

A method of the present invention may reduce the appearance and/or size of a benign lesion by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the appearance and/or size of a benign lesion prior to administering of a topical antiviral composition of the present invention. The appearance of the benign lesion may be evaluated visually, such as, but not limited to, by the subject and/or a physician. The size of the benign lesion may be determined using methods known to those of skill in the art. In some embodiments, a method of the present invention may prevent and/or reduce the appearance and/or size of a wart.

In certain embodiments, the subject may see a reduction in the size and/or appearance of a benign lesion within 1, 2, 3, 4, 5, 6, 7, 8, 9, 10, 11, 12, 13, or more day(s) and/or week(s). In some embodiments, the method may reduce the size and/or appearance of a benign lesion in the skin of the subject with 12 weeks or less, in some embodiments, within 8 weeks or less, and in further embodiments, within 4 weeks or less.

A method of the present invention may reduce the number of benign lesions by at least about 5%, 10%0, 15%, 20%, 25%, 30%, 35%, 40%, 45%, 50%, 55%, 60%, 65%, 70%, 75%, 80%, 85%, 90%, 95%, 97% or 100% compared to the number of benign lesions prior to administering of a topical antiviral composition of the present invention. The number of benign lesions may be evaluated visually, such as, but not limited to, by the subject and/or a physician. The number of benign lesions may be determined using methods known to those of skill in the art. In some embodiments, a method of the present invention may prevent and/or reduce the number of warts.

A method of the present invention may decrease the rate of recurrence of a benign lesion in a subject by at least about 5%, 10%0, 15%, 20%, 25%, 30%, 35%, 40%, 45%, 50%, 55%, 60%, 65%, 70%, 75%, 80%, 85%, 90%, 95%, 97% or 100% compared to the rate of recurrence of the same type of benign lesion in the absence of administering of a topical antiviral composition of the present invention. The rate of recurrence may be determined using methods known to those of skill in the art. For example, after a treatment and/or removal of a benign lesion, the number of benign lesions may be visually determined after a given period of time to determine the rate of recurrence. In some embodiments, a method of the present invention may decrease the rate of recurrence of warts in a subject.

The method may comprise topically administering and/or applying a topical antiviral composition to virally infected skin, including mucosa, of the subject that comprises a benign lesion. In some embodiments, the virally infected skin comprises a lesion and the method may further comprise debriding the lesion prior to administering the topical composition to the skin of the subject. In other embodiments, the virally infected skin comprises a lesion and the method may not comprise debriding the lesion prior to administering the topical composition to the skin of the subject. In some embodiments, the lesion may comprise a wart.

In certain embodiments, a method of the present invention may prevent and/or reduce the appearance and/or size of a premalignant lesion and/or a malignant lesion, such as, for example, a tumor. The premalignant lesion and/or malignant lesion may be caused by and/or induced by a viral infection. In some embodiments, a premalignant lesion and/or malignant lesion may be a premalignant and/or malignant cutaneous lesion. In some embodiments, the premalignant lesion and/or malignant lesion may be due to and/or caused by cancer of the cervix, penis, anus, and/or oral cavity. In some embodiments, the premalignant lesion and/or malignant lesion may be induced and/or caused by a papillomavirus, such as a human papillomavirus. In some embodiments, a method of the present invention may prevent and/or reduce the appearance and/or size of cervical intraepithelial neoplasia.

A method of the present invention may reduce the appearance and/or size of a premalignant lesion and/or malignant by at least about 5%, 10%, 15%, 20%, 25%, 30%, 35%, 40%, 45%, 50%, 55%, 60%, 65%, 70%, 75%, 80%, 85%, 90%, 95%, 97% or more compared to the appearance and/or size of a premalignant lesion and/or a malignant lesion prior to administering of a topical antiviral composition of the present invention. The appearance of the premalignant lesion and/or a malignant lesion may be evaluated visually, such as, but not limited to, by the subject and/or a physician. The size of the premalignant lesion and/or a malignant lesion may be determined using methods known to those of skill in the art.

A method of the present invention may reduce the number of premalignant lesions and/or malignant lesions by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the number of premalignant lesions and/or malignant lesions prior to administering of a topical antiviral composition of the present invention. The number of premalignant lesions and/or malignant lesions may be evaluated visually, such as, but not limited to, by the subject and/or a physician. The number of premalignant lesions and/or malignant lesions may be determined using methods known to those of skill in the art.

A method of the present invention may decrease the rate of recurrence of a premalignant lesion and/or malignant lesion in a subject by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the rate of recurrence of the same type of premalignant lesion and/or malignant lesion in the absence of administering of a topical antiviral composition of the present invention. The rate of recurrence may be determined using methods known to those of skill in the art. For example, after a treatment and/or removal of a premalignant lesion and/or malignant lesion, the number of premalignant and/or malignant lesions may be visually determined after a given period of time to determine the rate of recurrence.

In some embodiments, a method of the present invention may administer nitric oxide to the basal layer of a subject's epithelium. A method of the present invention may administer a treatment effective and/or a prevention effective amount of nitric oxide to the basal layer of a subject's epithelium. In some embodiments, nitric oxide may be administered to the basement membrane of a subject's epithelium. The upper epithelial layers of a subject's skin may not need to be debrided, exfoliated, and/or removed in order for the method to administer nitric oxide to the basal layer and/or basement membrane.

In some embodiments, a method of the present invention may administer nitric oxide to the skin of a subject. In some embodiments, a method of the present invention may administer nitric oxide in an amount sufficient to induce apoptosis or other cellular damage in virally infected cells. In some embodiments, a method of the present invention may administer nitric oxide in an amount sufficient to inhibit and/or prevent viral replication. A method of the present invention may reduce viral replication by at least about 10%, 15%, 20%, 25%, 30%, 35%, 40%, 45%, 50%, 55%, 60%, 65%, 70%, 75%, 80%, 85%, 90%, 95%, 98%, 99%, or 100% compared to the rate of replication prior to the method of the present invention.

In some embodiments, a method of the present invention may treat and/or prevent a viral infection in a subject without cytotoxicity to host cells or with reduced cytotoxicity to host cells. The method may treat and/or prevent the viral infection in the subject with reduced host cell cytotoxicity compared to a different method for treating the viral infection, such as, for example, one that does not administer nitric oxide to the skin of a subject or one that uses acidified nitrite. In some embodiments, a method of the present invention may reduce host cell cytotoxicity by at least about 10%, 15%, 20%, 25%, 30%, 35%, 40%, 45%, 50%, 55%, 60%, 65%, 70%, 75%, 80%, 85%, 90%, 95%, 98%, 99%, or 100%0/compared to a different method for treating the viral infection. A method of the present invention may reduce and/or eliminate viral replication with no or minimal host cell cytotoxicity. For example, the method may provide a host cell cytotoxicity of about 50% or less (e.g., about 40%, 30%, 20%, 10%, 5%, or less). Cytotoxicity may be determined using methods known to those of skill in the art, such as, for example, a qualitative reading of hematoxylin & eosin (H&E) slides, a lactate dehydrogenase (LDH) assay and/or a 3-(4, 5-Dimethyl-2-thiazolyl)-2, 5-diphenyl-2H-tetrazolium bromide (MTT) assay. In some embodiments, a method of the present invention may not cause apoptosis. For example, the method may not cause apoptosis in keratinocyte layers of the skin.

In some embodiments, a method of the present invention may cause cells in the skin to normalize. The cells may be those that received a therapeutic and/or prophylactic effect from a method of the present invention. For example, the cells may be those that were administered nitric oxide according to a method of the present invention. The cells may normalize by, for example, returning to a normal growth rate and/or may complete differentiation. In some embodiments, a method of the present invention may reduce the number of actively dividing cells throughout the skin layer and may cause cellular division to be restricted to the basal layer of the skin as is the normal physiologic state. In some embodiments, a method of the present invention may return cells in the skin to a growth rate that does not cause the cells and/or skin to display hyperproliferation, hyperplasia (e.g., benign hyperplasia), and/or dysplasia.

In some embodiments, the virus may cause a thickening in an area of the skin (e.g., the virus may lead to a wart on the skin) and a method of the present invention may reduce the thickness of the skin in this area, such as by at least about 10%, 15%, 20%, 25%, 30%, 35%, 40%, 45%, 50%, or more and/or may return the thickness of the skin in this area to a normal thickness. In some embodiments, the method may reduce the thickness of a thickened area of skin and/or return the thickness of the skin in the thickened area to a thickness of about 20% or less than the normal thickness of the skin. For example, an area of normal skin may have a thickness of 2 mm and a method of present invention may reduce the thickness of thickened skin in this area to a thickness in a range of about 2.4 mm to about 2 mm.

In some embodiments, a method of the present invention may cause cells in the skin to return to a normal G2 and/or S phase. For example, a virus may cause cells to have a prolonged G2 phase following S phase reentry. In some embodiments, a method of the present invention may disrupt and/or interfere with a protein involved in viral replication. For example, a method of the present invention may disrupt and/or interfere with an E7 and/or E6 protein and/or its interactions and/or signaling. In some embodiments, a method of the present invention may activate and/or increase a cellular process that prohibits and/or decreases viral replication.

In some embodiments, a method of the present invention may reduce the amount of viral DNA. For example, a method of the present invention may reduce the amount of viral DNA by at least about 10%, 15%, 20%, 25%, 30%, 35%, 40%, 45%, 50%, 55%, 60%, 65%, 700%, 75%, 80%, 85%, 90%, 95%, 98%, 99%, or 100%0 compared to the amount of viral DNA present prior to the method of the present invention.

According to some embodiments of the present invention, provided is a topical antiviral composition. Exemplary compositions that may be used as a topical antiviral composition include, but are not limited to, those described in International Application No. PCT/US2014/019536, U.S. Provisional Application No. 61/863,541 filed on Aug. 8, 2013, and U.S. Provisional Application No. 61/868,139 filed on Aug. 21, 2013, the disclosures of each of which are incorporated herein by reference in their entirety. The topical antiviral composition may comprise a nitric oxide-releasing active pharmaceutical ingredient (NO-releasing API). In some embodiments, the topical antiviral composition does not comprise acidified nitrite. "Acidified nitrite", as used herein, refers to a nitric oxide releasing composition where the primary mechanism of nitric oxide release is when a nitrite is reduced, in the presence of an acid, to dinitrogen trioxide, which can dissociate into nitric oxide and nitrous oxide. In further embodiments of the present invention, a method of the present invention may administer nitric oxide to the skin of a subject without staining the skin of the subject. For example, a method of the present invention may administer nitric oxide to the skin of a subject without staining the subject's skin yellow, brown, and/or black.

"Nitric oxide releasing active pharmaceutical ingredient" and "NO-releasing API," as used herein, refer to a compound or other composition that provides nitric oxide to the skin of a subject, but is not gaseous nitric oxide. In some embodiments, the NO-releasing API is also not acidified nitrite. In some embodiments, the NO-releasing API includes a nitric oxide-releasing compound, hereinafter referred to as a "NO-releasing compound." An NO-releasing compound includes at least one NO donor, which is a functional group that may release nitric oxide under certain conditions.

Any suitable NO-releasing compound may be used. In some embodiments, the NO-releasing compound includes a small molecule compound that includes an NO donor group. "Small molecule compound" as used herein is defined as a compound having a molecular weight of less than 500 daltons, and includes organic and/or inorganic small molecule compounds. In some embodiments, the NO-releasing compound includes a macromolecule that includes an NO donor group. A "macromolecule" is defined herein as any compound that has a molecular weight of 500 daltons or greater. Any suitable macromolecule may be used, including crosslinked or non-crosslinked polymers, dendrimers, metallic compounds, organometallic compounds, inorganic-based compounds, and other macromolecular scaffolds. In some embodiments, the macromolecule has a nominal diameter ranging from about 0.1 nm to about 100 m and may comprise the aggregation of two or more macromolecules, whereby the macromolecular structure is further modified with an NO donor group.

In some embodiments, the NO-releasing compound includes a diazeniumdiolate functional group as an NO donor. The diazeniumdiolate functional group may produce nitric oxide under certain conditions, such as upon exposure to water. As another example, in some embodiments, the NO-releasing compound includes a nitrosothiol functional group as the NO donor. The NO donor may produce nitric oxide under certain conditions, such as upon exposure to light. Examples of other NO donor groups include nitrosamine, hydroxyl nitrosamine, hydroxyl amine and hydroxyurea. Any suitable combination of NO donors and/or NO-releasing compounds may also be used in a second composition as described herein. Additionally, the NO donor may be incorporated into or onto the small molecule or macromolecule through covalent and/or non-covalent interactions.

An NO-releasing macromolecule may be in the form of an NO-releasing particle, such as those described in U.S. Pat. Nos. 8,282,967, 8,962,029 or U.S. Pat. No. 8,956,658, the disclosures of which are incorporated by reference herein in their entirety. Other non-limiting examples of NO-releasing compounds include NO-releasing zeolites as described in United States Patent Publication Nos. 2006/0269620 or 2010/0331968; NO-releasing metal organic frameworks (MOFs) as described in United States Patent Application Publication Nos. 2010/0239512 or 2011/0052650; NO-releasing multi-donor compounds as described in International Application No. PCT/US2012/052350 entitled "Tunable Nitric Oxide-Releasing Macromolecules Having Multiple Nitric Oxide Donor Structures"; NO-releasing dendrimers or metal structures as described in U.S. Publication No. 2009/0214618; nitric oxide releasing coatings as described in U.S. Publication No. 2011/0086234; and compounds as described in U.S. Publication No. 2010/0098733. The disclosures of each of the references in this paragraph are incorporated herein by reference in their entirety. Additionally, NO-releasing macromolecules may be fabricated as described in International Application No. PCT/US2012/022048 entitled "Temperature Controlled Sol-Gel Co-Condensation" filed Jan. 20, 2012, the disclosure of which is incorporated herein by reference in its entirety.

As an example, in some embodiments of the present invention, a nitric oxide-releasing active pharmaceutical ingredient may include NO-loaded precipitated silica. The NO-loaded precipitated silica may be formed from nitric oxide donor modified silane monomers into a co-condensed siloxane network. In one embodiment of the present invention, the nitric oxide donor may be an N-diazeniumdiolate. In some embodiments of the present invention, the nitric oxide-releasing active pharmaceutical ingredient may comprise, consist essentially of, or consist of a co-condensed siloxane network comprising a diazeniumdiolate (e.g., a N-diazeniumdiolate).

In some embodiments, the nitric oxide donor may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method may be used to create co-condensed siloxane networks and materials more densely functionalized with NO-donors. In some embodiments of the present invention, the nitric oxide-releasing active pharmaceutical ingredient may comprise, consist essentially of, or consist of a co-condensed silica network synthesized from the condensation of a silane mixture comprising an alkoxysilane and at least one aminoalkoxysilane having an amine substituted by a diazeniumdiolate (e.g., a N-diazeniumdiolate).

The co-condensed siloxane network may be silica particles with a uniform size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula Si(OR)4, wherein R is an alkyl group. The R groups may be the same or different. In some embodiments the tetraalkoxysilane is selected as tetramethyl orthosilicate (TMOS) or tetraethyl orthosilicate (TEOS). In some embodiments, the aminoalkoxysilane has the formula: R"—(NH—R')n-Si(OR)3, wherein R is alkyl, R' is alkylene, branched alkylene, or aralkylene, n is 1 or 2, and R" is selected from the group consisting of alkyl, cycloalkyl, aryl, and alkylamine.

In some embodiments, the aminoalkoxysilane may be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl)phenethyltrimethoxysilane (AEMP3); [3-(methylamino)propyl]trimethoxysilane (MAP3); N-butylaminopropyltrimethoxysilane(n-BAP3); t-butylaminopropyltrimethoxysilane(t-BAP3); N-ethylaminoisobutyltrimethoxysilane(EAiB3); N-phenylamino-propyltrimethoxysilane (PAP3); and N-cyclohexylaminopropyltrimethoxysilane (cHAP3).

In some embodiments, the aminoalkoxysilane has the formula: NH [R'—Si(OR)3]2, wherein R is alkyl and R' is alkylene. In some embodiments, the aminoalkoxysilane may be selected from bis(3-triethoxysilylpropyl)amine, bis-[3-(trimethoxysilyl)propyl]amine and bis-[(3-trimethoxysilyl)propyl]ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: R"—N(NONO-X+)—R'—Si(OR)3, wherein R is alkyl, R' is alkylene or aralkylene, R" is alkyl or alkylamine, and X+ is a cation selected from the group consisting of Na+, K+ and Li+.

The composition of the siloxane network, (e.g., amount or the chemical composition of the aminoalkoxysilane) and the nitric oxide charging conditions (e.g., the solvent and base) may be varied to optimize the amount and duration of nitric oxide release. Thus, in some embodiments, the composition of the silica particles may be modified to regulate the half-life of NO release from silica particles.

In another embodiment, the amino group of aminoalkoxysilane is substituted with a diazeniumdiolate, and the aminoalkoxysilane having a formula of R"—N(NONO-X+)—R'—Si(OR)3, wherein: R is alkyl, R' is alkylene or aralkylene, R" is alkyl or alkylamine, and X+ is a cation selected from the group consisting of Na+ and K+.

In certain embodiments, the NO-releasing API may comprise a co-condensed silica network comprising diazeniumdiolated aminoethylaminopropyl trimethoxy silane (AEAP3) and tetra methyl orthosilicate (TMOS) and/or a co-condensed silica network comprising diazeniumdiolated aminoethylaminopropyl trimethoxy silane (AEAP3) and tetraethyl orthosilicate (TEOS). In some embodiments, the NO-releasing API may comprise a co-condensed silica network comprising diazeniumdiolated methylaminopropyl trimethoxysilane (MAP3) and tetra methyl orthosilicate (TMOS) and/or a co-condensed silica network comprising diazeniumdiolated methylaminopropyl trimethoxysilane (MAP3) and tetraethyl orthosilicate (TEOS).

In some embodiments of the invention, the particle size of a NO-releasing API may be in a range of about 20 nm to about 20 µm or any range therein, such as, but not limited to, about 100 nm to about 20 µm or about 1 µm to about 20 µm. The particle size may be tailored to minimize or prevent toxicity and/or penetration through the epidermis (or compromised dermis) and into the blood vessels. In particular embodiments, the particle size is distributed around a mean particle size of less than 20 µm, or any range therein, and the size may allow the particle to enter a follicle. In some embodiments, a NO-releasing API may have a particle size that is distributed around a mean particle size of about 20, 19, 18, 17, 16, 15, 14, 13, 12, 11, 10, 9, 8, 7, 6, 5, 4, 3, 2, or 1 µm. In further embodiments, a NO-releasing API may have a particle size that is distributed around a mean particle size of less than 10 µm, or any range therein, such as, but not limited to about 2 µm to about 10 µm or about 4 µm to about 8 µm. In other embodiments, the particle size may be distributed around a mean particle size of greater than 20 µm, or any range therein, and the size may prevent the particle from entering the follicle. In still further embodiments, a mixture of particles with mean particle sizes distributed around two or more mean particle sizes may be provided. A NO-releasing API may be micronized (e.g., ball and/or jet milled). Methods for providing a desired particle size and/or micronization include, but are not limited to, those described in U.S. Patent Application Publication No. 2013/0310533, which is incorporated herein by reference in its entirety.

In some embodiments, a NO-releasing API may be present in a topical antiviral composition in an amount of about 0.5% to about 25% by weight of the composition. For example, in some embodiments, a NO-releasing API may be present in a composition of the present invention in an amount of about 0.5% to about 20%, about 0.5% to about 5%, about 1% to about 20%, about 1% to about 10%, about 1% to about 8%, about 1% to about 20%, about 5% to about 15%, or about 2% to about 6% by weight of the composition. In certain embodiments, a nitric oxide-releasing active pharmaceutical ingredient may be present in a composition of the present invention in an amount of about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight of the composition.

A composition of the present invention may comprise a NO-releasing API and may store and/or release nitric oxide in an amount of about 0.05% to about 10% by weight of the composition, such as, but not limited to, about 0.15% to about 2%, about 0.15% to about 1%, about 0.3% to about 1.2%, about 0.15% to about 6%, about 1% to about 10%, about 3% to about 6%, or about 1% to about 5% by weight of the composition. In certain embodiments, a composition of the present invention may comprise a nitric oxide-releasing active pharmaceutical and may store and/or release nitric oxide in an amount of about 0.15%, 0.3%, 0.6%, 0.9%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, or 10% by weight of the composition. The amount of nitric oxide released may be determined using real time in vitro release testing. In some embodiments, nitric oxide release may be determined using a chemiluminescent nitric oxide analyzer.

A composition of the present invention may provide and/or allow for an extended period of time of NO release. In some embodiments, a composition of the present invention may provide and/or allow for a continuous release of NO for about 1 hour or more, such as, but not limited to, about 2, 3, 4, 5, 6, 7, 8, 9, 10, 11, 12, or more hours after administration of the topical composition to a subject. In some embodiments, the composition may provide for a continuous release of NO for at least about 1, 2, 3, 4, or 5 hours after administration of the topical composition to a subject.

In some embodiments, a topical antiviral composition of the present invention may provide a release rate of about 1 to about 5,000 pmol of NO/mg/s of the composition at a defined time period after administration of the composition to a subject. All releases of nitric oxide described herein, including those described with regard to a time period after administration to a subject, are referenced with respect to real time in vitro release testing. The in vivo release of nitric oxide (i.e., the nitric oxide release when the topical antiviral composition of the present invention is applied to a subject) may vary with the subject to which the topical antiviral composition is applied. In some embodiments, the in vivo release of nitric oxide may vary depending on the particular embodiment of topical antiviral composition. However, it is believed that differences in the in vitro release of topical antiviral compositions according to the present invention will be reflected in the release of nitric oxide when the topical composition is applied to a subject. Accordingly, for clarity, unless specifically stated that the nitric oxide release is when applied to a subject, references to nitric oxide release with regard to embodiments of the topical antiviral compositions of the present invention will be with reference to the in vitro release of the composition. Time point zero or the initial time point of the in vitro release testing may be correlated to the time of administration to a subject with all subsequent real-time points corresponding to a certain time after administration.

In some embodiments, the composition may release about 1 to about 10, about 1 to about 100, about 100 to about 1000, about 1000 to about 4,000, or about 2,500 to about 5,000 pmol of NO/mg of the composition at 1 hour, 45, 30, 15, 5, 4, 3, 2, or 1 minute(s) as measured by in vitro release. In some embodiments, the composition may release, on average, about 1, 2, 3, 4, 5, 6, 7, 8, 9, 10, 20, 30, 40, 50, 100, or more pmol of NO/mg of the composition at 24, 20, 15, 10, 5, 4, 3, 2 or 1 hours as measured by in vitro release.

In some embodiments, the NO release values provided herein may include the amount of variation typically associated with the manufacture of the NO-releasing API. For example, variation in the NO release may be seen between samples in the same lot and/or different lots. In some embodiments, variation in the NO release between samples in the same lot and/or different lots may be in a range of ±about 0% to about 15% and this variation may be included in the NO release values described herein. In some embodiments, variation in the NO release between samples in the same lot and/or different lots may be in a range of about 10% to about 15% and this variation may be included in the NO release values described herein.

In some embodiments, the composition may release about 1 to about 10, about 1 to about 100, about 100 to about 1000, about 1000 to about 4,000, or about 2,500 to about 5,000 pmol of NO/mg of the composition at 0.5, 1 hour, 45, 30, 15, 5, 4, 3, 2, or 1 minute(s) after administration of the composition to a subject. In some embodiments, the composition may release, on average, about 1, 2, 3, 4, 5, 6, 7, 8, 9, 10, 20, 30, 40, 50, 100, or more pmol of NO/mg of the composition at 24, 20, 15, 10, 5, 4, 3, 2 or 1 hours after administration of the composition to a subject.

A topical antiviral composition of the present invention may provide for a continuous release of NO for at least about 0.5, 1, 2, 3, 4, 5, 6, 7, 8, 9, 10, or more hours as measured by in vitro release, and the composition may have a release of NO during the continuous release that, on average, is in a range of about 1 to about 500 pmol of NO/mg of the composition, such as, but not limited to, about 10 to about 50, about 50 to about 200, about 100 to about 500, about 300 to about 500, about 1 to about 10, or about 1 to about 3 pmol of NO/mg of the composition.

A topical antiviral composition of the present invention may provide for a continuous release of NO for at least about 0.5, 1, 2, 3, 4, 5, 6, 7, 8, 9, 10, or more hours after administration of the composition to a subject, and the composition may have a release of NO during the continuous release that, on average, is in a range of about 1 to about 500 pmol of NO/mg of the composition, such as, but not limited to, about 10 to about 50, about 50 to about 200, about 100 to about 500, about 300 to about 500, about 1 to about 10, or about 1 to about 3 pmol of NO/mg of the composition.

In some embodiments of the present invention, a topical antiviral composition of the present invention maintains a real time concentration of NO of greater than 5 pmol of NO/mg for a period of at least 4 hours, a real time concentration of NO of greater than 6 pmol of NO/mg for a period of at least 2 hours, and/or a real time concentration of NO of greater than 7 pmol of NO/mg for a period of at least 1 hour as measured by in vitro release. In some embodiments, a topical antiviral composition of the present invention may maintain a real time concentration of NO of at least about 5 pmol of NO/mg or more (e.g., 10, 20, 30, 40, 50, 100, 150, 200, 250, 500, 1000, 2000 pmol of NO/mg of the composition or more) for a period of at least 1 hour or more (e.g., 1, 1.5, 2, 2.5, 3, 3.5, 4, 4.5, 5, 5.5, 6, 6.5, 7, 7.5, 8, 8.5 hours or more) as measured by in vitro release.

In particular embodiments of the present invention, a topical antiviral composition of the present invention maintains a real time concentration of NO in a range of about 5 pmol to about 4000 pmol of NO/mg for a period of at least 4 hours, a real time concentration of NO in a range of about 6 to about 4000 pmol of NO/mg for a period of at least 2 hours, and/or a real time concentration of NO in a range of about 7 to about 4000 pmol of NO/mg for a period of at least 1 hour as measured by in vitro release.

In some embodiments of the present invention, a topical antiviral composition of the present invention maintains a real time concentration of NO of greater than 74 pmol of $NO/cm^2$ for a period of at least 4 hours, a real time concentration of NO of greater than 89 pmol of $NO/cm^2$ for a period of at least 2 hours, and/or a real time concentration of NO of greater than 104 pmol of $NO/cm^2$ for a period of at least 1 hour as measured by in vitro release. In particular embodiments of the present invention, a topical antiviral composition of the present invention maintains a real time concentration of NO in a range of about 74 pmol of $NO/cm^2$ to about 59,520 pmol of $NO/cm^2$ for a period of at least 4 hours, a real time concentration of NO in a range of about 89 to about 59,520 pmol of $NO/cm^2$ for a period of at least 2 hours, and/or a real time concentration of NO in a range of about 104 to 59,520 pmol of NO/cm² for a period of at least 1 hour as measured by in vitro release.

In some embodiments, a topical antiviral composition of the present invention may provide for a cumulative release of NO of at least about 10 nmol of NO/mg of the composition at 24 hours or less (e.g., 24, 20, 15, 10, 5, 4, 2, or 1 hours) after administration of the composition to a subject. The topical antiviral composition may have a cumulative release of NO in a range of about 10 to about 50, about 10 to about 100, about 100 to about 1000, about 250 to about 750, about 500 to about 750, about 50 to about 1000, about 100 to about 1500, about 200 to about 1000, about 100 to about 500, or about 500 to about 1000 nmol of NO/mg of the composition at 24 hours or less after administration of the composition to a subject.

In some embodiments, a topical antiviral composition of the present invention provides a cumulative release of NO in a range of about 180 nmol of NO/mg to about 1000 nmol of NO/mg in 24 hours after administration of the composition to a subject. In some embodiments of the present invention, a topical antiviral composition of the present invention provides a cumulative release of NO of greater than 180 nmol of NO/mg in 24 hours after administration of the composition to a subject while maintaining a real time concentration of NO of greater than 5 pmol of NO/mg for a period of at least 4 hours as measured by in vitro release. In some embodiments, a topical antiviral composition of the present invention provides a cumulative release of NO in a range of about 90 nmol of NO/mg to about 450 nmol of NO/mg in 4 hours after administration of the composition to a subject.

In some embodiments, a topical antiviral composition of the present invention releases half of the NO released from the composition in about 9 minutes or longer based on a total NO release determined at 24 hours measured by in vitro release. In some embodiments, the topical antiviral composition may release half of the NO released from the composition in about 10, 20, 30, 40, 50, or 60 minutes, or 2, 3, 4, 5, 6, 7, or 8 hours or more based on a total NO release determined at 24 hours measured by in vitro release. In some embodiments, a topical antiviral composition of the present invention releases half of the NO released from the composition in a range of about 9 minutes to about 8 hours based on a total NO release determined at 24 hours measured by in vitro release.

In some embodiments, a topical antiviral composition of the present invention provides a maximum concentration (Cmax) of NO released of greater than 160 pmol of NO/mg based on a total NO release determined at 24 hours measured by in vitro release. In some embodiments, the topical antiviral composition of the present invention may provide a Cmax of NO released of about 175, 200, 300, 400, 500, 600, 700, 800, 900, 1000, 1500, 2000, 2500, 3000, 3500 pmol of NO/mg or more based on a total NO release determined at 24 hours measured by in vitro release. In some embodiments, a topical antiviral composition of the present invention provides a maximum concentration of NO released in a range of about 160 pmol of NO/mg to about 3500 pmol of NO/mg. In some embodiments, a topical antiviral composition of the present invention provides a maximum concentration of NO released of greater than 160 pmol of NO/mg and releases half of the NO released from the composition in about 9 minutes or longer based on a total NO release determined at 24 hours measured by in vitro release.

In particular embodiments of the present invention, a topical antiviral composition provides a maximum concentration of NO released of at least about 3000 pmol of NO/mg, releases at least about 900 nmol of NO/mg in 24 hours, and/or releases half of the NO release in about 9 minutes based on a total NO release determined at 24 hours measured by in vitro release. In particular embodiments of the present invention, a topical antiviral composition provides a maximum concentration of NO released of at least about 13 pmol of NO/mg, releases at least about 300 nmol of NO/mg in 24 hours and/or releases half of the NO release in about 420 minutes based on a total NO release determined at 24 hours measured by in vitro release. In further embodiments, a topical antiviral composition has a real time concentration of NO of at least 5 pmol of NO/mg at 4 hours as measured by in vitro release. In particular embodiments of the present invention, a topical antiviral composition provides a maximum concentration of NO released in a range of about 12 pmol of NO/mg to about 3200 pmol of NO/mg, a real time concentration of NO of at least 5 pmol of NO/mg at 4 hours, releases NO in a range of about 300 nmol of NO/mg to about 1000 nmol of NO/mg in 24 hours, and/or releases half of the NO release in a range of about 9 minutes to about 420 minutes based on a total NO release determined at 24 hours measured by in vitro release.

In some embodiments, a topical antiviral composition of the present invention may maintain a real time concentration of NO of at least about 70 pmol of NO/cm² or more (e.g., 75, 100, 150, 200, 250, 500, 1000, 2000, 3000, 4000, 5000, 6000, 7000 pmol of NO/cm² or more) for a period of at least 0.5 hours or more (e.g., 1, 1.5, 2, 2.5, 3, 3.5, 4, 4.5, 5, 5.5, 6, 6.5, 7, 7.5, 8, 8.5 hours or more) after administration of the composition to a subject, as measured by in vitro release. In some embodiments of the present invention, a topical antiviral composition of the present invention maintains a real time concentration of NO of greater than 70 pmol of NO/cm² for a period of at least 4 hours as measured by in vitro release.

In some embodiments, a topical antiviral composition of the present invention may provide for a cumulative release of NO of at least about 4500 nmol of NO/cm² (e.g., 5000, 6000, 7000, 8000, 9000, 10000, 11000, 12000, 13000, 14000 nmol of NO/cm² or more) at 24 hours or less (e.g., 24, 20, 15, 10, 5, 4, 2, or 1 hours) after administration of the composition to a subject. In some embodiments, a topical antiviral composition of the present invention provides a cumulative release of NO in a range of about 4500 nmol of NO/cm² to about 14000 nmol of NO/cm² in 24 hours after administration of the composition to a subject. In some embodiments of the present invention, a topical antiviral composition of the present invention provides a cumulative release of NO of greater than 4500 nmol of NO/cm² in 24 hours after administration of the composition to a subject while maintaining a real time concentration of NO of greater than 70 pmol of NO/cm² for a period of at least 4 hours as measured by in vitro release. In some embodiments, a topical antiviral composition of the present invention provides a cumulative release of NO in a range of about 1300 nmol of NO/cm² to about 14000 nmol of NO/cm² in 4 hours after administration of the composition to a subject.

In some embodiments, a topical antiviral composition of the present invention may have a real time concentration of NO of at least about 10 pmol of NO/cm² or more (e.g., 20, 30, 40, 50, 60, 70, 80, 90, 100, 200, 300, 400, 500, 600, 700, 800, 900, 1000 pmol of NO/cm² or more) at 0.5 hours or more (e.g., 1, 1.5, 2, 2.5, 3, 3.5, 4, 4.5, 5, 5.5, 6, 6.5, 7, 7.5, 8, 8.5 hours or more) after administration of the composition to a subject. In some embodiments, a topical antiviral composition of the present invention provides a real time concentration of NO of at least 100 pmol of NO/cm$^2$ at 0.5 hours, at least 50 pmol of NO/cm$^2$ at 1 hour, at least 40 pmol of NO/cm$^2$ at 2 hours, at least 25 pmol of NO/cm$^2$ at 3 hours, and/or at least 20 pmol of NO/cm$^2$ at 4 hours, each as measured by in vitro release. In some embodiments, a topical antiviral composition of the present invention provides a real time concentration of NO of at least 130 pmol of NO/cm$^2$ at 0.5 hours, at least 115 pmol of NO/cm$^2$ at 1 hour, at least 90 pmol of NO/cm$^2$ at 2 hours, at least 90 pmol of NO/cm$^2$ at 3 hours, and/or at least 80 pmol of NO/cm$^2$ at 4 hours, each as measured by in vitro release.

In some embodiments, a topical antiviral composition of the present invention provides a real time concentration of NO of at least 800 pmol of NO/cm$^2$ at 0.5 hours, at least 500 pmol of NO/cm$^2$ at 1 hour, at least 200 pmol of NO/cm$^2$ at 2 hours, at least 100 pmol of NO/cm$^2$ at 3 hours, and/or at least 50 pmol of NO/cm$^2$ at 4 hours, each as measured by in vitro release.

In some embodiments, a topical antiviral composition of the present invention provides a maximum concentration of NO released of greater than 2400 pmol of NO/cm$^2$. In some embodiments, a topical antiviral composition of the present invention provides a maximum concentration of NO released in a range of about 2400 pmol of NO/cm$^2$ to about 47000 pmol of NO/cm$^2$. In some embodiments, a topical antiviral composition of the present invention provides a maximum concentration of NO released of greater than 2400 pmol of NO/cm$^2$ and releases half of the NO released from the composition in 10 minutes or longer based on a total NO release determined at 24 hours measured by in vitro release.

In particular embodiments of the present invention, a topical antiviral composition provides a maximum concentration of NO released of at least about 47000 pmol of NO/cm$^2$, releases at least about 13000 nmol of NO/cm$^2$ in 24 hours and/or releases half of the NO release in about 9 minutes based on a total NO release determined at 24 hours measured by in vitro release. In particular embodiments of the present invention, a topical antiviral composition provides a maximum concentration of NO released of at least about 190 pmol of NO/cm$^2$, releases at least about 4600 nmol of NO/cm$^2$ in 24 hours and/or releases half of the NO in about 420 minutes based on a total NO release determined at 24 hours measured by in vitro release. In further embodiments, a topical antiviral composition has a real time concentration of NO of at least 70 pmol of NO/cm$^2$ at 4 hours as measured by in vitro release. In particular embodiments of the present invention, a topical antiviral composition provides a maximum concentration of NO release in a range of about 190 pmol of NO/cm$^2$ to about 47000 pmol of NO/cm$^2$, a real time concentration of NO of at least 70 pmol of NO/cm$^2$ at 4 hours, releases NO in a range of about 4600 nmol of NO/cm$^2$ to about 47000 nmol of NO/cm$^2$ in 24 hours and/or releases half of the NO release in a range of about 9 minutes to about 420 minutes based on a total NO release determined at 24 hours measured by in vitro release.

The efficacy of the nitric oxide releasing product may be related, not only to the amount of nitric oxide release, but to the rate at which it is released. Accordingly, products with an average release rate over about 5 minutes and in some embodiments, 4.7 minutes, of 600 nmol NO/mg hour$^{0.5}$ or greater, 900 nmol NO/mg hour$^{0.5}$ or greater, 2500 nmol NO/mg hour$^{0.5}$ or greater, 4000 nmol NO/mg hour$^{0.5}$ or greater or 4500 nmol NO/mg hour$^{0.5}$ or greater measured by in vitro release may be utilized according to certain embodiments of the present invention.

The pH of a composition of the present invention may be in a range of about 3 to about 11. In some embodiments, the pH of the composition may be in a range of about 3 to about 5, about 3.5 to about 4.5, about 5 to about 7, about 5.5 to about 6.5, about 3.5 to about 6.5, about 6 to about 10, about 6 to about 7, about 7 to about 10, about 7 to about 9, about 7 to about 8, about 7.5 to about 8, or about 8 to about 9. In certain embodiments, the pH of the composition may be about 3, 4, 5, 6, 7, 8, 9, 10, or 11. The pH of the composition may be determined prior to administration to a subject and/or may be determined once applied to the skin of the subject. In some embodiments, where a composition of the present invention comprises two or more parts and/or phases, the pH may be determined upon combination and/or mixing of the two or more parts and/or phases prior to and/or after administration to the skin of the subject. In certain embodiments, the pH of the composition is measured prior to administration to the skin of the subject, but after combining all parts and/or phases of the composition.

The pH may be measured using known methods. The pH of a composition of the present invention may be determined once a steady state pH is achieved prior to and/or after administration and/or after combination of a first part and second part of the composition. Alternatively or in addition, the pH of a composition of the present invention may be determined after a defined period of time, such as, but not limited to, after about 5, 10, 15, 20, 25, 30, 35, 40, 45, 50, 55, 60 minutes or more. In some embodiments, the pH of a composition of the present invention may be measured in vitro. Alternatively or in addition, the pH of a composition of the present invention may be measured after administration to a subject, such as, for example, a skin surface pH may be measured after administration of a composition of the present invention to the skin of a subject.

A composition of the present invention may comprise at least two parts. The at least two parts may be combined prior to, during, and/or after administration to a subject to form an antiviral composition of the present invention. In some embodiments, a composition of the present invention comprises a first part comprising a first composition and a second part comprising a second composition.

In some embodiments, the first and second composition may be combined by mixing, stirring, blending, dispersing, milling, homogenizing, applying to same area or region, and the like. In some embodiments, the first and second composition may be mixed and/or blended prior to, during, and/or after administration to the skin of a subject. In some embodiments, the first composition and second composition may be combined by applying one or more layers of the second composition onto a subject and then applying one or more layers of the first composition onto a subject or vice versa to form a topical antiviral composition of the present invention.

The second composition may comprise a NO-releasing API. In some embodiments, a composition of the present invention may comprise a first part comprising a first composition that may be in the form of a hydrogel. "Hydrogel," as used herein, refers to a hydrophilic gel comprising a gel matrix and water. In some embodiments, the first composition may comprise at least one polyhydric alcohol, at least one viscosity increasing agent, and water. In some embodiments, the first composition may comprise at least one polyhydric alcohol, at least one viscosity increasing agent, water, at least one additional solvent (i.e., at least one solvent in addition to water), a buffer and/or buffering agent, an emollient, and optionally a preservative.

Exemplary polyhydric alcohols that may be present in a first composition include, but are not limited to, glycerol, propylene glycol, polyethylene glycol, polypropylene glycol, triethylene glycol, neopental glycols, butylene glycol, polyethylene glycol, sorbitol, arabitol, erythritol, HSH, isomalt, lactitol maltitol, mannitol, xylitol, threitol, ribitol, galactitol, fucitol, iditol, inositol, volemitol, and any combination thereof. In some embodiments, the first composition comprises glycerol, such as, but not limited to, anhydrous glycerol.

A polyhydric alcohol may be present in a first composition in an amount of about 1% to about 30% by weight of the first composition or any range and/or individual value therein, such as, but not limited to, about 1% to about 20%, about 1% to about 10%, about 5% to about 10%, or about 5% to about 15% by weight of the first composition. In certain embodiments, a polyhydric alcohol may be present in the first composition in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% by weight of the first composition or any range and/or individual value therein.

Exemplary viscosity increasing agents that may be present in a first composition include, but are not limited to, a carboxypolymethylene; a polyacrylic polymer such as polyacrylic acid, a polyacrylate polymer, a cross-linked polyacrylate polymer, a cross-linked polyacrylic acid, and mixtures thereof; a cellulose ether such as hydroxyalkyl cellulose polymers such as hydroxypropyl methyl cellulose (HPMC), hydroxypropyl cellulose, hyrdoxyethyl cellulose, methyl cellulose, carboxymethyl cellulose, and mixtures thereof; a methacrylate; a polyvinylpyrollidone; cross-linked polyvinyl pyrrolidone; polyvinylpyrrolidone-vinyl acetate copolymer; polyvinylalcohol; polyethylene oxide; polyethylene glycol; polyvinylalkyl ether-maleic acid copolymer; a carboxy vinyl polymer, a polysaccharide; a gum such as sodium alginate, carrageenan, xantham gum, gum acacia, arabic gum, guar gum, pullulan, agar, chitin, chitosan, pectin, karaya gum, zein, hordein, gliadin, locust bean gum, tragacantha, and mixtures thereof; a protein such as collagen, whey protein isolate, casein, milk protein, soy protein, gelatin, and mixtures thereof; a starch such as maltodextrin, amylose, high amylose starch, corn starch, potato starch, rice starch, tapioca starch, pea starch, sweet potato starch, barley starch, wheat starch, waxy corn starch, modified starch (e.g. hydroxypropylated high amylose starch), dextrin, levan, elsinan, gluten, and mixtures thereof; bentonite; calcium stearate; ceratonia; colloidal silicon dioxide; dextrin; hypromellose; polycarbophil; kaolin; saponite; sorbitan esters; sucrose; sesame oil; tragacanth; potassium alginate; povidone; sodium starch glycolate; phospholipids; and any combination thereof.

In some embodiments, a first composition may comprise a carboxypolymethylene, such as, but not limited to, those commercially available from Lubrizol Corporation of Wickliffe, Ohio under the trade name Carbopol®. Exemplary Carbopol® polymers that may be present in a first composition include, but are not limited to, Carbopol® 974P NF polymer, such as Type A, Type B and/or Type C Homopolymers; Carbopol® Ultrez 10, 20, 21 NF polymer, Carbopol® 971P NF polymer, Carbopol® 980 Homopolymer Type C polymer, Carbopol® 980 NF polymer, Carpobol® 980P polymer, Carbopol® ETD 2020 NF polymer, Carbopol® 71 G NF polymer, Carbopol® 981P NF polymer, Carbopol® 970P NF polymer, Carbopol® 981P NF polymer, Carbopol® 5984P NF polymer, Carbopol® 934P NF polymer, Carbopol® 940P NF polymer, Carbopol® 941P NF polymer, Carbopol® 13242 NF polymer, Carbopol® AA-1 USP NF polymer, Carbopol® TR1 NF polymer, Carbopol® TR2 NF polymer, Lubrizol Aqua CC polymer and SF-2 polymer, and any combination thereof.

In some embodiments, a first composition may comprise a cellulose, such as, but not limited to, a carboxymethyl cellulose or a salt thereof. In some embodiments, a first composition may comprise carboxymethyl cellulose sodium.

In some embodiments, a viscosity increasing agent present in the first composition may be a polymer comprising acidic groups, such as, but not limited to, carboxylic acid groups. The acidic groups of the polymer may be partially neutralized in the first composition. In certain embodiments, a viscosity increasing agent present in the first composition may be a carboxypolymethylene. In some embodiments, a carboxypolymethylene present in the first composition may be partially neutralized. A first composition may comprise a carboxypolymethylene and have a pH of about 3 to about 7, about 3.5 to about 6.5, about 3.5 to about 6, or about 4 to about 6. In certain embodiments, a first composition may comprise a carboxypolymethylene and have a pH of about 3, 3.5, 4, 4.5, 5, 5.5, 6, 6.5, or 7.

A viscosity increasing agent may be present in the first composition. In some embodiments, a composition of the present invention may comprise at least two viscosity increasing agents that may be the same or different. In some embodiments, a first viscosity increasing agent may be present in a first composition in an amount of about 0.01% to about 5% by weight of the first composition or any range and/or individual value therein, such as, but not limited to, about 0.05% to about 3%, about 1% to about 5%, about 1% to about 3%, or about 0.1% to about 1.5% by weight of the first composition. In certain embodiments, a first viscosity increasing agent is present in a first composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, or 5% by weight of the first composition or any range and/or individual value therein.

Water may be present in the first composition in an amount of about 55% to about 99% by weight of the first composition or any range and/or individual value therein, such as, but not limited to, about 55% to about 75%, about 60% to about 95%, about 60% to about 80%, about 75% to about 95%, or about 80% to about 90% by weight of the first composition. In certain embodiments, water is present in a first composition in an amount of about 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 790%, 80%, 81%, 82%, 83%, 84%, 85%, 86%, 87%, 88%, 89%, 90%, 91%, 92%, 93%, 94%, 95%, 96%, 97%, 98%, or 99% by weight of the first composition or any range and/or individual value therein.

In some embodiments, one or more solvent(s) in addition to water may be present in a first composition. For example, the first composition may comprise water and 1, 2, 3, 4, 5, or more additional solvents. The one or more solvent(s) in addition to water may each be present in the first composition in an amount of about 0.5% to about 20% by weight of the first composition or any range and/or individual value therein, such as, but not limited to, about 1% to about 15%, about 1% to about 10%0, about 5% to about 15%, or about 1% to about 5% by weight of the first composition. In certain embodiments, the one or more solvent(s) in addition to water may each be present in a first composition in an amount of about 0.5%, 0.75%, 1%, 2%, 3%, 4%, 5%, 6%, 7%, 8%, 9%, 10%, 11%, 12%, 13%, 14%, 15%, 16%, 17%, 18%, 19%, or 20% by weight of the first composition or any range and/or individual value therein. Example solvents in addition to water that may be present in a first composition include, but are not limited to an alcohol, such as, for example, isopropyl alcohol or ethanol.

In some embodiments, a first composition comprises, consists essentially of or consists of at least one polyhydric alcohol present in an amount of about 1% to about 30% by weight of the first composition, at least one viscosity increasing agent present in an amount of about 0.1% to about 5% by weight of the first composition, and water present in an amount of about 55% to about 99% by weight of the first composition. In certain embodiments, the viscosity increasing agent may be a carboxypolymethylene or a carboxymethyl cellulose or a salt thereof. The first composition may be a hydrogel.

A first composition may comprise a preservative. A preservative may be present in a first composition in an amount of about 0.01% to about 1% by weight of the first composition or any range and/or individual value therein, such as, but not limited to, about 0.01% to about 0.1%, about 0.05% to about 0.5%, about 0.05% to about 1%, or about 0.1% to about 1% by weight of the first composition. In certain embodiments, a preservative is present in a first composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% by weight of the first composition or any range and/or individual value therein. Exemplary preservatives that may be present in a first composition include, but are not limited to, sorbic acid, benzoic acid, methyl-paraben, propyl-paraben, methylchloroisothiazolinone, metholisothiazolinone, diazolidinyl urea, chlorobutanol, triclosan, benzethonium chloride, p-hydroxybenzoate, chlorhexidine, digluconate, hexadecyltrimethyl ammonium bromide, alcohols, benzalkonium chloride, boric acid, bronopol, butylparaben, butylene calcium acetate, calcium chloride, calcium lactate, carbon dioxide, cationic, and bentonite, cetrimide, cetylpyridinium chloride, chlorhexidine, chlorobutanol, chlorocresol, chloroxylenol, citric acid monohydrate, cresol, dimethyl ether, ethylparaben, glycerin, hexetidine, imidurea, isopropyl alcohol, lactic acid, monothioglycerol, pentetic acid, phenol, phenoxyethanol, phenylethyl alcohol, phenylmercuric acetate, phenylmercuric borate, phenylmercuric nitrate, potassium benzoate, potassium metabisulfite, potassium sorbate, propionic acid, propyl gallate, propylene glycol, sodium acetate, sodium benzoate, sodium borate, sodium lactate, sodium sulfite, sodium propionate, sodium metabisulfite, xylitol, sulphur dioxide, carbon dioxide, and any combination thereof.

A first composition may comprise a neutralizing agent. A neutralizing agent may be present in a first composition in an amount sufficient to provide a desired pH, such as, but not limited to, a pH of about 3 to about 11, or any range and/or individual value therein, such as, but not limited to, about 3 to about 8, about 4 to about 7, or about 6 to about 7, or about 6 to 11.

In some embodiments, a neutralizing agent may be present in a first composition in an amount sufficient to provide the first composition with a pH in a range of about 3 to about 8.

In certain embodiments, a neutralizing agent may be present in a first composition in an amount sufficient to provide a composition of the present invention with a desired pH upon combination of the first composition and a second part (e.g., a second composition) and/or upon administration of the first composition and/or the composition comprising the first composition and the second part to the skin of a subject. A neutralizing agent may be present in a first composition in an amount sufficient to provide a composition of the present invention (e.g., a composition comprising the first composition and a second composition) with a desired pH, such as, but not limited to, a pH of about 3 to about 11, or any range and/or individual value therein.

In some embodiments, a neutralizing agent adjusts the pH of the first composition and/or composition of the present invention. In certain embodiments of the present invention, a neutralizing agent is present in a first composition in an amount sufficient for the first composition to have a pH of about 3, 3.5, 4, 4.5, 5, 5.5, 6, 6.5, 7, 7.5, or 8 or any range and/or individual value therein. In some embodiments of the present invention, a neutralizing agent is present in a composition of the present invention in an amount sufficient for the composition to have a pH of about 3, 3.5, 4, 4.5, 5, 5.5, 6, 6.5, 7, 7.5, 8, 8.5, 9, 9.5, 10, 10.5, or 11, or any range and/or individual value therein.

Exemplary neutralizing agents that may be present in a first composition include, but are not limited to, bases such as sodium hydroxide, potassium hydroxide, and mixtures thereof; acids such as hydrochloric acid, citric acid, lactic acid, glycolic acid, acetic acid, and mixtures thereof; sodium carbonate; trolamine; tromethamine; aminomethyl propanol; triisopropanolamine; aminomethyl propanol; tetrahydroxypropyl ethylenediamine; tetrasodium EDTA; suttocide A; and any combination thereof.

A neutralizing agent may be present in a first composition in an amount of about 0.01% to about 1% by weight of the first composition or any range and/or individual value therein, such as, but not limited to, about 0.01% to about 0.1%, about 0.05% to about 1%, or about 0.1% to about 1% by weight of the first composition. In certain embodiments, a neutralizing agent may be present in a first composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% by weight of the first composition or any range and/or individual value therein.

A first composition may be unbuffered or buffered. In some embodiments, a first composition may be unbuffered. In other embodiments, a first composition may be buffered. Exemplary buffers that may be present in a first composition include, but are not limited to, acetic acid/acetate buffers; hydrochloric acid/citrate buffers; citro-phosphate buffers; phosphate buffers; citric acid/citrate buffers; lactic acid buffers; tartaric acid buffers; malic acid buffers; glycine/HCl buffers; saline buffers such as phosphate buffered saline (PBS), Tris-buffered saline (TBS), Tris-HCl, NaCl, Tween buffered saline (TNT), phosphate buffered saline, Triton X-100 (PBT) and mixtures thereof; cacodylate buffers; barbital buffers; tris buffers; and any combination thereof. In some embodiments, the buffer may be a phosphate buffer, such as, for example, a potassium phosphate dibasic and/or potassium phosphate monobasic buffer.

In some embodiments, a buffer may be present in a first composition in an amount of about 0.01% to about 20% by weight of the first composition or any range and/or individual value therein, such as, but not limited to, about 0.1% to about 20%, about 1% to about 15%, about 5% to about 20%, about 10% to about 20%, or about 1% to about 10% by weight of the first composition. In certain embodiments, a buffer is present in a first composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%°, 11%, 12%, 13%, 14%, 15%, 16%, 17%, 18%, 19%, or 20% by weight of the first composition or any range and/or individual value therein.

In certain embodiments, a first composition may comprise a buffering agent. Exemplary buffering agents include, but are not limited to, citric acid, acetic acid, lactic acid, boric acid, succinic acid, malic acid, and any combination thereof. A buffering agent may be present in a first composition in an amount of about 0.01% to about 4% by weight of the first composition or any range and/or individual value therein, such as, but not limited to, about 0.01% to about 0.1%, about 0.05% to about 1%, about 0.1% to about 0.5%, about 1% to about 3%, or about 0.1% to about 2% by weight of the first composition. In certain embodiments, a buffering agent is present in a first composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.25%, 1.5%, 1.75%, 2%, 2.25%, 2.5%, 2.75%, 3%, 3.25%, 3.5%, 3.75%, or 4% by weight of the first composition or any range and/or individual value therein.

In some embodiments, a buffer and/or buffering agent is present in a first composition in an amount sufficient for the first composition to have a pH of about 3 to about 8 or any range and/or individual value therein, such as, but not limited to, about 3 to about 6, about 3 to about 5, about 4 to about 7, about 5 to about 7, or about 6 to about 7. In certain embodiments of the present invention, a buffer and/or buffering agent may be present in a first composition in an amount sufficient for the first composition to have a pH of about 3, 3.5, 4, 4.5, 5, 5.5, 6, 6.5, 7, 7.5, or 8, or any range and/or individual value therein.

In some embodiments, a buffer and/or buffering agent may be present in a first composition in an amount sufficient to provide a desired pH for a composition of the present invention comprising the first composition and a second part (e.g., a second composition). For example, a composition of the present invention may comprise a second composition and a first composition comprising a buffer and/or buffering agent, wherein the buffer and/or buffering agent is present in an amount sufficient to provide the composition with a pH of about 3 to about 11, such as, but not limited to, about 3 to about 8, about 7 to about 11, about 8 to about 10, about 3 to about 5, about 4 to about 7, about 5 to about 7, or about 6 to about 7.

In certain embodiments of the present invention, a buffer and/or buffering agent may be present in a first composition in an amount sufficient for the composition of the present invention to have a pH of about 3, 3.5, 4, 4.5, 5, 5.5, 6, 6.5, 7, 7.5, 8, 8.5, 9, 9.5, 10, 10.5, or 11, or any range and/or individual value therein. In some embodiments, the buffer and/or buffering agent may be present in a first composition in an amount sufficient to provide a desired pH upon administration of a composition of the present invention comprising the first composition and a second part to the skin of a subject.

In some embodiments, a buffer, buffering agent, and/or neutralizing agent may be present in a first composition in an amount sufficient to provide a composition of the present invention and/or a first composition with a desired pH.

In some embodiments, an emollient may be provided in a first composition, such as, but not limited to, silicones, such as, for example, cyclomethicone, dimethicone, simethicone, C26-28 alkyl dimethicone, C26-28 alkyl methicone, polyphenylsisquioxane, trimethylsiloxysilicate and crosspolymers of cyclopentasiloxane and dimethicone/vinyltrimethylsiloxysilicate, and blends thereof. In some embodiments, a first composition may comprise cyclomethicone. An emollient may be present in the first composition in an amount of about 0.5% to about 10% by weight of the first composition or any range and/or individual value therein, such as, but not limited to, about 1% to about 5%, about 0.5% to about 4%, about 1% to about 10%, or about 2% to about 8% by weight of the first composition. In certain embodiments, an emollient may be present in the first composition in an amount of about 0.5%, 1%, 2%, 3%, 4%, 5%, 6%, 7%, 8%, 9%, or 10% by weight of the first composition or any range and/or individual value therein.

In certain embodiments, a first composition may comprise at least one polyhydric alcohol present in an amount of about 1% to about 30% by weight of the first composition, at least one viscosity increasing agent present in an amount of about 0.01% to about 5% by weight of the first composition, water present in an amount of about 55% to about 99% by weight of the first composition, and optionally at least one preservative in an amount of about 0.01% to about 1% by weight of the first composition. The first composition may have a pH in a range of about 3 to about 8, about 3 to about 6, or about 6 to about 8 and may be buffered. The first composition may be a hydrogel.

In some embodiments, a first composition may comprise, consist essentially of, or consist of a polyhydric alcohol in an amount of about 1% to about 15% by weight of the first composition, a viscosity increasing agent in an amount of about 0.1% to about 5% by weight of the first composition, water in an amount of about 55% to about 85% by weight of the first composition, optionally a buffer in an amount of about 0.1% to about 20%, optionally a buffering agent in an amount of about 0.001% to about 2% by weight of the first composition, optionally a preservative in an amount of about 0.001% to about 1% by weight of the first composition, and optionally a neutralizing agent in an amount of about 0.001% to about 1% by weight of the first composition. The first composition may have a pH in a range of about 3 to about 5 or about 5 to about 7. In certain embodiments, the viscosity increasing agent present in the first composition may be a carboxypolymethylene or carboxymethyl cellulose or a salt thereof. In some embodiments, the first composition may be cosmetically elegant. The first composition may be a hydrogel.

In some embodiments, a first composition may comprise, consist essentially of, or consist of a polyhydric alcohol in an amount of about 1% to about 30% by weight of the first composition, a viscosity increasing agent in an amount of about 0.01% to about 5% by weight of the first composition, water in an amount of about 55% to about 99% by weight of the first composition, optionally at least one additional solvent (e.g., an alcohol) in an amount of about 0.5% to about 20% by weight of the first composition, optionally an emollient in an amount of about 0.5% to about 10% by weight of the first composition, optionally a buffer in an amount of about 0.01% to about 20% by weight of the first composition, optionally a preservative in an amount of about 0.001% to about 1% by weight of the first composition, and optionally a neutralizing agent in an amount of about 0.001% to about 1% by weight of the first composition. In some embodiments, the at least one solvent comprises an alcohol and the first composition comprises a buffer, an emollient, and a preservative. The first composition may have a pH in a range of about 3 to about 5 or about 5 to about 7. In some embodiments, the pH may be about 4.5. In certain embodiments, the viscosity increasing agent present in the first composition may be carboxymethylcellulose or a salt thereof. In some embodiments, the first composition may be cosmetically elegant. The first composition may be a hydrogel.

A composition of the present invention may comprise an active pharmaceutical ingredient (API). Except for acidified nitrite, any suitable API or combinations of APIs may be included in a composition of the present invention. In some embodiments, the API may be any suitable API that provides the nitric oxide release as described herein. Examples of APIs include, but are not limited to, antimicrobial agents, anti-acne agents, anti-inflammatory agents, analgesic agents, anesthetic agents, antihistamine agents, antiseptic agents, immunosuppressants, antihemorrhagic agents, vasodilators, wound healing agents, anti-biofilm agents, and any combination thereof. Exemplary APIs include, but are not limited to, those described in International Application Publication No. WO 2013/006608, which is incorporated herein by reference in its entirety.

In some embodiments, a first composition may not comprise an API. In certain embodiments, a first composition does not contain a nitric oxide (NO) releasing API. In some embodiments, a first composition may comprise at least one API, but the first composition may not comprise an NO-releasing API. In some embodiments, a first composition comprises an API (e.g., a moisture sensitive API) and a second composition comprises a second API, such as, for example, a NO-releasing API.

In some embodiments, the second composition may be an anhydrous composition. "Anhydrous," as used herein, means that there is no direct addition of water to the second composition when it is being prepared. However, those skilled in the art will recognize that water may be physically and/or chemically absorbed by the second composition and/or by one or more ingredients in the second composition at any time during the preparation, storage, and/or use of the second composition (i.e., indirect addition of water to the second composition). In some embodiments, the term "anhydrous" means that the second composition has a water content of less than 5% by weight of the second composition or any range and/or individual value therein. A second composition may have a water content of less than 5, 4.5, 4, 3.5, 3, 2.5, 2, 1.5, 1, or 0.5%, or any range therein, by weight of the second composition. Water content may be measured by methods known to those of skill in the art, such as, but not limited to, Karl Fischer titration. In certain embodiments, upon contact with a second composition, a composition of the present invention adds water to the second composition and/or the second composition absorbs water from a composition of the present invention.

Exemplary second compositions that may be used and/or placed in contact with a first composition include, but are not limited to, those described in International Application Publication No. WO 2013/006608, which is incorporated herein by reference in its entirety. An exemplary second composition that may be used and/or placed in contact with a first composition to form a topical antiviral composition of the present invention may comprise an anhydrous composition comprising at least one viscosity increasing agent present in the second composition in an amount of about 0.1% to about 30% by weight of the second composition, at least one organic solvent present in the second composition in an amount of about 50% to about 90 by weight of the second composition, and at least one humectant present in the second composition in an amount of about 2% to about 20% by weight of the second composition. The second composition may further comprise at least one water repelling agent, also referred to as a water repellant.

Exemplary viscosity increasing agents for the second composition include, but are not limited to, co-polymers of carboxymethylcellulose and acrylic acid, N-vinylpyrrolidone, polyalkylene glycols (e.g., poly(ethylene glycol)), polyalkylene oxides (e.g., polyethylene oxide), polyvinyl alcohols, polyvinylpyrrolidone, polysiloxanes, poly(vinyl acetates), cellulose, derivatized celluloses, alginates, copolymers thereof and blends thereof. A specific example of a viscosity agent for the second composition is a hydroxypropylcellulose, such as Klucel® hydroxypropylcellulose (e.g., Klucele M F Pharm grade). A viscosity increasing agent may be present in the second composition in an amount of about 0.1% to about 30% by weight of the second composition or any range and/or individual value therein, such as, but not limited to, about 0.5% to about 20%, about 0.1% to about 2%, about 0.5% to about 5%, about 1% to about 10%, or about 1% to about 5% by weight of the second composition. In certain embodiments, a viscosity increasing agent may be present in the second composition in an amount of about 0.1%, 0.25%, 0.5%, 0.75%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% by weight of the second composition or any range and/or individual value therein.

Exemplary organic solvents for the second composition include, but are not limited to, acetone, methyl alcohol, ethanol, isopropanol, butyl alcohol, ethyl acetate, dimethyl isosorbide, propylene glycol, glycerol, ethylene glycol, polyethylene glycol, diethylene glycol monoethyl ether or mixtures thereof. In some embodiments of the present invention, the organic solvent in the second composition may be ethanol and/or isopropyl alcohol. An organic solvent may be present in the second composition in an amount of about 40% to about 90% by weight of the second composition or any range and/or individual value therein, such as, but not limited to, about 40% to about 80%, about 50% to about 70%, about 50% to about 80%, about 60% to about 90%, about 70% to about 90%, or about 75% to about 85% by weight of the second composition. In certain embodiments, an organic solvent may be present in the second composition in an amount of about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% by weight of the second composition or any range and/or individual value therein.

Exemplary humectants for the second composition include, but are not limited to, glycols, such as diethylene glycol monoethyl ether; glycerols; sugar polyols, such as sorbitol, xylitol and maltitol; polyols such as polydextroses; *quillaia*, urea, and blends thereof. In some embodiments, the humectant in the second composition may comprise an alkylene glycol, such as, for example, hexylene glycol. A humectant may be present in the second composition in an amount of about 2% to about 20% by weight of the second composition or any range and/or individual value therein, such as, but not limited to, about 2% to about 15%, about 5% to about 15%, or about 15% to about 20% by weight of the second composition. In certain embodiments, a humectant may be present in the second composition in an amount of about 2%, 3%, 4%, 5%, 6%, 7%, 8%, 9%, 10%, 11%, 12%, 13%, 14%, 15%, 16%, 17%, 18%, 19%, or 20% by weight of the second composition or any range and/or individual value therein.

Exemplary water repellants for the second composition include, but are not limited to, silicones, such as cyclomethicone, dimethicone, simethicone, C26-28 alkyl dimethicone, C26-28 alkyl methicone, polyphenylsisquioxane, trimethylsiloxysilicate and crosspolymers of cyclopentasiloxane and dimethicone/vinyltrimethylsiloxysilicate, and blends thereof. In some embodiments, a second composition may comprise cyclomethicone. A water repellant may be present in the second composition in an amount of about 0.5% to about 15% by weight of the second composition or any range and/or individual value therein, such as, but not limited to, about 0.5% to about 10%, about 1% to about 5%, or about 2% to about 5% by weight of the second composition. In certain embodiments, a water repellant may be present in the second composition in an amount of about 0.5%, 1%, 2%, 3%, 4%, 5%, 6%, 7%, 8%, 9%0, 10%, 11%, 12%, 13%, 14%, or 15% by weight of the second composition or any range and/or individual value therein.

Accordingly, a topical antiviral composition of the present invention may comprise at least one polyhydric alcohol, a first viscosity increasing agent, water, a second viscosity increasing agent, at least one organic solvent, at least one humectant, optionally at least one solvent in addition to water, optionally an emollient, optionally a water repelling agent, optionally at least one preservative, and optionally at least one buffering agent and/or buffer. The composition may be buffered to a pH of about 3 to about 11, such as, but not limited to, about 6 to about 10, about 7 to about 10, or about 7 to about 9. In some embodiments, the composition may have a pH of 7 or greater, 7.5 or greater, or 9.5 or greater. In certain embodiments, the composition may comprise at least one API, such as, but not limited to, a nitric oxide-releasing active pharmaceutical ingredient. In some embodiments, the NO-releasing API may be a diazeniumdiolate modified macromolecule.

A topical antiviral composition of the present invention may comprise a first composition and a second composition as described herein. As those of skill in the art will recognize, the amount or concentration of individual components in a composition of the present invention may vary depending on the amount of the first composition and second composition present in the composition (e.g., the ratio of the first composition and second composition present in the composition). In some embodiments, the ratio of a first composition of the present invention to a second composition in a composition of the present invention may be about 5:1 or less, in further embodiments, about 4:1 or less, about 3:1 or less, about 2:1 or less, about 1:1 or less, about 0.5:1 or less, or about 0.2:1 or less. In particular embodiments, the ratio may be about 3:1. In further embodiments, the ratio may be about 1:1.

In some embodiments, a composition of the present invention may comprise, consist essentially of, or consist of a polyhydric alcohol in an amount of about 0.5% to about 10% by weight of the composition, a first viscosity increasing agent in an amount of about 0.01% to about 3% by weight of the composition, water in an amount of about 30% to about 50% by weight of the composition, at least one solvent in addition to water in an amount of about 0.5% to about 10% by weight of the composition, an emollient in an amount of about 0.5% to about 5% by weight of the composition, a buffer in an amount of about 0.01% to about 10% by weight of the composition, a second viscosity increasing agent in an amount of about 0.01% to about 10% by weight of the composition, an organic solvent in an amount of about 20% to about 45% by weight of the composition, a humectant in an amount of about 2% to about 10% by weight of the composition, a water repelling agent in an amount of about 0.1% to about 10% by weight of the composition, an NO-releasing API in an amount of about 0.5% to about 25% by weight of the composition, optionally a buffering agent in an amount of about 0.001% to about 1% by weight of the composition, optionally a preservative in an amount of about 0.001% to about 1% by weight of the composition, and optionally a neutralizing agent. The buffer, buffering agent and/ot neutralizing agent may be present in an amount sufficient to provide the first part of the composition with a pH of about 3 to about 8. The composition may have a pH of less than about 11, such as, but not limited to, less than about 9.5, less than about 7, or less than about 6. In some embodiments, the composition may have a pH of about 4.5. The first and second viscosity increasing agents may be the same and/or different. In certain embodiments, the first viscosity increasing agent may be a carboxypolymethylene and the second viscosity increasing agent may be a cellulose, such as, but not limited to, hydroxypropyl cellulose. In some embodiments, the first viscosity increasing agent may be a carboxymethyl cellulose or a salt thereof and the second viscosity increasing agent may be a cellulose, such as, but not limited to, hydroxypropyl cellulose. In some embodiments, the composition may be cosmetically elegant.

In some embodiments, a composition of the present invention may comprise, consist essentially of, or consist of a polyhydric alcohol in an amount of about 1% to about 7% by weight of the composition, a first viscosity increasing agent in an amount of about 0.1% to about 3% by weight of the composition, water in an amount of about 25% to about 40% by weight of the composition, at least one solvent in addition to water in an amount of about 0.5% to about 10% by weight of the composition, an emollient in an amount of about 0.5% to about 5% by weight of the composition, a buffer in an amount of about 0.01% to about 10% by weight of the composition, a second viscosity increasing agent in an amount of about 0.1% to about 2% by weight of the composition, an organic solvent in an amount of about 20% to about 45% by weight of the composition, a humectant in an amount of about 2% to about 7% by weight of the composition, a water repelling agent in an amount of about 1% to about 5% by weight of the composition, an NO-releasing API in an amount of about 5% to about 20% by weight of the composition, optionally a buffering agent in an amount of about 0.01% to about 0.2% by weight of the composition, optionally a preservative in an amount of about 0.01% to about 0.3% by weight of the composition, and optionally a neutralizing agent. The buffer, buffering agent, and/or neutralizing agent may be present in an amount sufficient to provide the first part of the composition with a pH of about 4 or about 6. The composition may have a pH of less than about 11, such as, but not limited to, less than about 9.5, less than about 7, or less than about 6. In some embodiments, the composition may have a pH of about 4.5. The first and second viscosity increasing agents may be the same and/or different. In certain embodiments, the first viscosity increasing agent may be a carboxypolymethylene and the second viscosity increasing agent may be a cellulose, such as, but not limited to, hydroxypropyl cellulose. In some embodiments, the first viscosity increasing agent may be a carboxymethyl cellulose or a salt thereof and the second viscosity increasing agent may be a cellulose, such as, but not limited to, hydroxypropyl cellulose. In some embodiments, the composition may be cosmetically elegant. In certain embodiments, the composition may comprise a composition as set forth in Table 2 and/or Table 13.

In some embodiments, a composition of the present invention may comprise, consist essentially of, or consist of a polyhydric alcohol in an amount of about 1% to about 15% by weight of the composition, a first viscosity increasing agent in an amount of about 0.01% to about 2.5% by weight of the composition, water in an amount of about 25% to about 50% by weight of the composition, at least one additional solvent (e.g., an alcohol) in an amount of about 0.5% to about 10% by weight of the composition, an emollient in an amount of about 0.5% to about 5% by weight of the composition, a buffer in an amount of about 0.01% to about 10% by weight of the composition, a second viscosity increasing agent in an amount of about 0.01% to about 10% by weight of the composition, an organic solvent in an amount of about 20% to about 50% by weight of the composition, a humectant in an amount of about 2% to about 10% by weight of the composition, a water repelling agent in an amount of about 0.1% to about 10% by weight of the composition, an NO-releasing API in an amount of about 0.5% to about 25% by weight of the composition, and optionally a preservative in an amount of about 0.001% to about 0.5% by weight of the first composition.

A composition of the present invention may comprise at least two different viscosity increasing agents. One viscosity increasing agent may be present in the first part of a composition of the present invention and the other viscosity increasing agent may be present in the second part of the composition. In some embodiments, a composition of the present invention comprises a carboxypolymethylene and a cellulose, such as, but not limited to, hydroxypropyl cellulose. Carboxypolymethylene may be present in a first composition of the present invention and the cellulose may be present in a second composition, which may be combined to form a composition of the present invention. In some embodiments, a composition of the present invention comprises carboxymethyl cellulose sodium and a second cellulose, such as, but not limited to, hydroxypropyl cellulose. Carboxymethyl cellulose sodium may be present in a first composition of the present invention and the second cellulose may be present in a second composition, which may be combined to form a composition of the present invention. A composition of the present invention comprising at least two different viscosity increasing agents may provide a cosmetically elegant composition comprising an API, such as, but not limited to, a particulate API and/or an insoluble API (e.g., an aqueous and/or moisture insoluble API, such as, for example, benzoyl peroxide).

A composition of the present invention may comprise an API, carboxymethyl cellulose sodium, and hydroxypropyl cellulose, and may be a cosmetically elegant composition. The composition may not be gritty and/or may have a reduced grittiness compared to the API in the absence of a composition of the present invention. The composition may not be tacky (i.e., sticky) and/or may have a reduced tackiness (i.e., stickiness) compared to the API in the absence of a composition of the present invention. The composition may have a reduced and/or increased stiffness (i.e., hardness) and/or may have an increased homogeneity compared to the API in the absence of a composition of the present invention. In some embodiments, a composition of the present invention may comprise an API and may be a cosmetically elegant, homogeneous composition.

According to embodiments of the present invention, a topical antiviral composition may be provided in a kit. In some embodiments, a kit of the present invention may comprise a first composition and a second composition as described herein that may be combined to form the topical antiviral composition. The kit may separately store the first and second composition. The kit may be configured to mix the two compositions upon dispensing and/or for application to the skin of a subject in a desired ratio (e.g., 1:1, 2:1, etc.).

The present invention is explained in greater detail in the following non-limiting Examples.

EXAMPLES

Example 1

Groups of rabbits received anti-viral treatments at various doses as described below in Table 1. The formulations for the anti-viral treatments in Groups A-G are provided in Tables 2 and 3. Each of the formulations for Groups A-E included two separate compositions that were separately stored in a dual chamber pump. Prior to application, the two compositions were dispensed and mixed together in a 1:1 ratio to provide a combined composition that was applied to the rabbit. The target pH for the combined composition was pH 8.

TABLE 1

Anti-viral treatment dosages.

| Group # | No. of rabbits | Anti-viral treatments (beginning on day 14) | Infection with CRPV (2 sites each virus) | |
|---|---|---|---|---|
| | | | wt CRPV DNA | mE8-CRPV DNA |
| A | 4 | Placebo gel | 5 ug | 5 ug |
| B | 4 | 1% Nitricil ™ NVN1 | 5 ug | 5 ug |
| C | 4 | 1.6% Nitricil ™ NVN4 | 5 ug | 5 ug |
| D | 4 | 10.0% Nitricil ™ NVN1 | 5 ug | 5 ug |
| E | 4 | 16.3% Nitricil ™ NVN4 | 5 ug | 5 ug |
| F | 4 | Placebo ointment | 5 ug | 5 ug |
| G | 4 | Single Phase, 10% Nitricil ™ NVN1 Ointment | 5 ug | 5 ug |
| H | 4 | Cidofovir (0.3% formulated in cremophor; positive control) | 5 ug | 5 ug |

TABLE 2

Formulations for the anti-viral treatments in Groups A-E.

| | % w/w | | | | |
|---|---|---|---|---|---|
| Ingredient | Placebo Gel | 1% Nitricil ™ NVN1 | 1.6% Nitricil ™ NVN4 | 10% Nitricil ™ NVN1 | 16.3% Nitricil ™ NVN4 |
| Isopropyl Alcohol | 42.75 | 41.75 | 41.15 | 33.25 | 27.25 |
| Hexylene Glycol | 5.0 | 5.0 | 5.0 | 5.0 | 5.0 |
| Cyclomethicone | 1.25 | 1.25 | 1.25 | 1.25 | 1.25 |
| Hydroxypropyl cellulose | 1.0 | 1.0 | 1.0 | 0.5 | 0.5 |
| Nitricil ™ NVN1 Drug Substance | — | 1.0 | — | 10.0 | — |
| Nitricil ™ NVN4 Drug Substance | — | — | 1.6 | — | 16 |

TABLE 2-continued

Formulations for the anti-viral treatments in Groups A-E.

| | % w/w | | | | |
|---|---|---|---|---|---|
| Ingredient | Placebo Gel | 1% Nitricil™ NVN1 | 1.6% Nitricil™ NVN4 | 10% Nitricil™ NVN1 | 16.3% Nitricil™ NVN4 |
| Purified Water | 39.65 | 40.65 | 39.65 | 40.65 | 39.65 |
| Glycerin, USP | 5.0 | 2.05 | 5.0 | 2.05 | 5.0 |
| Potassium Phosphate Monobasic | 1.35 | 5.9 | 1.35 | 5.9 | 1.35 |
| Potassium Phosphate Dibasic | 2.6 | — | 2.6 | — | 2.6 |
| Carboxymethylcellulose Sodium | 1.4 | 1.4 | 1.4 | 1.4 | 1.4 |
| Total | 100.0 | 100.0 | 100.0 | 100.0 | 100.0 |

TABLE 3

Formulations for the anti-viral treatments in Groups F and G.

| | % w/w | |
|---|---|---|
| Ingredient | Placebo Ointment | 10% Nitricil™ NVN1 Ointment |
| Mineral Oil & Polyethylene | 43.0 | 38.7 |
| White Petrolatum | 43.0 | 38.7 |
| Medium Chain Triglycerides | 8.0 | 7.2 |
| Mineral Oil | 4.0 | 3.6 |
| Macrogol 6 Glycerol Caprylocaprate | 2.0 | 1.8 |
| NVN1 Drug Substance | — | 10.0 |
| Total | 100.0 | 100.0 |

Rabbits were infected with wild-type cottontail rabbit papillomavirus (wt CRPV) and E8-knock-out CRPV (mE8-CRPV) beginning on day 1 for an early therapeutic antiviral treatment study. FIG. 1 shows the outline of experimental infections. The mE8-CRPV was included as this genome generates smaller, slower-growing papillomas that are more clinically similar to human papillomavirus infections.

A total of 32 Adult New Zealand White rabbits (including both genders) were purchased from Robinson, Pa. and used in the experiment. The rabbits were quarantined and cleared (14 days). Each rabbit was inoculated with wt CRPV (at 2 sites; 5 μg/site) and mE8-CRPV viral DNA (at 2 sites; 5 μg/site). CRPV viral DNA was used to generate papillomas and infection was developed via a delayed scarification technique (Cladel N. M., et al., *J Virol Methods* 2008; 148(1-2):34-39). Of the two sites inoculated with one of the viruses, one site received treatment (i.e., the left site (L1 or L2)) and the other site was untreated (i.e., the right site (R1 or R2)).

The rabbits were placed into one of eight groups (Groups A-H). A placebo group (i.e., Group A) served as a control to assess local effects of treatment in treated Groups B-H. Groups B-G represented test compound comparisons vs. placebo negative control.

Treatments for Groups A-H began at week two at a time when the papillomas were not yet visible. This time point allowed for effects on subclinical papillomas to be assessed. Treatment was 5× weekly (Monday-Friday), for five weeks with a dose of 0.1 ml per approximately 2.5 cm×2.5 cm site for topical treatments. Body weights were taken weekly, and blood sera were collected at the end of the treatment period for blood chemistries, as needed.

The frequency and size of papillomas was measured weekly in 3 axes (length×width×height) in mm. Data was entered into a spread sheet and calculations were conducted of the geometric mean diameter of each papilloma, mean±SEM for each group, Student's t-test between each paired groups and plots made of papilloma size vs time. Plots of weight changes were also conducted.

At termination, kidney and liver samples were retrieved for histology and toxicity assessment, as needed. Skin/papilloma sites were monitored photographically and biopsies assessed for histology at experiment/treatment termination.

Figure 10:
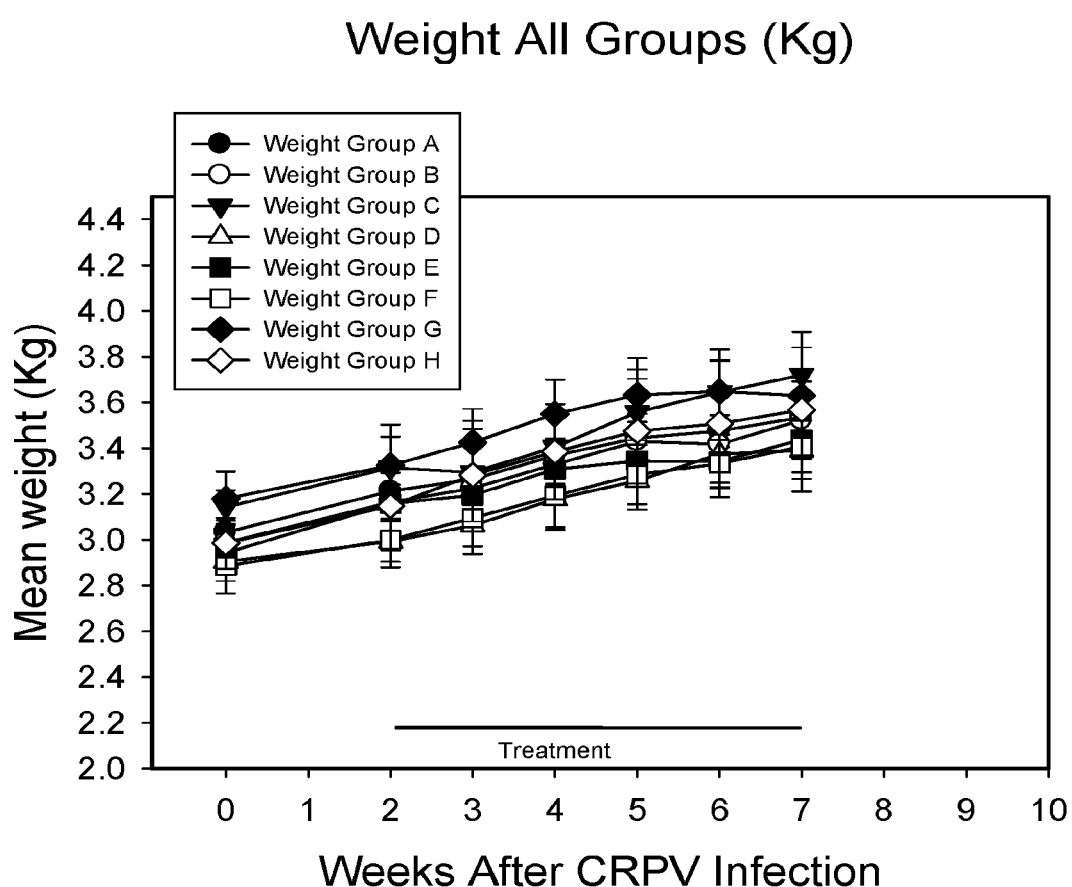
FIG. 10 shows a graph of mean±SEM rabbit weight (kg) for rabbits in Groups A-H. Weights are plotted together with SEM error bars against time after infection with CRPV.
Figure 11:
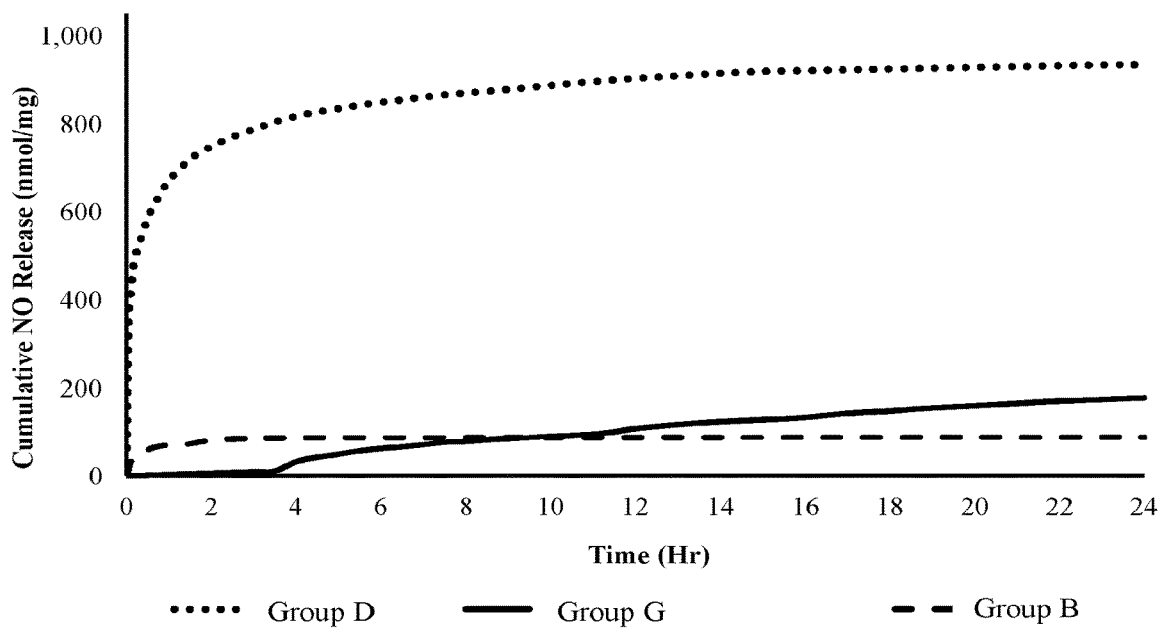
FIG. 11 shows a graph of the cumulative nitric oxide (NO) release over time for the formulations used in Groups B, D, and G.
Figure 12:
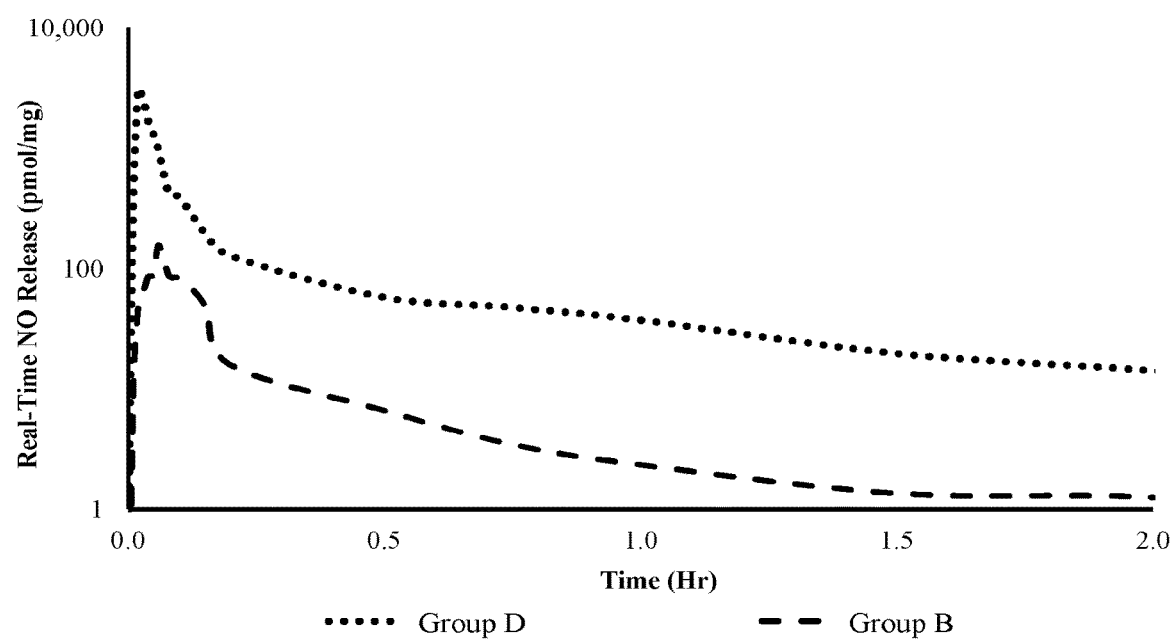
FIG. 12 shows a graph of the real time NO release over time for the formulations used in Groups B and D.
Figure 13:
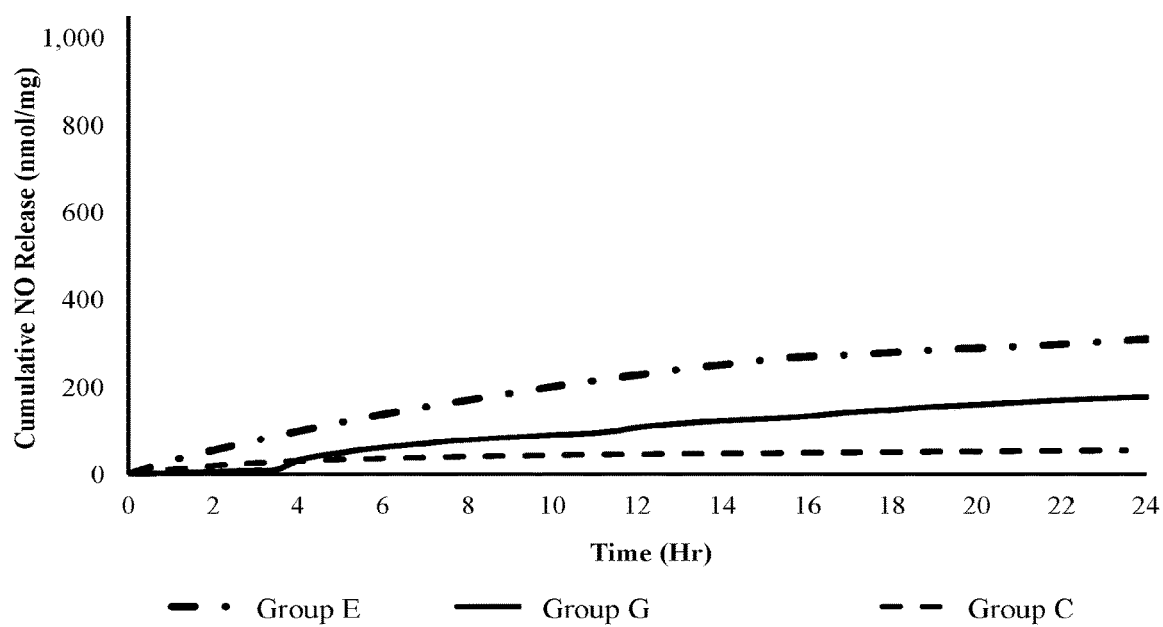
FIG. 13 shows a graph of the cumulative NO release over time for the formulations used in Groups C, E, and G.
Figure 14:
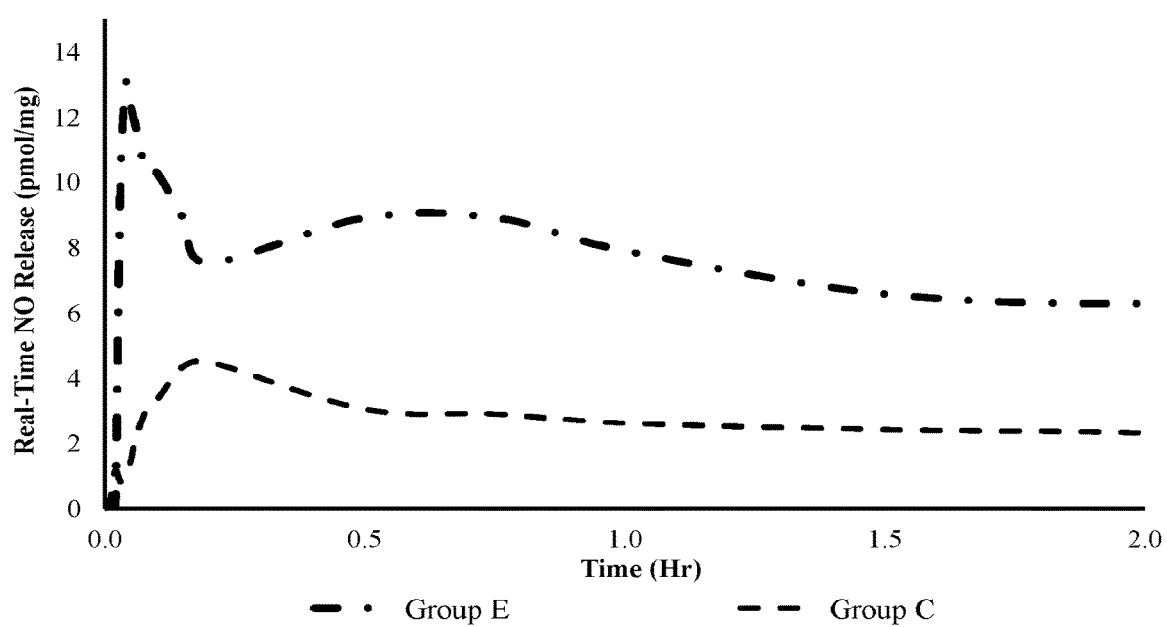
FIG. 14 shows a graph of the real time NO release over time for the formulations used in Groups C and E.
Figure 15:
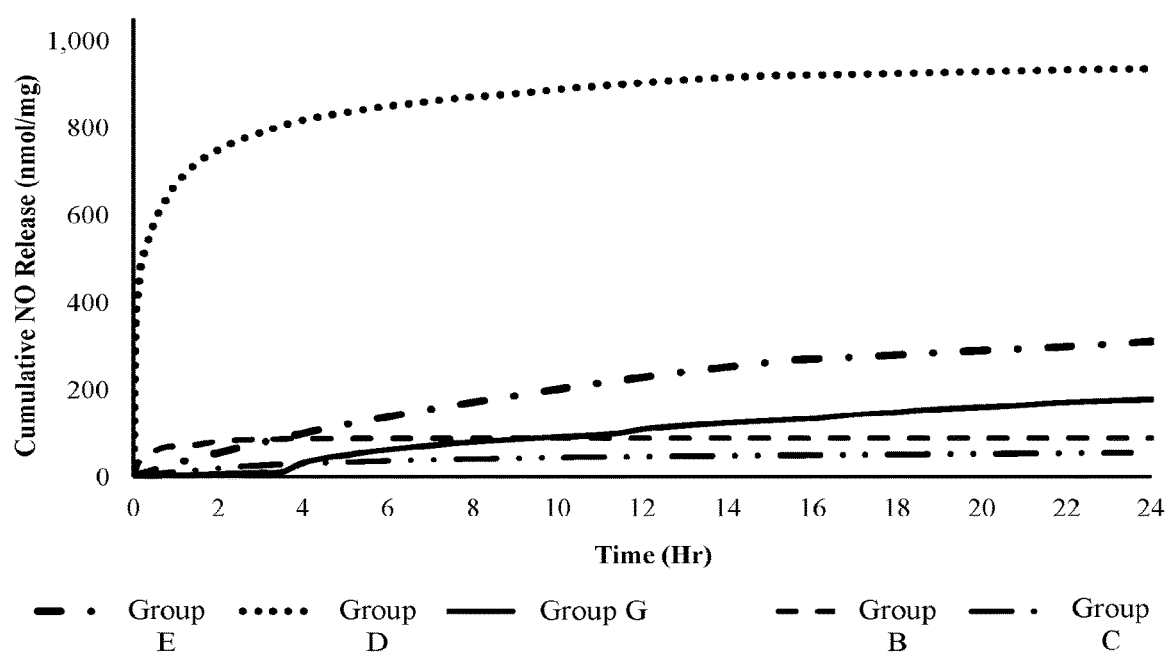
FIG. 15 shows a graph of the cumulative NO release over time for the formulations used in Groups B, C, D, E, and G.
Figure 16A:
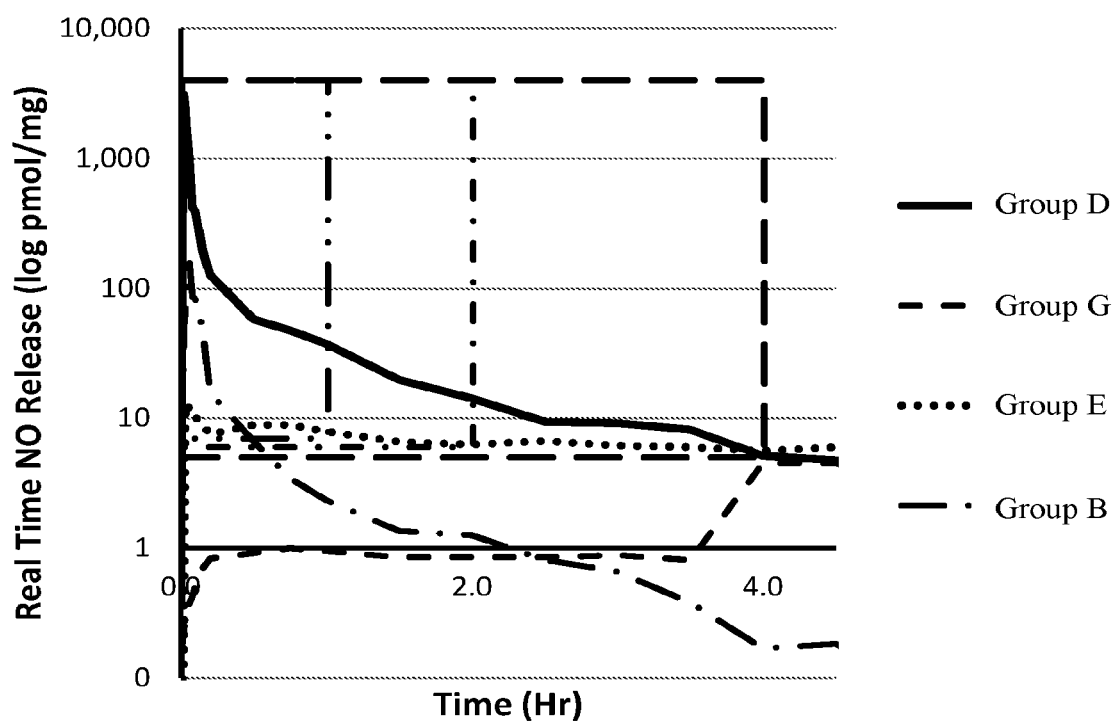
FIG. 16A shows a graph of the real time NO release in pmol/mg for the formulations used in Groups B, D, E and G with rectangles representing 1 hour, 2 hour, and 4 hour time periods with ranges of NO release according to some embodiments of the present invention.
Figure 16B:
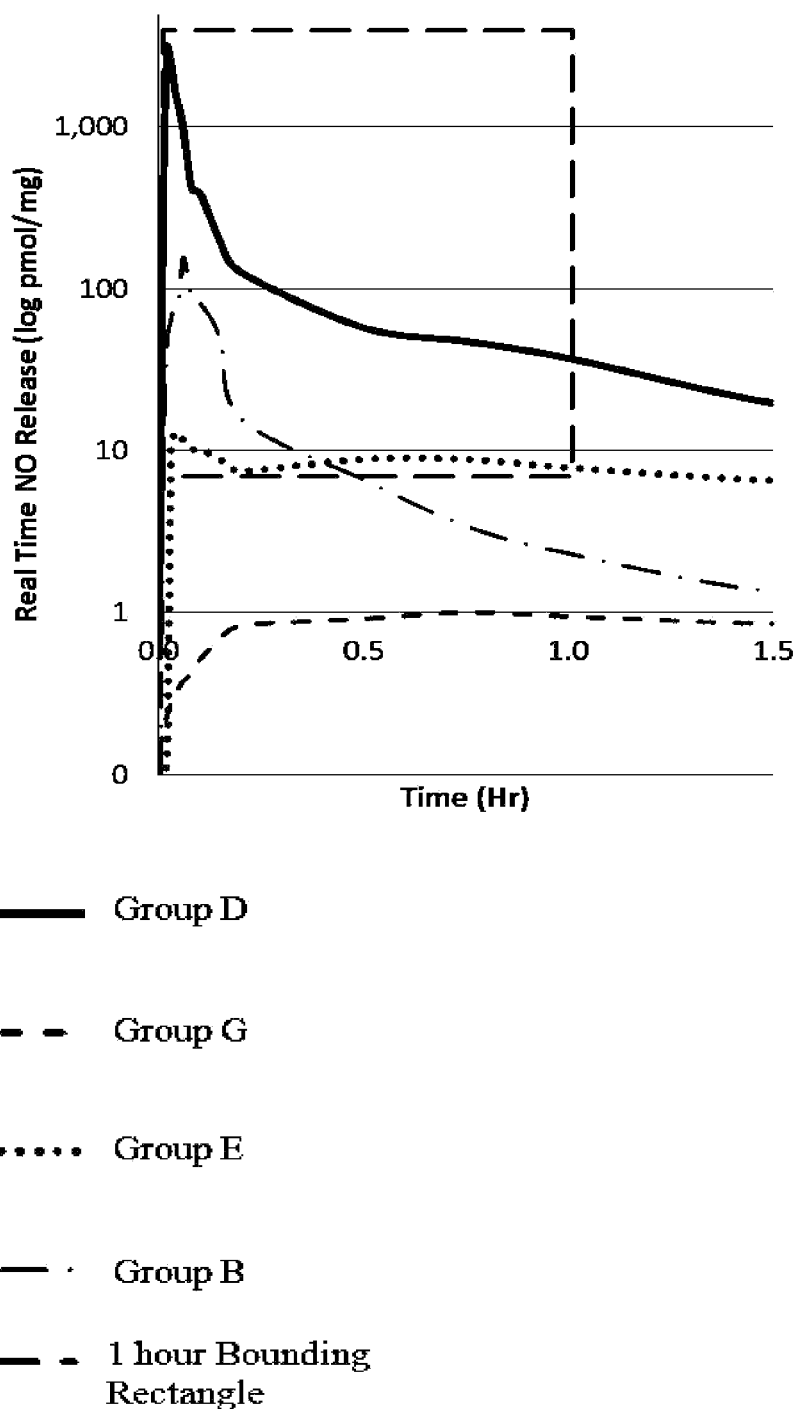
FIG. 16B is an enlarged version of the first 1.5 hours of FIG. 16A with a rectangle representing the 1 hour time period with ranges of NO release according to some embodiments of the present invention.

FIGS. 2-9 show plots of mean (±SEM) of the GMD measurements for each treatment group plotted against time after CRPV infection. For calculations of mean GMDs, the spontaneous regressor in Group D was not used. FIG. 10 shows mean body weights for the treatment groups.

Figure 2:
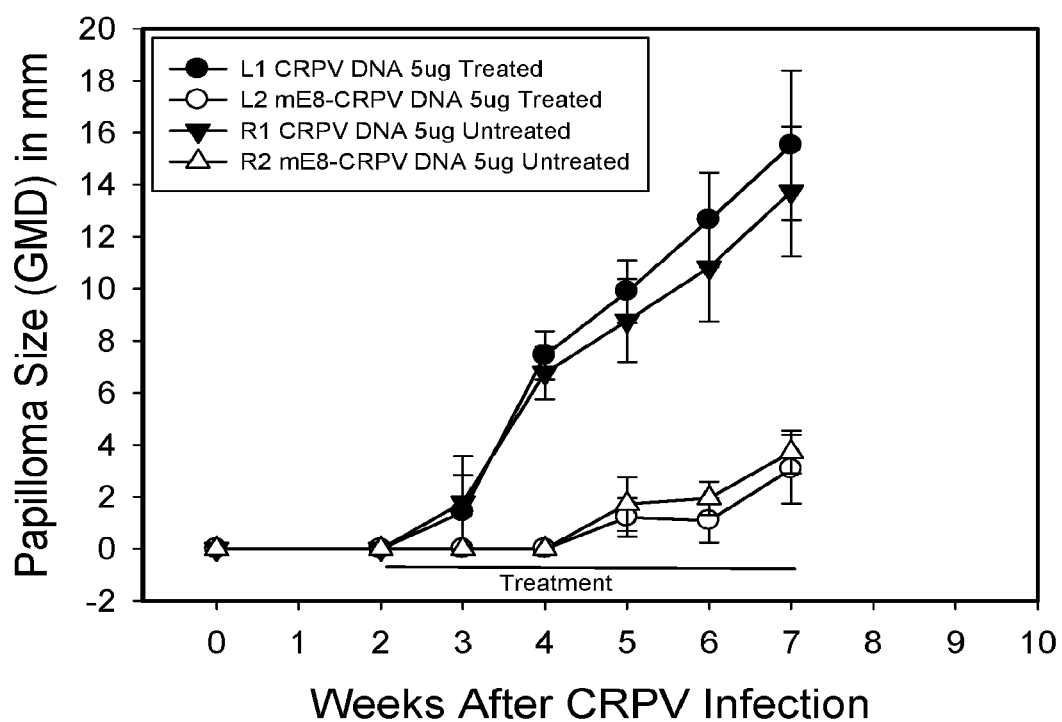
FIG. 2 shows a graph of the mean±SEM of geometric mean diameter (GMD) measurements of CRPV-induced rabbit papillomas from rabbits in Group A. Papillomas were induced at 2 sites with 5 µg of wt-CRPV plasmid stock (●,▼), and at 2 sites with 5 µg mE8-CRPV plasmid stock (○,△). Left sites (L1 and L2) were treated topically with placebo gel (●,○) and right sites (R1 and R2) were untreated (▼,△). Each symbol represents the mean (±SEM) of GMDs of the weekly measurements.
Figure 3:
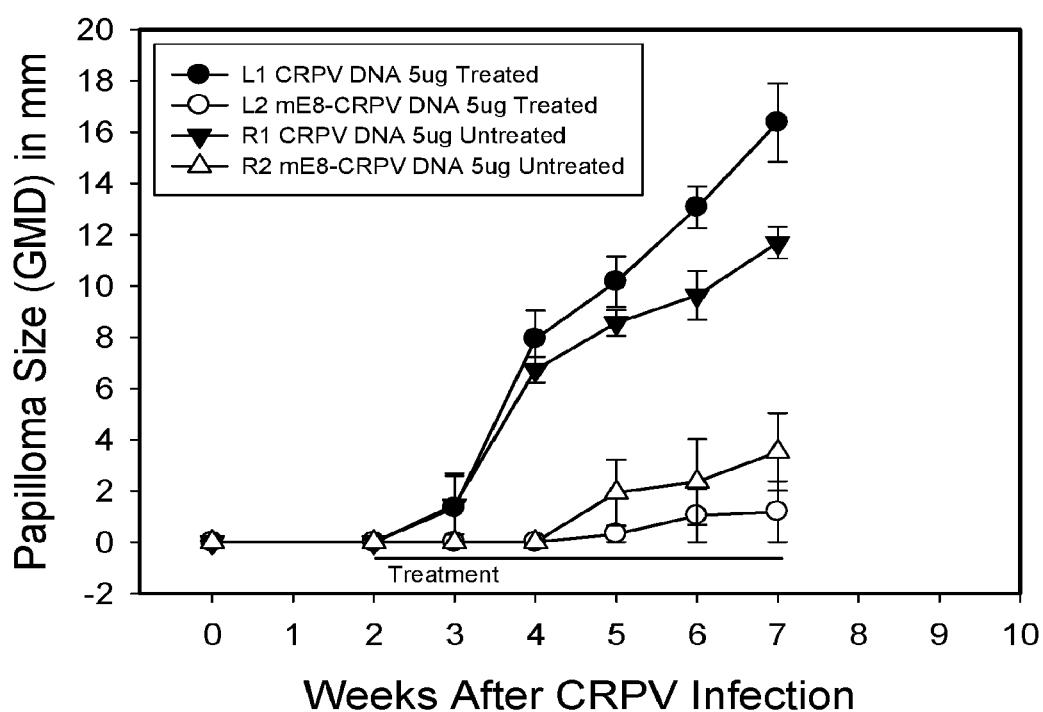
FIG. 3 shows a graph of mean±SEM of GMD measurements of CRPV-induced rabbit papillomas from rabbits in Group B. Papillomas were induced at 2 sites with 5 µg of wt-CRPV plasmid stock (●,▼), and at 2 sites with 5 µg mE8-CRPV plasmid stock (○,△). Left sites (L1 and L2) were treated topically with 1% Nitricil™ NVN1 (●,○) and right sites (R1 and R2) were untreated (▼,△). Each symbol represents the mean (±SEM) of GMDs of the weekly measurements.
Figure 4:
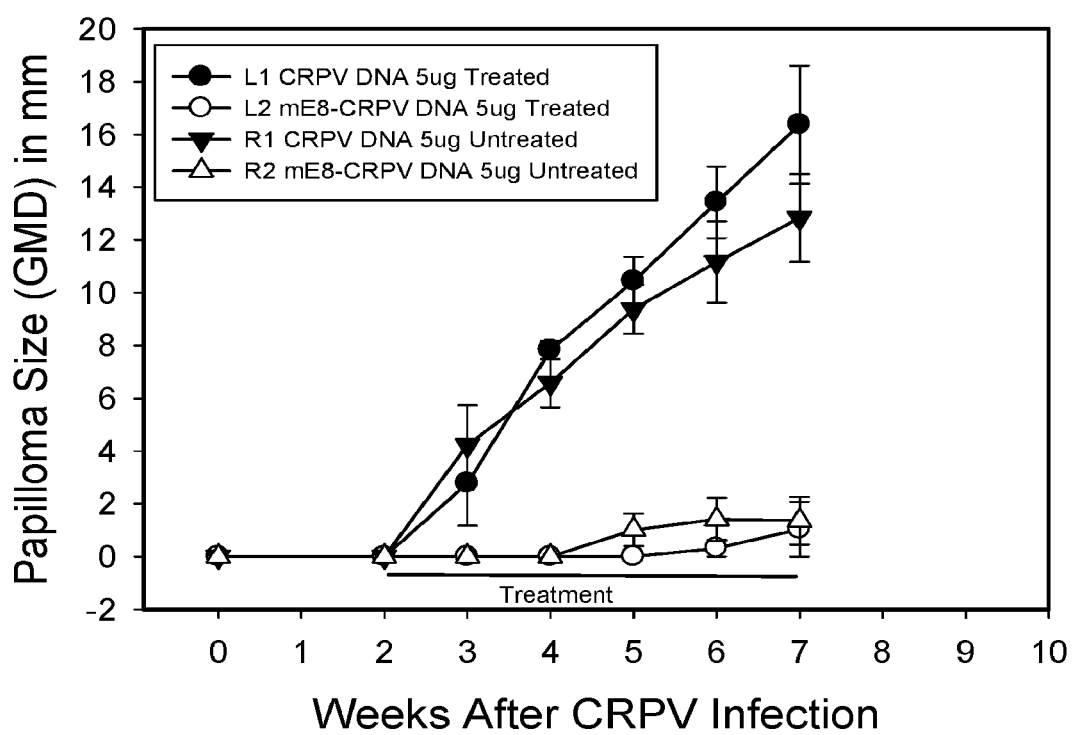
FIG. 4 shows a graph of mean±SEM of GMD measurements of CRPV-induced rabbit papillomas from rabbits in Group C. Papillomas were induced at 2 sites with 5 µg of wt-CRPV plasmid stock (●,▼), and at 2 sites with 5 µg mE8-CRPV plasmid stock (○,△). Left sites (L1 and L2) were treated topically with 1.6% Nitricil™ NVN4 (●,○) and right sites (R1 and R2) were untreated (▼,△). Each symbol represents the mean (±SEM) of GMDs of the weekly measurements.
Figure 5:
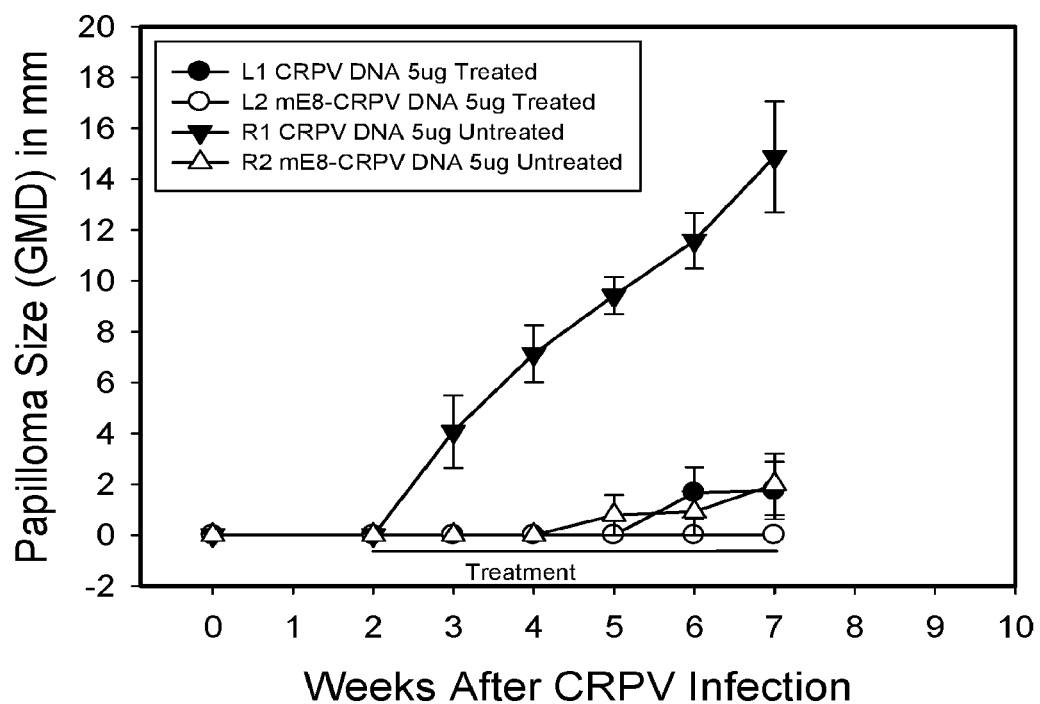
FIG. 5 shows a graph of mean±SEM of GMD measurements of CRPV-induced rabbit papillomas from rabbits in Group D. Papillomas were induced at 2 sites with 5 µg of wt-CRPV plasmid stock (●,▼), and at 2 sites with 5 µg mE8-CRPV plasmid stock (○,△). Left sites (L1 and L2) were treated topically with 10% Nitricil™ NVN1 (●,○) and right sites (R1 and R2) were untreated (▼,△). Each symbol represents the mean (±SEM) of GMDs of the weekly measurements.
Figure 6:
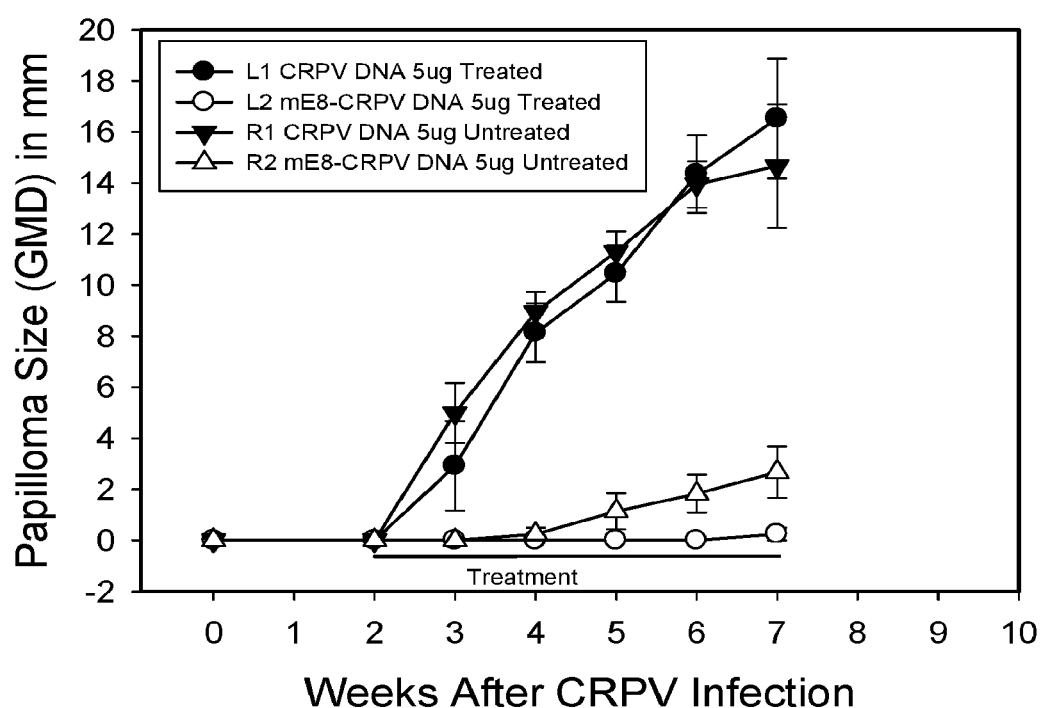
FIG. 6 shows a graph of mean±SEM of GMD measurements of CRPV-induced rabbit papillomas from rabbits in Group E. Papillomas were induced at 2 sites with 5 µg of wt-CRPV plasmid stock (●,▼), and at 2 sites with 5 µg mE8-CRPV plasmid stock (○,Δ). Left sites (L1 and L2) were treated topically with 16.3% Nitricil™ NVN4 (●,○) and right sites (R1 and R2) were untreated (▼,Δ). Each symbol represents the mean (±SEM) of GMDs of the weekly measurements.
Figure 7:
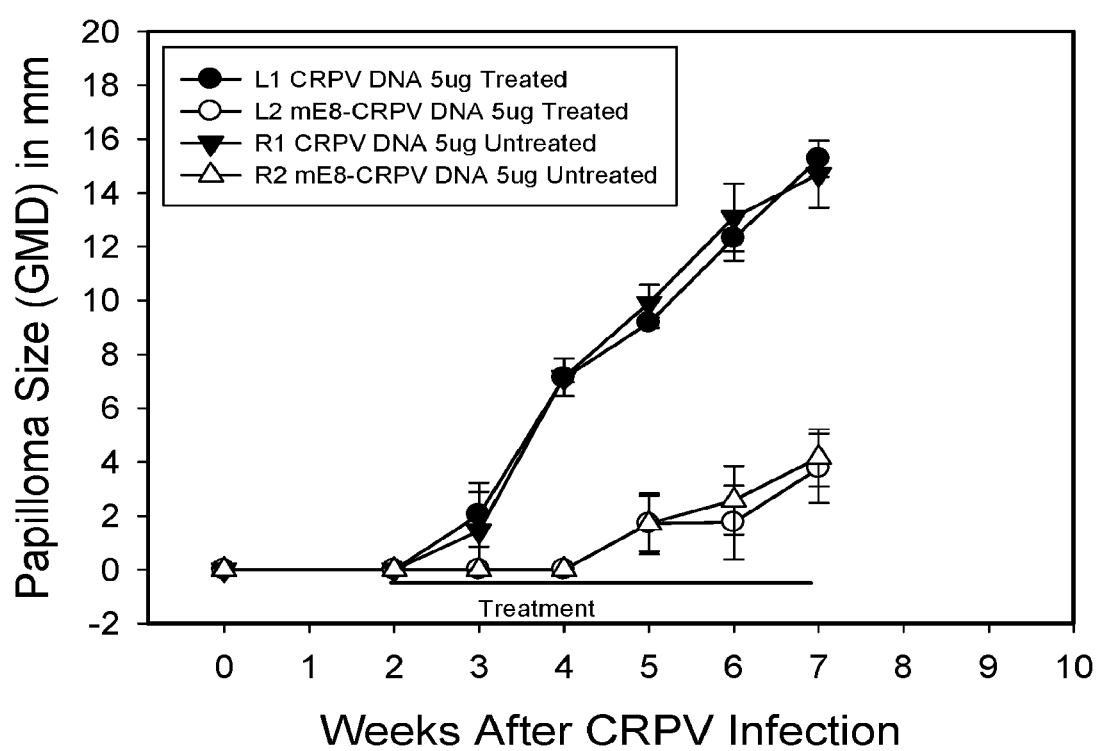
FIG. 7 shows a graph of mean±SEM of GMD measurements of CRPV-induced rabbit papillomas from rabbits in Group F. Papillomas were induced at 2 sites with 5 µg of wt-CRPV plasmid stock (●,▼), and at 2 sites with 5 µg mE8-CRPV plasmid stock (○,Δ). Left sites (L1 and L2) were treated topically with placebo ointment (●,○) and right sites (R1 and R2) were untreated (▼,Δ). Each symbol represents the mean (±SEM) of GMDs of the weekly measurements.
Figure 8:
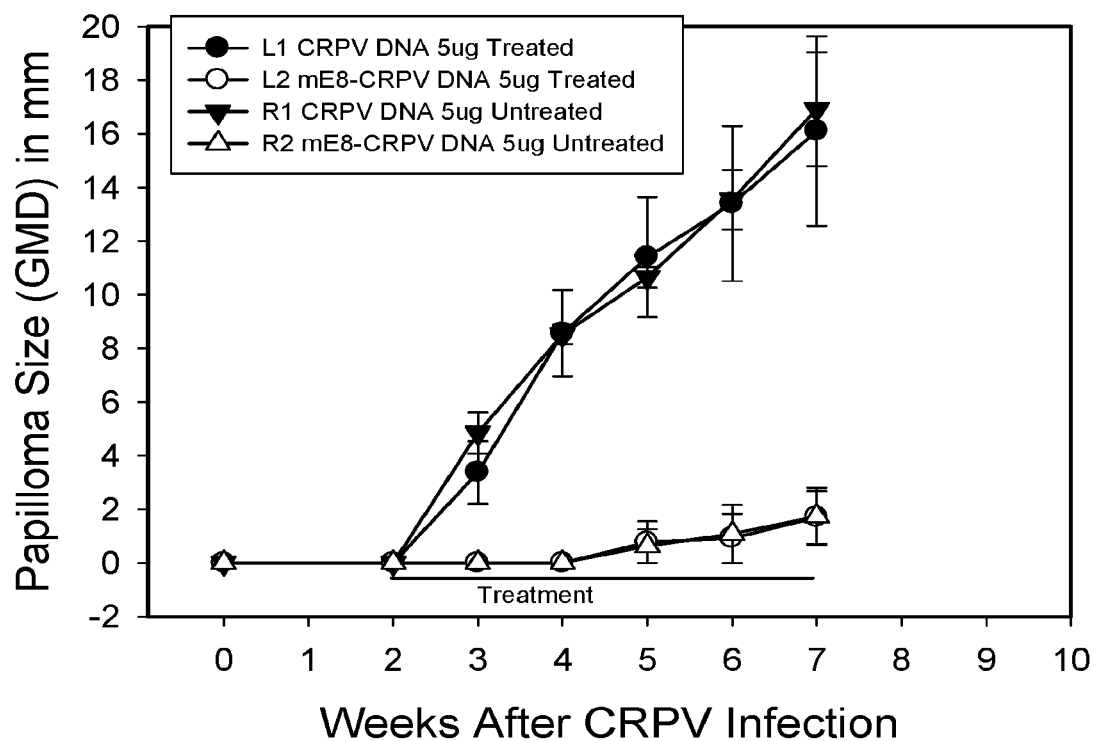
FIG. 8 shows a graph of mean±SEM of GMD measurements of CRPV-induced rabbit papillomas from rabbits in Group G. Papillomas were induced at 2 sites with 5 µg of wt-CRPV plasmid stock (●,▼), and at 2 sites with 5 µg mE8-CRPV plasmid stock (○,Δ). Left sites (L1 and L2) were treated topically with a single phase, 10% Nitricil™ NVN1 ointment (●,○) and right sites (R1 and R2) were untreated (▼,Δ). Each symbol represents the mean (±SEM) of GMDs of the weekly measurements.
Figure 9:
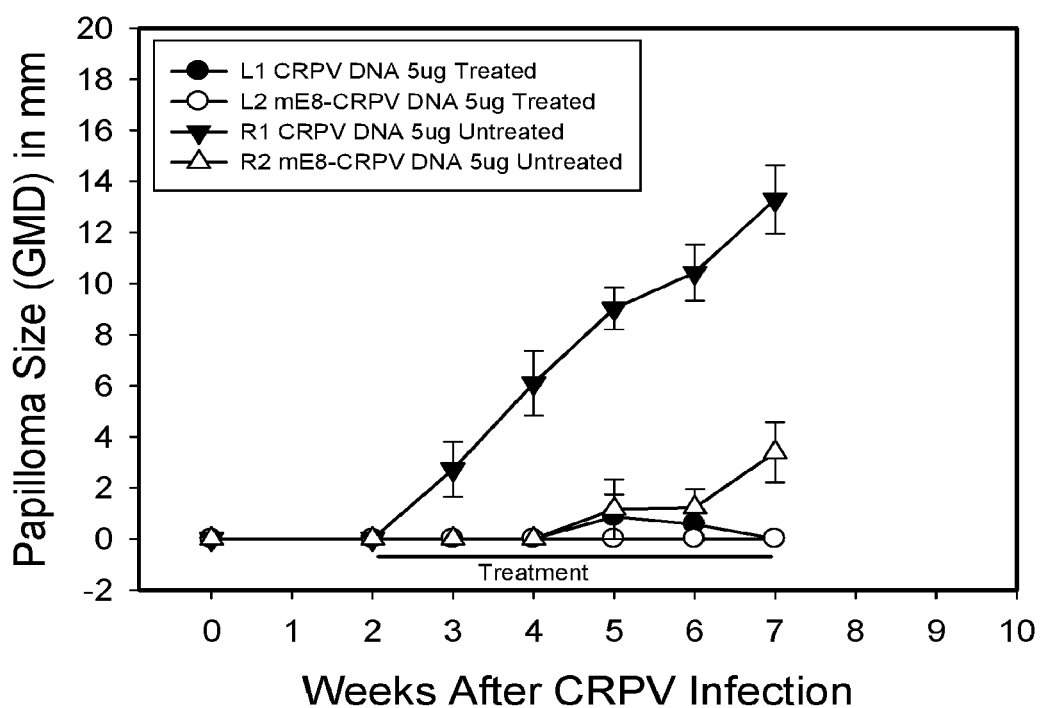
FIG. 9 shows a graph of mean±SEM of GMD measurements of CRPV-induced rabbit papillomas from rabbits in Group H. Papillomas were induced at 2 sites with 5 µg of wt-CRPV plasmid stock (●,▼), and at 2 sites with 5 µg mE8-CRPV plasmid stock (○,Δ). Left sites (L1 and L2) were treated topically with 0.3% cidofovir in cremophor (50%) (●,○) and right sites (R1 and R2) were untreated (▼,Δ). Each symbol represents the mean (±SEM) of GMDs of the weekly measurements.

As seen in FIG. 2, the gel vehicle without a NO-releasing API provided little to no separation in papilloma size between the treated and untreated sites for either the wild type or mE8-CRPV mutant papilloma virus sites. In FIG. 3, the 1% Nitricil™ NVN1 group showed some separation between treated and untreated sites for the mutant strain. However, complete inhibition of papilloma growth was not achieved. In FIG. 4, the 1.6% Nitricil™ NVN4 group showed little or no separation between treated and untreated sites for wild type virus and mutant strain. FIG. 5 shows that 10% Nitricil™ NVN1 was effective in treating both wild type virus and the mutant strain with complete inhibition of papilloma growth in the mutant strain and substantial separation between treated and untreated sites in the faster growing wild type. FIG. 6 shows that 16.3% Nitricil™ NVN4 was effective at inhibiting growth of the mutant strain but was not effective at inhibiting growth of the wild type virus. As seen in FIG. 7, the ointment vehicle without a NO-releasing API provided little to no separation in papilloma size between the treated and untreated sites for either the wild type or mutant papilloma virus sites. As seen in FIG. 8, the 10% NVN1 ointment provided little to no separation in papilloma size between the treated and untreated sites for either the wild type or mutant papilloma virus sites, illustrating the release of nitric oxide from the composition affects the effectiveness of inhibiting papilloma growth, as opposed to the presence of the siloxane backbone as the 10% NVN1 ointment and the 10% NVN1 gel both contained the same amount of the polysiloxane backbone but achieved markedly different results.

Example 2

In vitro release testing was performed using multi-channel Nitric Oxide Analyzer. An analytical balance was used to weigh the test formulations from Groups B-E and G described in Example 1. Approximately 20-mg of both-phases of a respective formulation were transferred to a clean, dry NO measurement cell with a magnetic stir bar. The real time in vitro release of nitric oxide from the formulations was determined while under continuous mixing using the following instrumental parameters:

1. Moist Nitrogen Flow Rate: 112-115 ml/min
2. Sample Temperature: 37° C.
3. Detection: Nitric Oxide by Chemiluminescence
4. Data Acquisition Frequency: 1 Hz, Irregular Sequential Alternating
5. Duration: Time at which NO release rate decreases linearly (NLT 8 hr)
6. Acquisition Software: NovanWare Conversion from parts per billion (PPB) NO to moles nitric oxide was achieved by measuring the nitric oxide generated from a known amount of sodium nitrite in a solution of potassium iodide to acquire a PPB-to-mole conversion factor. Any gaps in real time nitric oxide release data resulting from multichannel operation were filled in by using a linear interpolation program. For any sample that was not measured to exhaustion of nitric oxide, a linear extrapolation to zero release of the last ~5000 sec of release was performed. Real time nitric oxide release data was then integrated, resulting in a total nitric oxide accumulation curve. Nitric oxide release parameters such as $C_{max}$ (i.e., the maximum concentration of NO released), $T_{max}$ (i.e., the time at which $C_{max}$ is achieved), Cumulative Nitric Oxide Released (i.e., the sum of all data points per unit time), and Time to Half of Total Released ($T_{50}$) (i.e., the time at which 50% of the cumulative NO is released) can be calculated from both the real time and total accumulation nitric oxide release curves. All of the above calculations were performed automatically in custom-built data processing software (NovanWare).

The results from in vitro release testing, along with the respective pH of the admixtures are summarized in Table 4 below.

TABLE 4

NO release data for the formulations tested

| Group | Formulation | 24 Hour Cumulative Release (nmol/mg) | $T_{50}$ for 24 hours (minutes) | $C_{max}$, $T_{max}$ (pmol/mg) | Real Time Release (pmol/mg) |
|---|---|---|---|---|---|
| B | 1% Nitricil ™ NVN1 | 88.8 | 11.3 | 156.1 at 3.6 minutes | 6.7 at 0.5 hours<br>2.3 at 1 hour<br>1.3 at 2 hours<br>0.7 at 3 hours<br>0.2 at 4 hours |
| C | 1.6% Nitricil ™ NVN4 | 54.9 | 198 | 4.5 at 12 minutes | 3.1 at 0.5 hours<br>2.6 at 1 hour<br>2.3 at 2 hours<br>1.5 at 3 hours<br>1.1 at 4 hours |
| D | 10% Nitricil ™ NVN1 | 934.7 | 9.15 | 3107.5 at 1.2 minutes | 57.7 at 0.5 hours<br>37.4 at 1 hour<br>14.2 at 2 hours<br>9.2 at 3 hours<br>5.1 at 4 hours |
| E | 16.3% Nitricil ™ NVN4 | 310.8 | 420 | 13.0 at 2.4 minutes | 8.9 at 0.5 hours<br>7.9 at 1 hour<br>6.3 at 2 hours<br>6.2 at 3 hours<br>5.6 at 4 hours |
| G | 10% Nitricil ™ NVN1 Ointment | 178.6 | 582 | 5.8 at 690 minutes | 0.9 at 0.5 hours<br>1.0 at 1 hour<br>0.9 at 2 hours<br>0.9 at 3 hours<br>4.5 at 4 hours |

Example 3

The test articles in Example 2 were applied to the 2.5 cm×2.5 cm sites of the rabbits of Example 1. Application of 0.1 mL of the test articles to 6.25 cm² results in an in vitro assay release of NO/cm² as reflected in Table 5.

TABLE 5

NO release per unit area data for the formulations tested

| Group | Formulation | Cumulative Release (nmol/cm²) | $C_{max}$, $T_{max}$ (pmol/cm²) | Real Time Release (pmol/cm²) |
|---|---|---|---|---|
| B | 1% Nitricil ™ NVN1 | 878.5 at 0.5 hours<br>1044.6 at 1 hour<br>1226.9 at 2 hours<br>1274.4 at 3 hours | 2322.7 at 3.6 minutes | 99.1 at 0.5 hours<br>34.8 at 1 hour<br>18.7 at 2 hours<br>9.8 at 3 hours |

TABLE 5-continued

NO release per unit area data for the formulations tested

| Group | Formulation | Cumulative Release (nmol/cm$^2$) | $C_{max}$, $T_{max}$ (pmol/cm$^2$) | Real Time Release (pmol/cm$^2$) |
|---|---|---|---|---|
| | | 1294.8 at 4 hours | | 2.5 at 4 hours |
| | | 1230.8 at 24 hours | | |
| C | 1.6% Nitricil ™ NVN4 | 85.4 at 0.5 hours | 67.1 at 12 minutes | 45.4 at 0.5 hours |
| | | 164.4 at 1 hour | | 39.1 at 1 hour |
| | | 291.3 at 2 hours | | 34.5 at 2 hours |
| | | 386.5 at 3 hours | | 21.6 at 3 hours |
| | | 453.8 at 4 hours | | 15.6 at 4 hours |
| | | 816.3 at 24 hours | | |
| D | 10% Nitricil ™ NVN1 | 8701.2 at 0.5 hours | 3107.5 at 1.2 minutes | 859.0 at 0.5 hours |
| | | 9975.1 at 1 hour | | 556.5 at 1 hour |
| | | 11141.0 at 2 hours | | 211.9 at 2 hours |
| | | 11730.8 at 3 hours | | 136.9 at 3 hours |
| | | 12173.8 at 4 hours | | 76.5 at 4 hours |
| | | 13908.2 at 24 hours | | |
| E | 16.3% Nitricil ™ NVN4 | 241.9 at 0.5 hours | 193.8 at 2.4 minutes | 132.6 at 0.5 hours |
| | | 468.5 at 1 hour | | 117.6 at 1 hour |
| | | 824.6 at 2 hours | | 93.7 at 2 hours |
| | | 1163.5 at 3 hours | | 91.8 at 3 hours |
| | | 1484.1 at 4 hours | | 83.5 at 4 hours |
| | | 4624.5 at 24 hours | | |
| G | 10% Nitricil ™ NVN1 Ointment | 19.1 at 0.5 hours | 82.8 at 690 minutes | 13.2 at 0.5 hours |
| | | 42.7 at 1 hour | | 13.6 at 1 hour |
| | | 88.1 at 2 hours | | 12.3 at 2 hours |
| | | 132.9 at 3 hours | | 12.7 at 3 hours |
| | | 457.6 at 4 hours | | 64.7 at 4 hours |
| | | 2572.0 at 24 hours | | |

Figure 17:
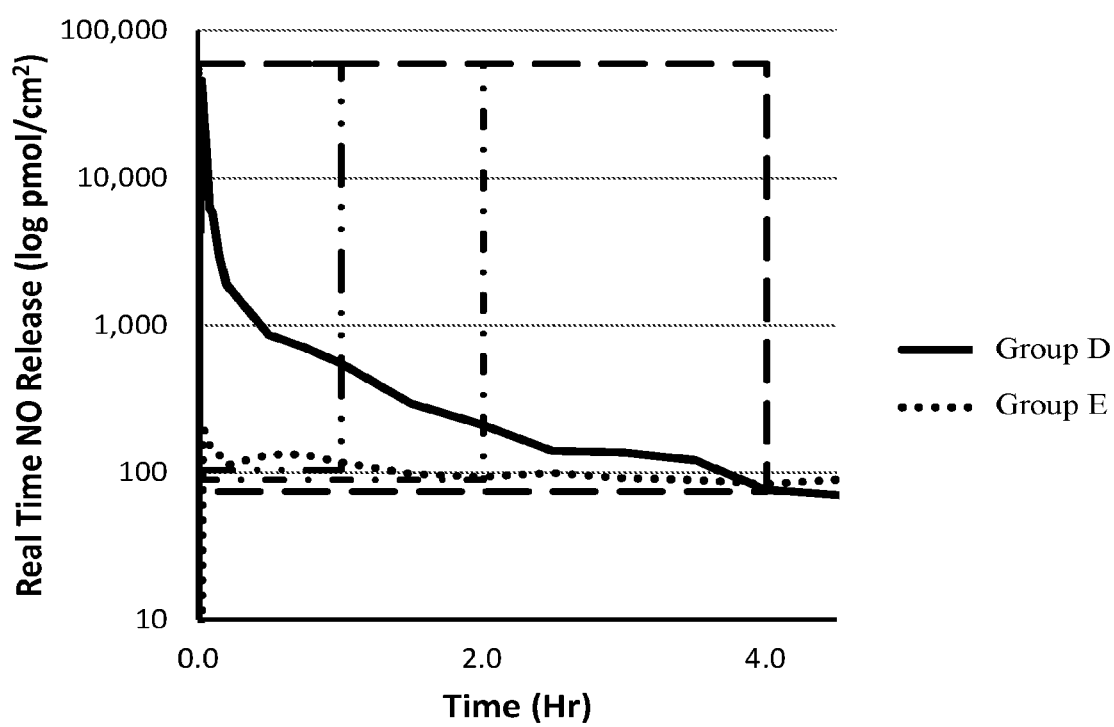
FIG. 17 shows a graph of the real time NO release in pmol/cm$^2$ for the formulations used in Groups D and E with rectangles representing 1 hour, 2 hour, and 4 hour time periods with ranges of NO release per cm$^2$ according to some embodiments of the present invention.
Figure 18:
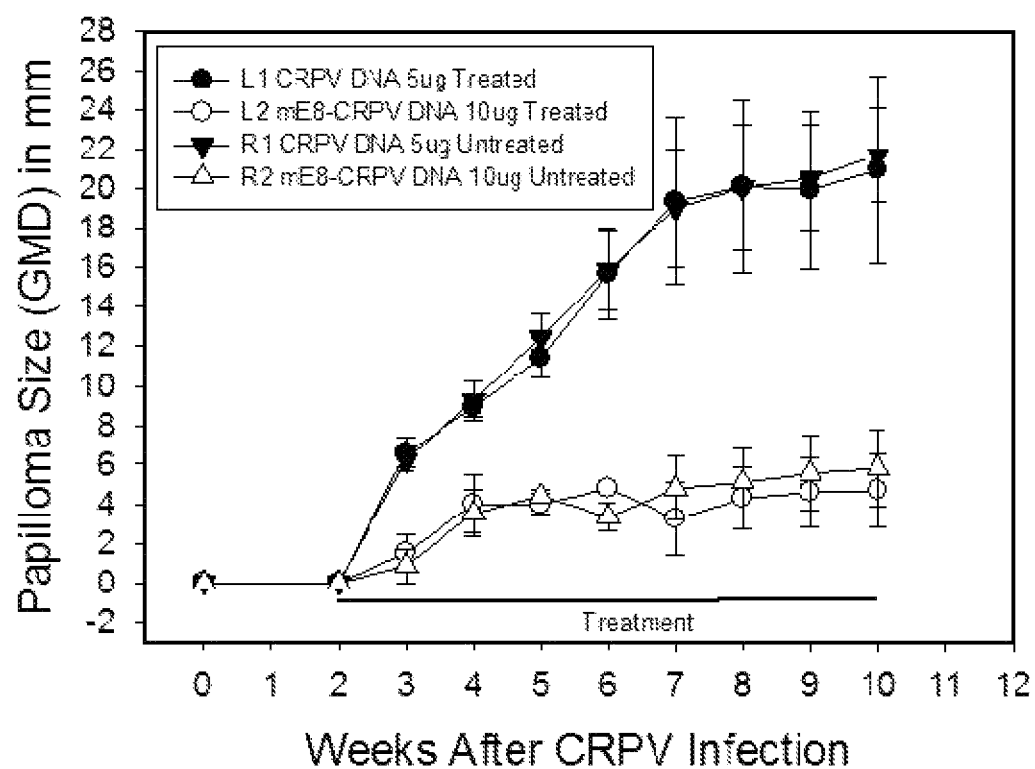
FIG. 18 shows a graph of papilloma size (GMD) in mm over time for the formulation used in Group A. Papillomas were induced at 2 sites with 5 µg of wt-CRPV plasmid stock (●,▼), and at 2 sites with 5 µg mE8-CRPV plasmid stock (○,Δ). Left sites (L1 and L2) were treated topically with the placebo (●,○) and right sites (R1 and R2) were untreated (▼,Δ). Each symbol represents the mean (±SEM) of GMDs of the weekly measurements.
Figure 19:
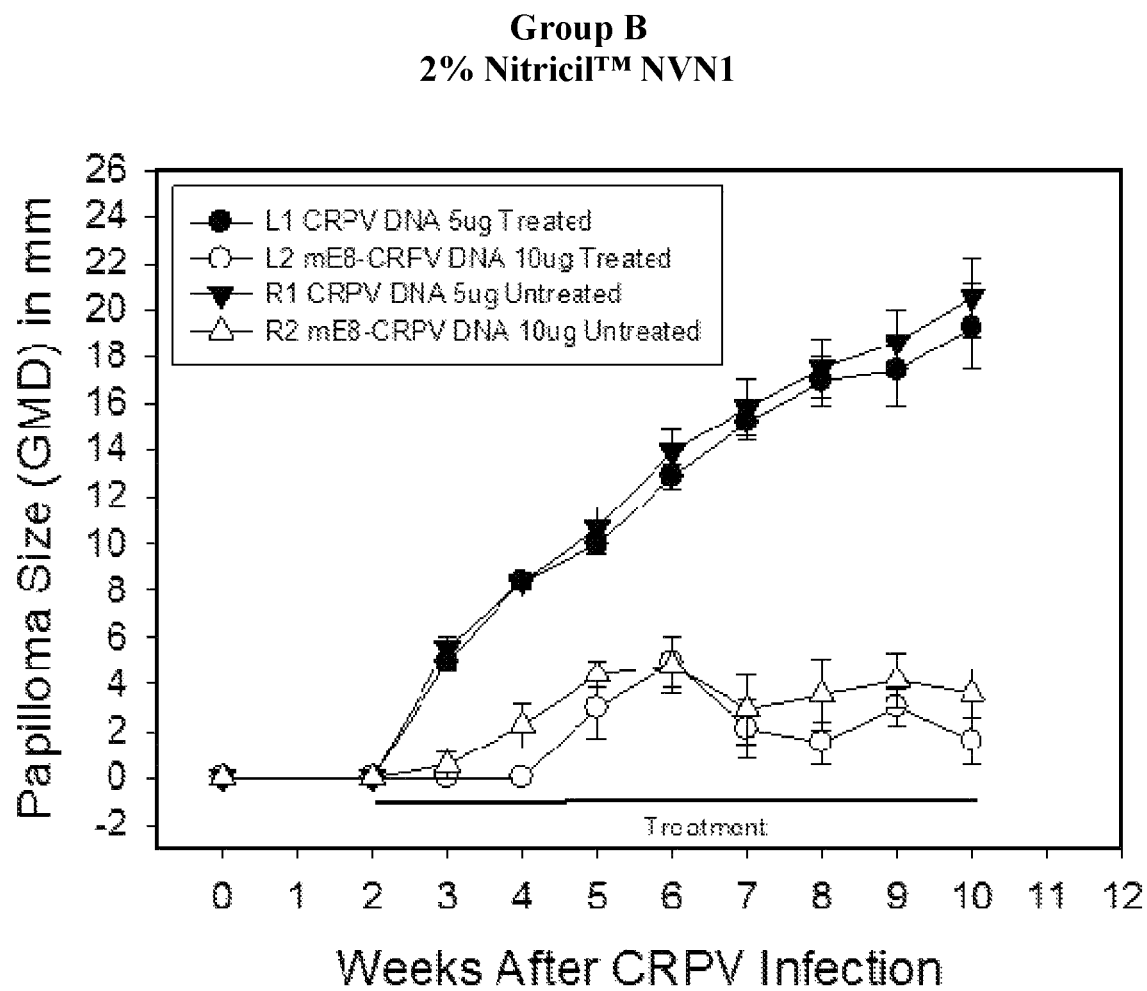
FIG. 19 shows a graph of papilloma size (GMD) in mm over time for the formulation used in Group B. Papillomas were induced at 2 sites with 5 µg of wt-CRPV plasmid stock (●,▼), and at 2 sites with 5 µg mE8-CRPV plasmid stock (○,Δ). Left sites (L1 and L2) were treated topically with the 2% Nitricil™ NVN1 formulation (●,○) and right sites (R1 and R2) were untreated (▼,Δ). Each symbol represents the mean (±SEM) of GMDs of the weekly measurements.
Figure 20:
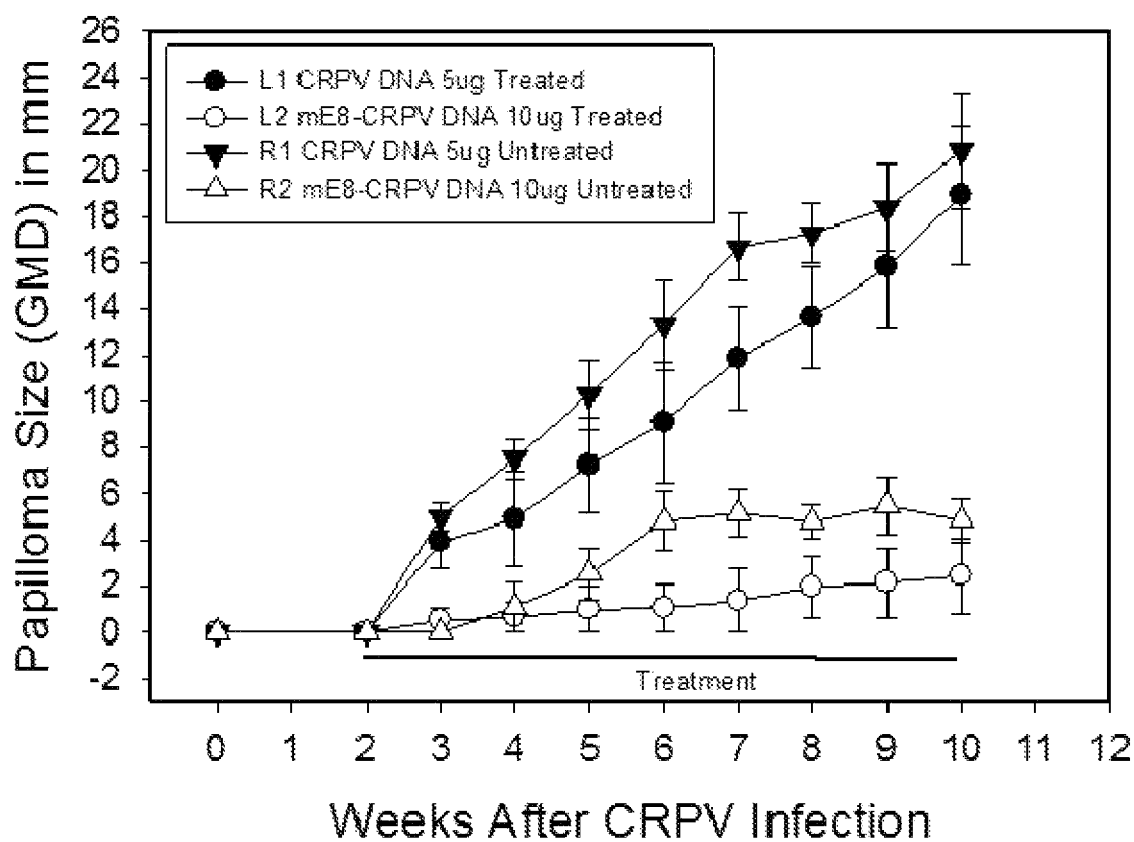
FIG. 20 shows a graph of papilloma size (GMD) in mm over time for the formulation used in Group C. Papillomas were induced at 2 sites with 5 µg of wt-CRPV plasmid stock (●,▼), and at 2 sites with 5 µg mE8-CRPV plasmid stock (○,Δ). Left sites (L1 and L2) were treated topically with the 4% Nitricil™ NVN1 formulation (●,○) and right sites (R1 and R2) were untreated (▼,Δ). Each symbol represents the mean (±SEM) of GMDs of the weekly measurements.
Figure 21:
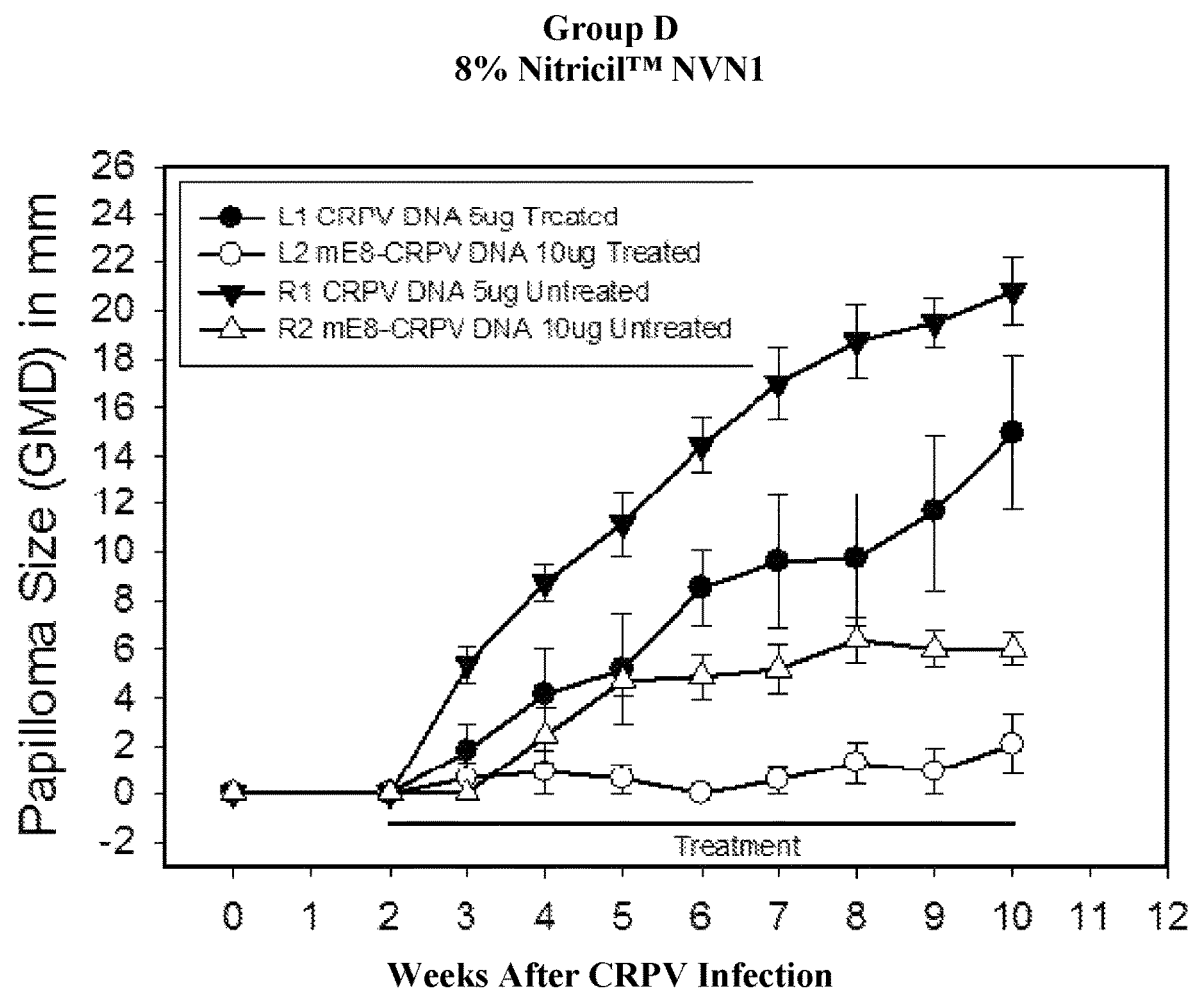
FIG. 21 shows a graph of papilloma size (GMD) in mm over time for the formulation used in Group D. Papillomas were induced at 2 sites with 5 µg of wt-CRPV plasmid stock (●,▼), and at 2 sites with 5 µg mE8-CRPV plasmid stock (○,Δ). Left sites (L1 and L2) were treated topically with the 8% Nitricil™ NVN1 formulation (●,○) and right sites (R1 and R2) were untreated (▼,Δ). Each symbol represents the mean (±SEM) of GMDs of the weekly measurements.
Figure 22:
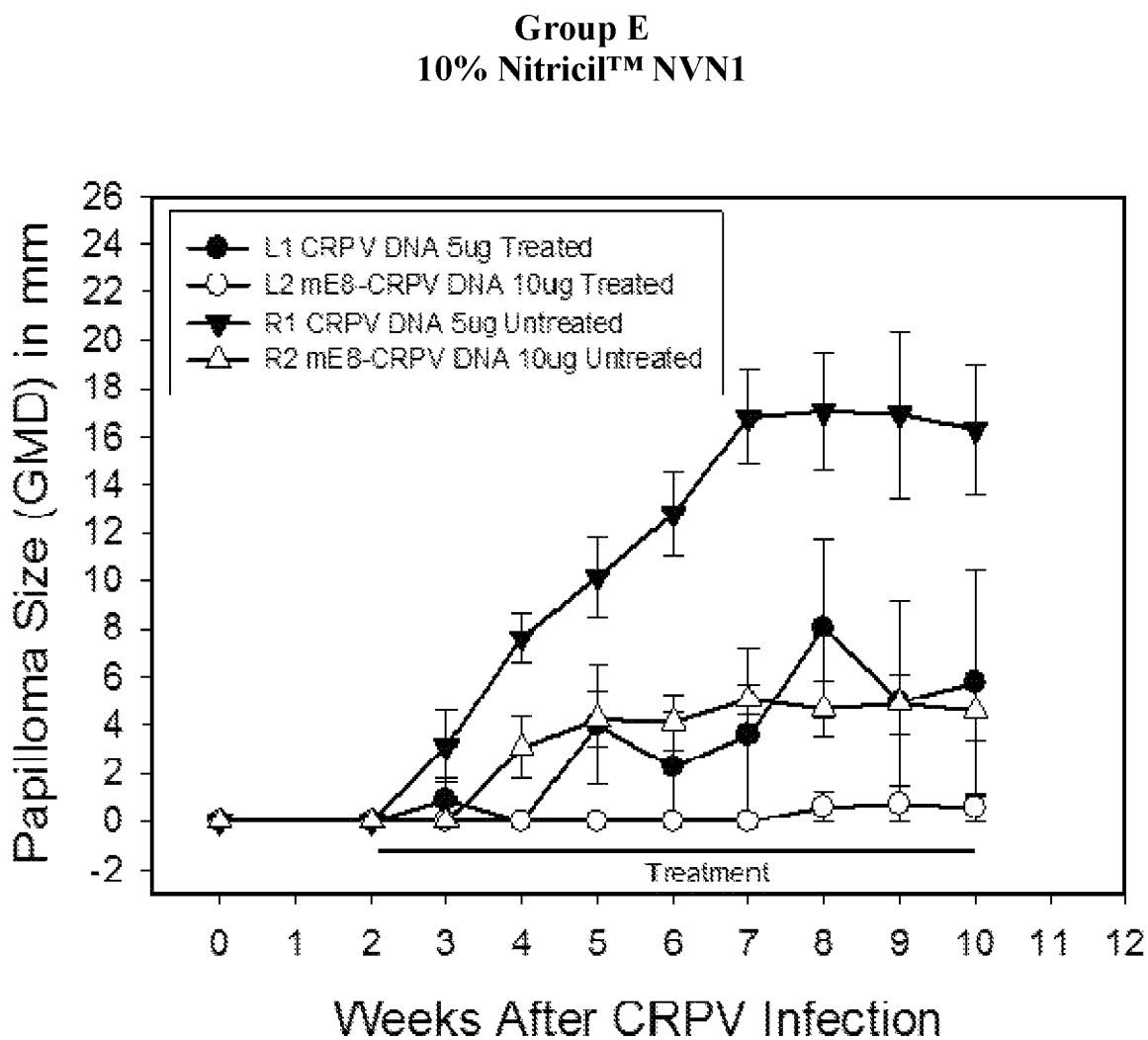
FIG. 22 shows a graph of papilloma size (GMD) in mm over time for the formulation used in Group E. Papillomas were induced at 2 sites with 5 µg of wt-CRPV plasmid stock (●,▼), and at 2 sites with 5 µg mE8-CRPV plasmid stock (○,Δ). Left sites (L1 and L2) were treated topically with the 10% Nitricil™ NVN1 formulation (●,○) and right sites (R1 and R2) were untreated (▼,Δ). Each symbol represents the mean (±SEM) of GMDs of the weekly measurements.
Figure 23:
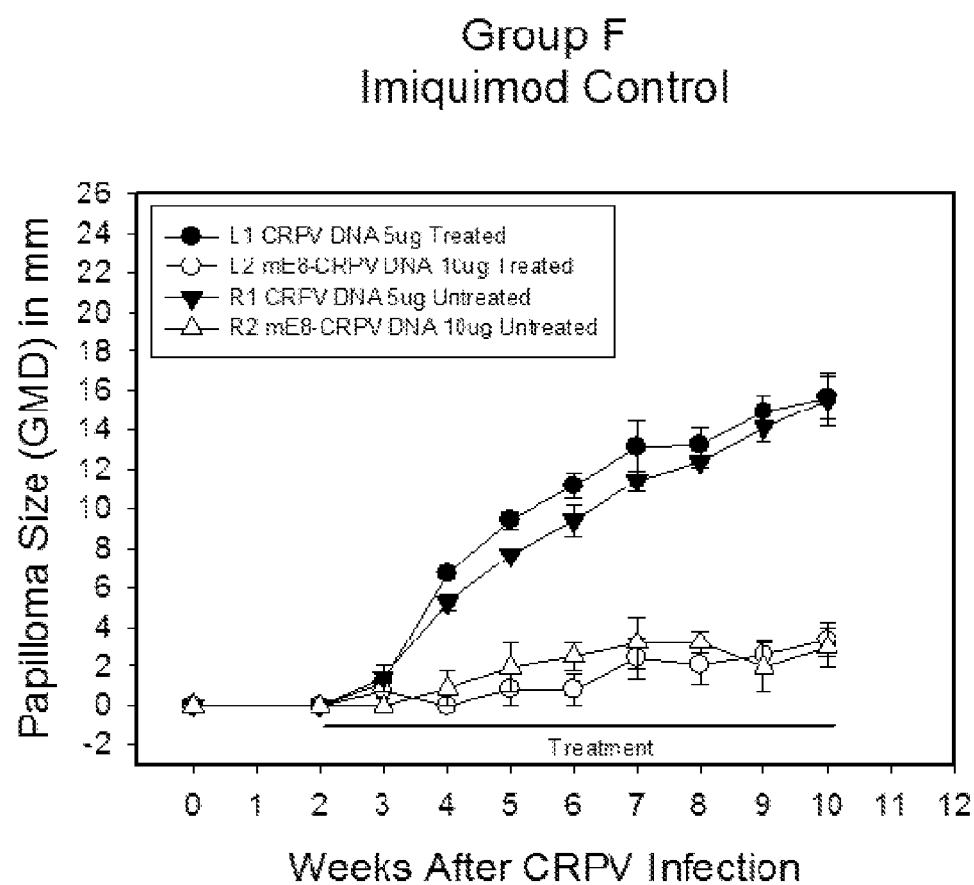
FIG. 23 shows a graph of papilloma size (GMD) in mm over time for the formulation used in Group F. Papillomas were induced at 2 sites with 5 µg of wt-CRPV plasmid stock (●,▼), and at 2 sites with 5 µg mE8-CRPV plasmid stock (○,Δ). Left sites (L1 and L2) were treated topically with the imiquimod control (●,○) and right sites (R1 and R2) were untreated (▼,Δ). Each symbol represents the mean (±SEM) of GMDs of the weekly measurements.

Real time and cumulative NO release profiles are illustrated in FIGS. 11 through 17 as described above. Based on the effectiveness of the formulations for treatment groups D and E against the mutant strains, parameters for real time NO release that may be anti-viral may be identified as illustrated in FIGS. 16A, 16B, and 17. Accordingly, in some embodiments of the present invention, the NO release from an anti-viral composition may fall within one or more of the windows illustrated in FIGS. 16A and/or 17. The NO release within the defined windows may occur at any time point within the anticipated time in which the composition will be applied. Accordingly, the NO release falling within the window may occur within the first 1, 2, or 4 hours or may occur beginning at another time during the application period. The time windows illustrated in FIGS. 16A, 16B, and 17 are shown in Table 6.

TABLE 6

NO release time windows.

| Window | Duration | Min Real Time NO | Max Real Time NO |
|---|---|---|---|
| 0.5 Hour Weighted | 0.5 hours | 25 pmol/mg | 4000 pmol/mg |
| 1 Hour Weighted | 1 hour | 7 pmol/mg | 4000 pmol/mg |
| 2 Hour Weighted | 2 hours | 6 pmol/mg | 4000 pmol/mg |
| 3 Hour Weighted | 4 hours | 5 pmol/mg | 4000 pmol/mg |
| 1 Hour Area | 1 hour | 74.4 nmol/cm$^2$ | 59.52 nmol/cm$^2$ |
| 2 Hour Area | 2 hours | 89.28 nmol/cm$^2$ | 59.52 nmol/cm$^2$ |
| 3 Hour Area | 4 hours | 104.16 nmol/cm$^2$ | 59.52 nmol/cm$^2$ |

Example 4

Groups of rabbits received anti-viral treatments at various doses as described below in Table 7. The formulations for the anti-viral treatments in Groups A-F are provided in Table 8. Each of the formulations for Groups A-E included two separate compositions that were separately stored in a dual chamber pump. Prior to application, the two compositions were dispensed and mixed together in a 1:1 ratio to provide a combined composition that was applied to the rabbit. The target pH for the combined composition was pH 8.

TABLE 7

Anti-viral treatment dosages.

| Group # | No. of rabbits | Anti-viral treatments (beginning on day 14) | Infection with CRPV (2 sites each virus) wt CRPV DNA | mE8-CRPV DNA |
|---|---|---|---|---|
| A | 4 | Placebo | 5 ug | 5 ug |
| B | 4 | 2% Nitricil ™ NVN1 | 5 ug | 5 ug |
| C | 4 | 4% Nitricil ™ NVN1 | 5 ug | 5 ug |
| D | 4 | 8% Nitricil ™ NVN1 | 5 ug | 5 ug |
| E | 4 | 10% Nitricil ™ NVN1 | 5 ug | 5 ug |
| F | 4 | Imiquimod control | 5 ug | 5 ug |

TABLE 8

Formulations for the anti-viral treatments in Groups A-E.

| | % w/w | | | | |
|---|---|---|---|---|---|
| Ingredient | Placebo | 2% Nitricil ™ NVN1 | 4% Nitricil ™ NVN1 | 8% Nitricil ™ NVN1 | 10% Nitricil ™ NVN1 |
| Isopropyl Alcohol | 42.75 | 40.75 | 38.75 | 34.75 | 33.25 |
| Hexylene Glycol | 5.0 | 5.0 | 5.0 | 5.0 | 5.0 |
| Cyclomethicone | 1.25 | 1.25 | 1.25 | 1.25 | 1.25 |
| Hydroxypropyl cellulose | 1.0 | 1.0 | 1.0 | 1.0 | 0.5 |
| Nitricil ™ NVN1 Drug Substance | — | 2.0 | 4.0 | 8.0 | 10.0 |
| Purified Water | 39.65 | 40.65 | 40.65 | 40.65 | 40.65 |
| Glycerin, USP | 5.0 | 2.05 | 2.05 | 2.05 | 2.05 |
| Potassium Phosphate Monobasic | 1.35 | 5.9 | 5.9 | 5.9 | 5.9 |
| Potassium Phosphate Dibasic | 2.6 | — | — | — | — |
| Carboxymethylcellulose Sodium | 1.4 | 1.4 | 1.4 | 1.4 | 1.4 |
| Total | 100.0 | 100.0 | 100.0 | 100.0 | 100.0 |

TABLE 9

NO release data for the formulations of Table 8

| Formulation | Cumulative Release (nmol/mg) | $T_{50}$ of Cumulative Release (minutes) | $C_{max}$, $T_{max}$ (pmol/mg) | Average Release Rate nmol NO/ mg hour$^{0.5}$ | Real Time Release (pmol/mg) |
|---|---|---|---|---|---|
| 2% Nitricil ™ NVN1 | 141.6 (at 2.5 hours) | 3.81 | 398 at 1.8 minutes | 628 over 0.0784 hours | 90.1 at 0.02 hours<br>56.25 at 0.1 hour<br>8.06 at 0.5 hours<br>3.37 at 1 hours<br>1.67 at 2 hours |
| 4% Nitricil ™ NVN1 | 292.7 (at 2.5 hours) | 4.15 | 1148 at 1.2 minutes | 912 over 0.0784 hours | 1147.8 at 0.02 hours<br>239.74 at 0.1 hour<br>18.0 at 0.5 hours<br>3.86 at 1 hours<br>0.56 at 2 hours |
| 8% Nitricil ™ NVN1 | 681.4 (at 4 hours) | 4.25 | 2180 at 1.8 minutes | 2831 over 0.0784 hours | 427.7 at 0.02 hours<br>524.4 at 0.1 hour<br>29.73 at 0.5 hours<br>8.68 at 1 hours<br>1.79 at 2 hours |
| 10% Nitricil ™ NVN1 | 905.2 (at 4 hours) | 3.50 | 2403 at 1.2 minutes | 4516 over 0.0784 hours | 2402 at 0.02 hours<br>736.9 at 0.1 hour<br>414.6 at 0.5 hours<br>33.6 at 1 hours<br>13.8 at 2 hours |

Rabbits were infected with wild-type cottontail rabbit papillomavirus (wt CRPV) and E8-knock-out CRPV (mE8-CRPV) beginning on day 1 for an early therapeutic antiviral treatment study. FIG. 1 shows the outline of experimental infections. The mE8-CRPV was included as this genome generates smaller, slower-growing papillomas that are more clinically similar to human papillomavirus infections.

A total of 24 Adult New Zealand White rabbits (including both genders) were purchased from Robinson, Pa. and used in the experiment. The rabbits were quarantined and cleared (14 days). Each rabbit was inoculated with wt CRPV (at 2 sites; 5 µg/site) and mE8-CRPV viral DNA (at 2 sites; 5 µg/site). CRPV viral DNA was used to generate papillomas and infection was developed via a delayed scarification technique (Cladel N. M., et al., J Virol Methods 2008; 148(1-2):34-39). Of the two sites inoculated with one of the viruses, one site received treatment (i.e., the left site (L1 or L2)) and the other site was untreated (i.e., the right site (R1 or R2)).

The rabbits were placed into one of six groups (Groups A-F). A placebo group (i.e., Group A) served as a control to assess local effects of treatment in treated Groups B-E.

Treatments for Groups A-F began at week two at a time when the papillomas were not yet visible. This time point allowed for effects on subclinical papillomas to be assessed. Treatment was 5× weekly (Monday-Friday), for five weeks with a dose of 0.1 ml per approximately 2.5 cm×2.5 cm site for topical treatments. Body weights were taken weekly, and blood sera were collected at the end of the treatment period for blood chemistries, as needed.

The frequency and size of papillomas was measured weekly in 3 axes (length×width×height) in mm. Data was entered into a spread sheet and calculations were conducted of the geometric mean diameter of each papilloma, mean±SEM for each group, Student's t-test between each paired groups and plots made of papilloma size vs time. Plots of weight changes were also conducted.

At termination, kidney and liver samples were retrieved for histology and toxicity assessment, as needed. Skin/papilloma sites were monitored photographically and biopsies assessed for histology at experiment/treatment termination.

FIGS. 18-23 show graphs of papilloma size (GMD) in mm over time for the formulations in Groups A-F, respectively.

In light of the dosing regimen of 5 days per week and once daily, doses that show only minimal efficacy could be suitable for use with a different dosing schedule, e.g., twice daily 7 days per week. Based on the effectiveness of the formulations for treatment Groups D and E against the mutant strains, parameters for real time NO release may fall within one or more of the windows illustrated in FIGS. 16A and/or 17. However, other doses may also be effective based on treatment Groups B and C as the duration of NO release for these groups may allow for more frequent dosing. Accordingly, a product (e.g., a topical composition) with an NO release falling within a 30 minute window defined as measured based on weight and having a minimum instantaneous release of 7 pmol/mg and a maximum instantaneous release of 4,000 pmol/mg may be suitable. In some embodiments, a product with an NO release falling within a 30 minute window defined as measured based on weight and having a minimum instantaneous release of 15 pmol/mg and a maximum instantaneous release of 4,000 pmol/mg may be suitable. The NO release within the defined windows may occur at any time point within the anticipated time in which the product will be applied and/or present on the skin of a subject. Accordingly, an NO release falling within one or more of the windows illustrated in FIGS. 16A and/or 17 may occur within the first 1, 2, or 4 hours after application/administration or may occur beginning at another time after application/administration.

Example 5

Tissue samples from New Zealand white rabbits infected with Cottontail Rabbit Papillomavirus and treated as described in Example 4 were obtained at the end of treatment. The skin sections were processed to hematoxylin and eosin (H & E) slides and submitted for microscopic evaluation in a blinded fashion. After evaluating the slides, the results were summarized into three main categories: 1) papilloma, 2) hyperplasia of marked intensity, and 3) hyperplasia of minimal to mild intensity. The presence of inflammatory cells was determined qualitatively. No quantitative analysis was performed. However, the qualitative assessment revealed a similar level of inflammation amongst the three categories, which was that inflammation was generally low and comparable. Table 10 provides the histology results from the H&E staining.

TABLE 10

H&E Histology Results.

| Category | Histopathological Findings |
| --- | --- |
| #1- Papilloma | Extensive exophytic proliferation of squamous epithelium which is well differentiated. |
| | Finger-like papillary projections that protrude over the surface of the epidermis covered by layers of keratin mixed with serocellular material. |
| | High levels of intra-nuclear dark to light basophilic viral inclusions |
| | Diffuse infiltration of minimal to mild numbers of inflammatory cells that include in decreasing order: lymphocytes, plasma cells, and heterophils with rare macrophages. |
| #2- Hyperplasia of marked intensity | Combination of exophytic and endophytic proliferation of squamous epithelium which is well differentiated. |
| | Papillary projections either protrude or invade within the dermis and are covered by moderate to marked degrees of keratin that are rarely mixed with serocellular material. |
| | Present within the squamous epithelium are questionable intra-nuclear dark to light basophilic viral inclusions. However, the density of these inclusions is clearly fall less than the papillomas of Category #1 |
| | Mainly in the superficial dermis a more or less diffuse infiltration of mild numbers of inflammatory cells that include in decreasing order: lymphocytes, plasma cells, and heterophils with rare macrophages. |
| #3- Hyperplasia of minimal to mild intensity | Predominately endophytic proliferation of squamous epithelium which is well differentiated. |
| | Papillary projections invade the dermis with a minimal amount of keratin covering the eipidermis. |
| | Intranuclear dark to light basophilic viral inclusion are not observed. |
| | Mainly in the superficial dermis a more or less diffuse infiltration of mild numbers of inflammatory cells that include in decreasing order: lymphocytes, plasma cells, and heterophils with rare macrophages. |

The tissues slides assigned to Category #3 (Hyperplasia of minimal to mild intensity) include the tissue samples obtained from animals treated with either 8% Nitricil™ NVN1 or 10% Nitricil™ NVN1. Intra-nuclear dark to light basophilic viral inclusions were not observed in the tissue slides assigned to Category #3, which suggests that treatment with high concentrations of Nitricil™ NVN1, such as, for example, with the 8% or 10% Nitricil™ NVN1 formulations, suppresses and/or inhibits viral replication of a virus without altering the local infiltration of inflammatory immune cells.

Example 6

Additional formulations were prepared and used to determine efficacy in treating and/or preventing virus-related cutaneous conditions, such as, for example, genital warts. These formulations included Nitricil™ NVN1 in an amount of 4%, 8%, 12%, or 16% along with a placebo. Each of the formulations included a hydrogel having a pH of 4.5 and a composition as provided in Table 11, and a second composition in the form of a gel and having a composition as provided in Table 12. Upon admixing the hydrogel and gel, a combined composition was achieved having a composition as provided in Table 13.

TABLE 11

Composition of the pH 4.5 Hydrogel

| Component | % w/w |
|---|---|
| Water, Purified, USP | 64.90 |
| Potassium Phosphate Monobasic, NF | 11.50 |
| Alcohol, USP | 10.00 |
| Glycerin, USP | 8.00 |
| Cyclomethicone, NF | 3.00 |
| Carboxymethylcellulose Sodium, NF | 2.50 |
| Benzoic Acid, USP | 0.10 |
| Total | 100.00 |

TABLE 12

Composition of the Gel

| Component | Placebo % w/w | 8% | 16% | 24% | 32% |
|---|---|---|---|---|---|
| Isopropyl Alcohol, USP | 85.45 | 78.50 | 70.50 | 62.75 | 54.75 |
| Hexylene Glycol, NF | 10.00 | 10.00 | 10.00 | 10.00 | 10.00 |
| Cyclomethicone, NF | 2.50 | 2.50 | 2.50 | 2.50 | 2.50 |
| Hydroxypropyl cellulose, NF | 2.00 | 1.00 | 1.00 | 0.75 | 0.75 |
| Nitricil™ NVN1 | — | 8.00 | 16.00 | 24.00 | 32.00 |
| Titanium Dioxide, USP | 0.05 | — | — | — | — |
| Total | 100.00 | 100.00 | 100.00 | 100.00 | 100.00 |

TABLE 13

Composition of the combined composition

| Component | Placebo % w/w | 4% | 8% | 12% | 16% |
|---|---|---|---|---|---|
| Isopropyl Alcohol, USP | 42.725 | 39.25 | 35.25 | 31.375 | 27.375 |
| Water, Purified, USP | 32.45 | 32.45 | 32.45 | 32.45 | 32.45 |
| Potassium Phosphate Monobasic, NF | 5.75 | 5.75 | 5.75 | 5.75 | 5.75 |
| Hexylene Glycol, NF | 5.00 | 5.00 | 5.00 | 5.00 | 5.00 |
| Alcohol (95% Ethanol), USP | 5.00 | 5.00 | 5.00 | 5.00 | 5.00 |
| Nitricil™ NVN1 | — | 4.00 | 8.00 | 12.00 | 16.00 |
| Glycerin, USP | 4.00 | 4.00 | 4.00 | 4.00 | 4.00 |
| Cyclomethicone, NF | 2.75 | 2.75 | 2.75 | 2.75 | 2.75 |
| Carboxymethylcellulose Sodium, NF | 1.25 | 1.25 | 1.25 | 1.25 | 1.25 |
| Hydroxypropyl Cellulose, NF | 1.00 | 0.50 | 0.50 | 0.375 | 0.375 |
| Benzoic Acid, USP | 0.05 | 0.05 | 0.05 | 0.05 | 0.05 |
| Titanium Dioxide, USP | 0.025 | — | — | — | — |
| Total | 100.00 | 100.00 | 100.00 | 100.00 | 100.00 |

Example 7

Primary human keratinocytes were seeded on to a dermal equivalent and kept submerged in culture media for 2 days in order to establish cell monolayers. After 2 days this entire assembly was lifted to the air:liquid surface, which corresponds to Day 0. On days 7-12, topical application of 400 μL of Nitricil™ NVN1 or Nitricil™ NVN4 (in 50 mM PBS) was applied to the upper surface of the raft culture and incubated for 1 hr. Following 1 hr incubation, the solution was gently aspirated from the surface of the raft cultures and the raft culture media was replenished.

Cultures were harvested on Day 13. Twelve hrs prior to harvest, cultures were incubated with 100 μL/mL BrdU as a biomarker for cellular DNA synthesis. Cultures were formalin-fixed and paraffin-embedded. Four μm sections were cut and stained with H&E. Adjacent sections were probed with BrdU antibodies to determine the patterns and intensity of host DNA replication.

Figures 24A, 24B, 24C:
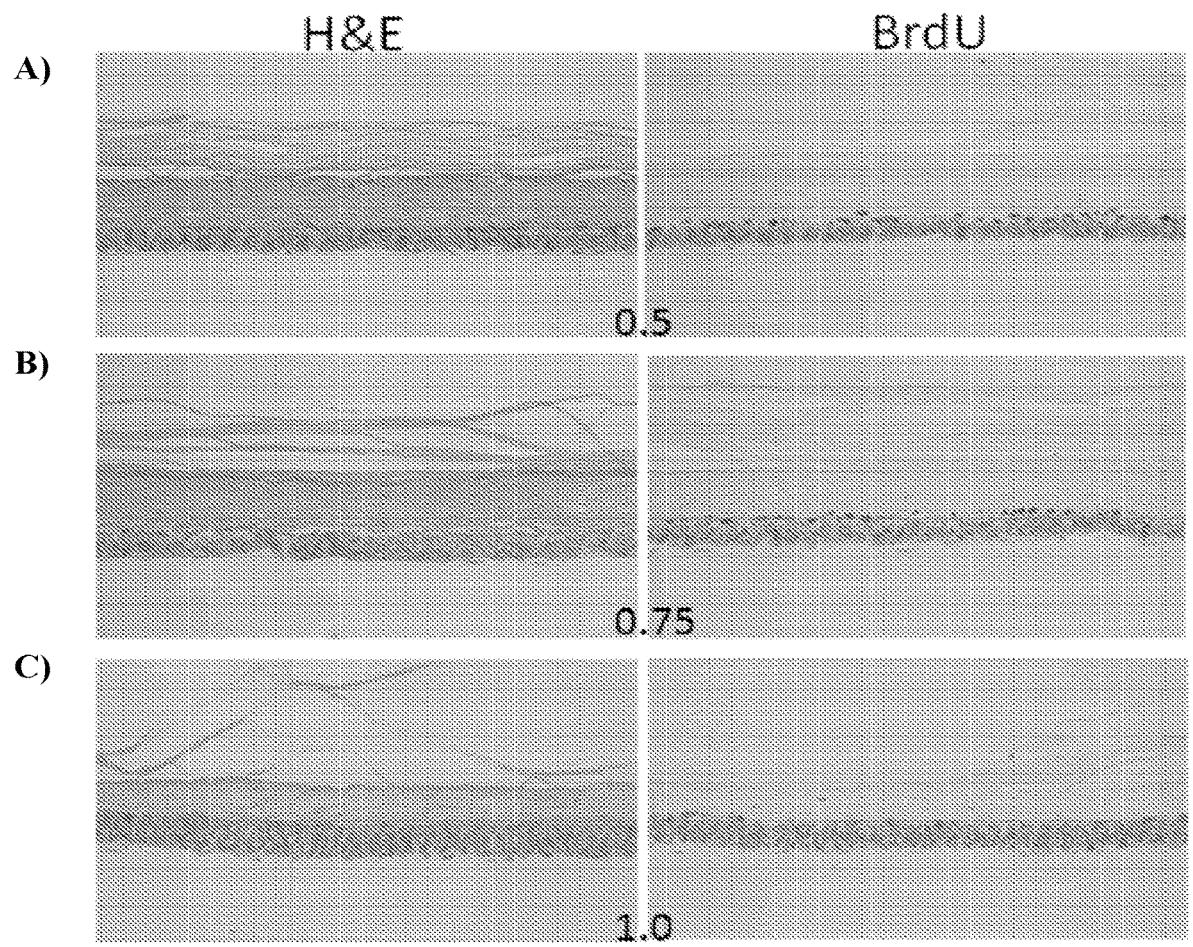
FIGS. 24A-24C illustrate representative images of uninfected raft cultures that were treated with 0.5, 0.75, and 1.0 mg/mL of Nitricil™ NVN1, respectively, and are stained with H&E or labeled with BrdU antibodies.
Figures 25A, 25B, 25C:
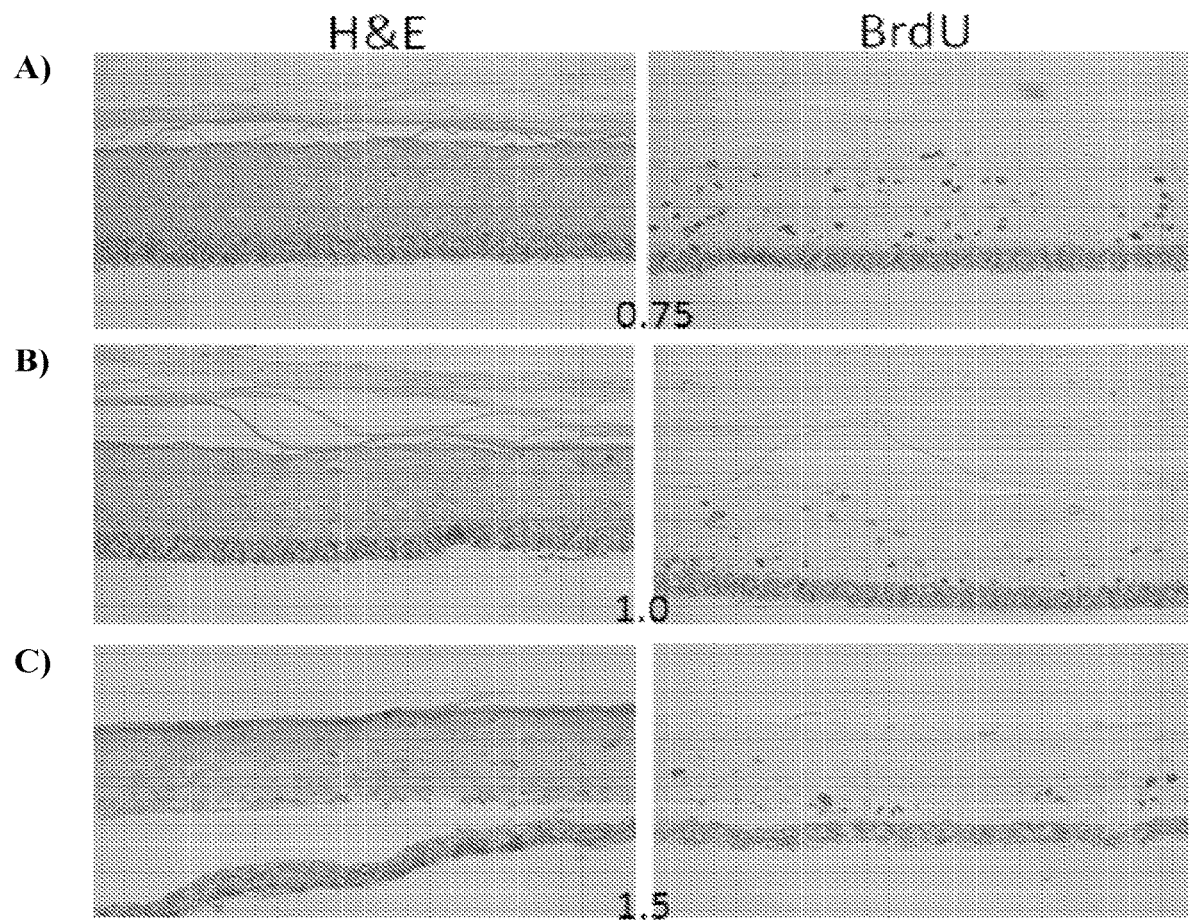
FIGS. 25A-25C illustrate representative images of HPV-18 infected cultures that were treated with 0.75, 1.0, and 1.5 mg/mL of Nitricil™ NVN1, respectively, and are stained with H&E or labeled with BrdU antibodies.
Figures 26A, 26B, 26C, 26D:
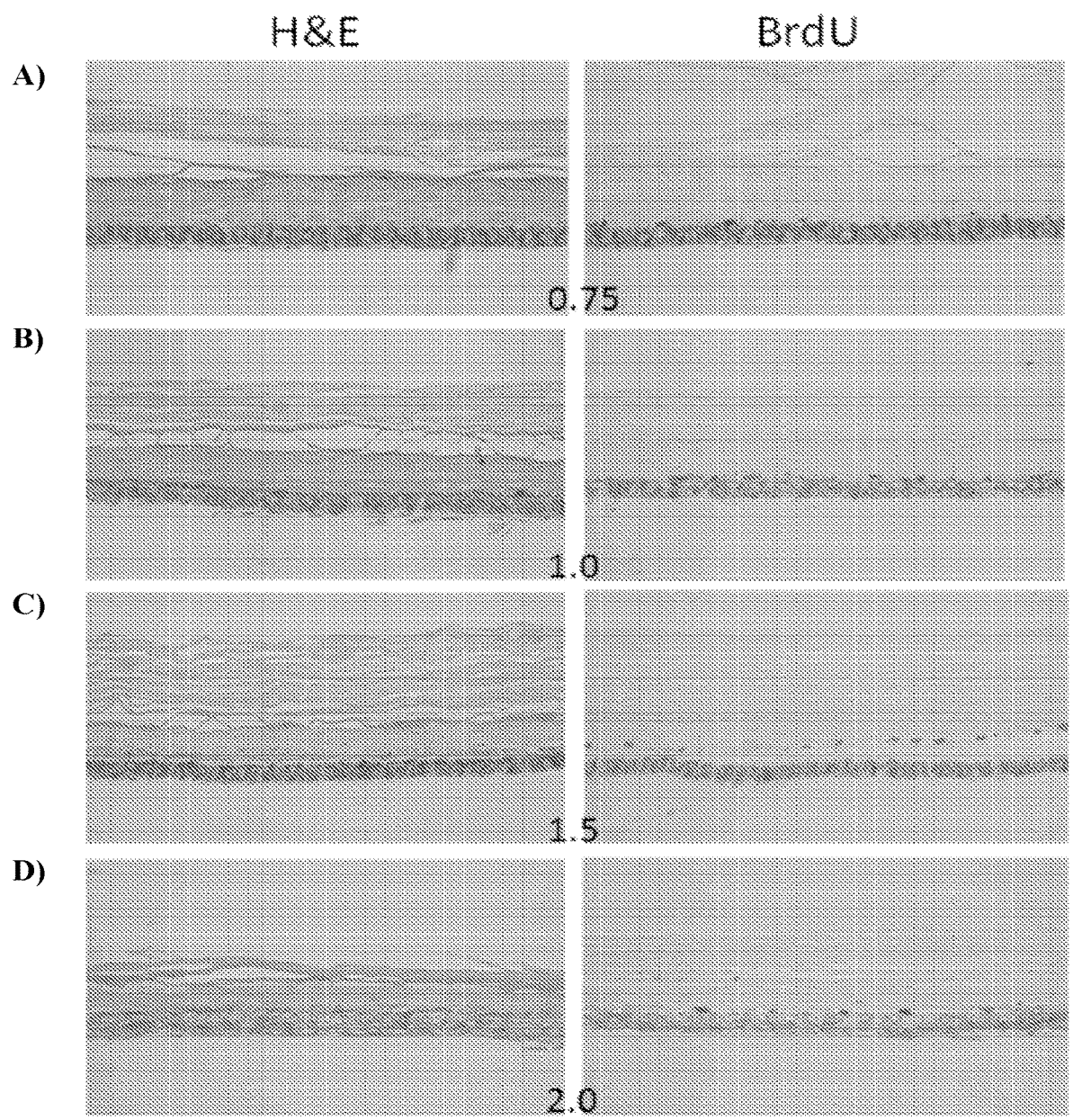
FIGS. 26A-26D illustrate representative images of uninfected raft cultures that were treated with 0.75, 1.0, 1.5, and 2.0 mg/mL of Nitricil™ NVN4, respectively, and are stained with H&E or labeled with BrdU antibodies.
Figures 27A, 27B, 27C, 27D:
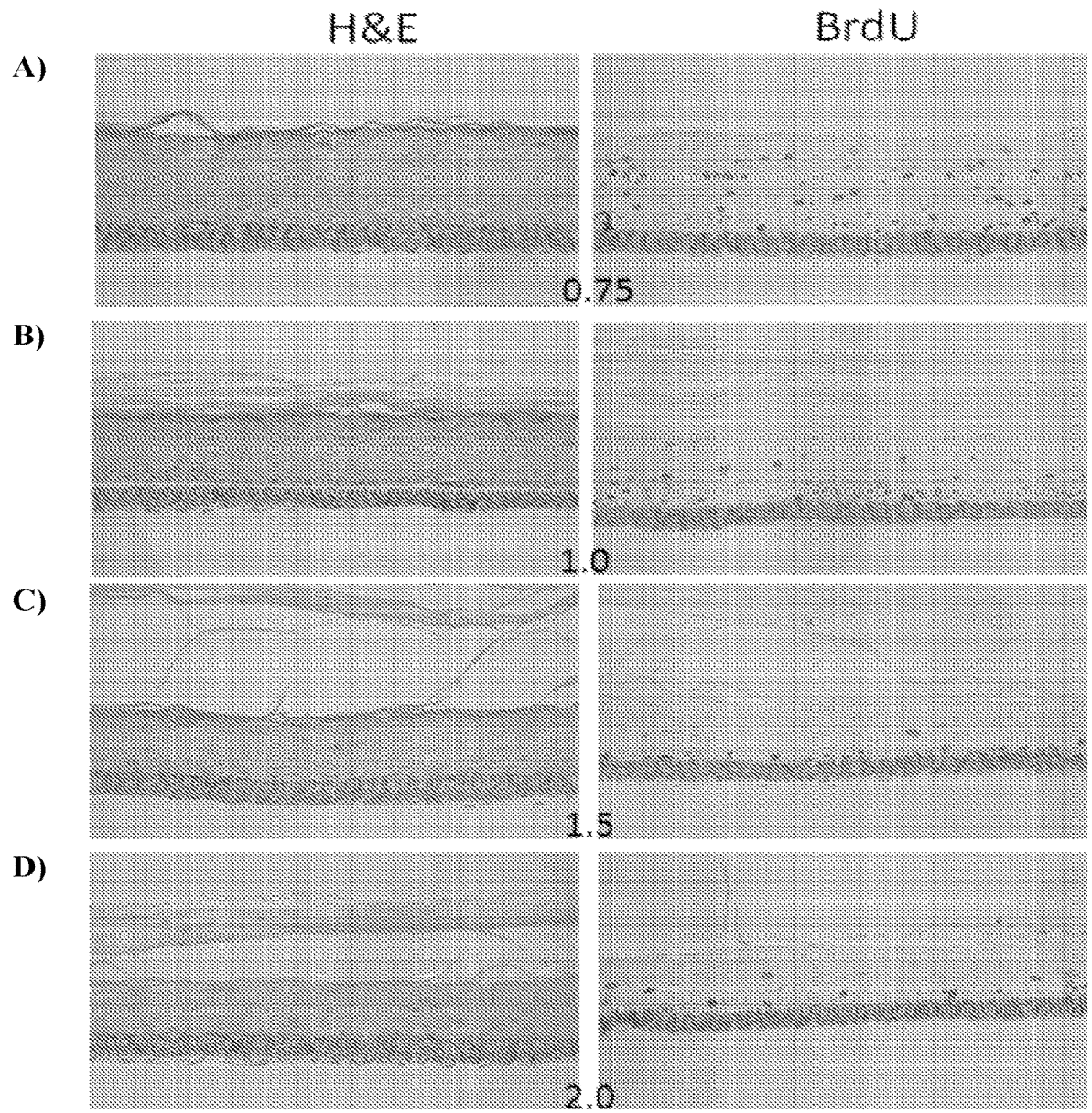
FIGS. 27A-27D illustrate representative images of HPV-18 infected cultures that were treated with 0.75, 1.0, 1.5, and 2.0 mg/mL of Nitricil™ NVN4, respectively, and are stained with H&E or labeled with BrdU antibodies.

Representative images of uninfected raft cultures treated with Nitricil™ NVN1 and HPV-18 infected raft cultures treated with Nitricil™ NVN1 are provided in FIGS. 24A-24C and 25A-25C, respectively. FIGS. 24A-24C illustrate uninfected cultures that were treated with 0.5, 0.75, and 1.0 mg/mL of Nitricil™ NVN1, respectively, and are stained with H&E or labeled with BrdU antibodies. FIGS. 25A-25C illustrate HPV-18 infected cultures that were treated with 0.75, 1.0, and 1.5 mg/mL of Nitricil™ NVN1, respectively, and are stained with H&E or labeled with BrdU antibodies. The amount of HPV-18 viral replication in raft cultures treated with Nitricil™ NVN1 is provided in Table 14.

TABLE 14

HPV-18 viral copy number in raft cultures treated with Nitricil™ NVN1.

| Treatment | % HPV-18 Copy Number* |
|---|---|
| 50 mM PBS | 100.00 |
| 0.75 mg/mL Nitricil™ NVN1 | 75.0 |
| 1.0 mg/mL Nitricil™ NVN1 | 38.3 |
| 1.5 mg/mL Nitricil™ NVN1 | 14.95 |
| Uninfected Raft Culture | 0.02 |

*Percent HPV-18 Copy Number compared to cultures treated with 50 mM PBS.

Representative images of uninfected raft cultures treated with Nitricil™ NVN4 and HPV-18 infected raft cultures treated with Nitricil™ NVN4 are provided in FIGS. 26A-26D and 27A-27D, respectively. FIGS. 26A-26D illustrate uninfected cultures that were treated with 0.75, 1.0, 1.5, and 2.0 mg/mL of Nitricil™ NVN4, respectively, and are stained with H&E or labeled with BrdU antibodies. FIGS. 27A-27D illustrate HPV-18 infected cultures that were treated with 0.75, 1.0, 1.5, and 2.0 mg/mL of Nitricil™ NVN4, respectively, and are stained with H&E or labeled with BrdU antibodies. The amount of HPV-18 viral replication in raft cultures treated with Nitricil™ NVN4 is provided in Table 15.

TABLE 15

HPV-18 viral copy number in raft cultures treated with Nitricil™ NVN4.

| Treatment | % HPV-18 Copy Number* |
|---|---|
| 50 mM PBS | 100.00 |
| 0.75 mg/mL Nitricil™ NVN4 | 63.1 |
| 1.0 mg/mL Nitricil™ NVN4 | 47.3 |
| 1.5 mg/mL Nitricil™ NVN4 | 29.3 |
| 2.0 mg/mL Nitricil™ NVN4 | 14.8 |
| Uninfected Raft Culture | 0.02 |

*Percent HPV-18 Copy Number compared to cultures treated with 50 mM PBS.

The efficacy of topical nitric oxide-releasing candidates to inhibit viral replication was determined in vitro utilizing organotypic cultures of primary human keratinocytes containing HPV-18 genomic replicons. The results following 1 hr per day topical application of drug substance for six days demonstrated a dose responsive reduction in viral DNA copy number as determined by qPCR. This data supports a direct effect of nitric oxide-releasing drug candidates on viral replication at concentrations (1.5 or 2.0 mg/mL) that are not cytotoxic to host cells and suggests that nitric oxide has a preferential deleterious effect on viral replication.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A method of treating and/or preventing a viral infection in a subject in need thereof comprising:
    administering a topical composition to the skin of a subject,
    wherein the topical composition comprises a nitric oxide (NO)-releasing active pharmaceutical ingredient in an amount of about 0.5% to about 25% by weight of the topical composition and the NO-releasing active pharmaceutical ingredient is a NO-releasing compound comprising an NO donor selected from the group consisting of a diazeniumdiolate, nitrosothiol, nitrosamine, hydroxyl nitrosamine, hydroxyl amine and hydroxyurea; and
    wherein the topical composition has a $C_{max}$ of greater than 160 pmol of NO/mg, as measured by in vitro release testing, thereby treating and/or preventing the viral infection in the subject.

2. The method of claim 1, wherein the topical composition has a $C_{max}$ of greater than 175 pmol of NO/mg, as measured by in vitro release testing.

3. The method of claim 1, wherein the topical composition has a $C_{max}$ of greater than 200 pmol of NO/mg, as measured by in vitro release testing.

4. The method of claim 1, wherein the topical composition has a $C_{max}$ of greater than 160 pmol to about 3500 pmol of NO/mg, as measured by in vitro release testing.

5. The method of claim 1, wherein the topical composition releases nitric oxide in an amount of about 0.05% to about 10% by weight of the topical composition, as measured by real time in vitro release testing.

6. The method of claim 1, wherein the topical composition releases nitric oxide in a cumulative amount of about 10 nmol of NO/mg of the topical composition to 1000 nmol of NO/mg of the topical composition in a time period of 1 hour after administration of the topical composition to the skin of the subject, as measured by real time in vitro release testing.

7. The method of claim 1, wherein the topical composition releases nitric oxide in a cumulative amount of about 90 nmol of NO/mg of the topical composition to 450 nmol of NO/mg of the topical composition in a time period of 4 hours after administration of the topical composition to the skin of the subject, as measured by real time in vitro release testing.

8. The method of any one of claim 1, wherein the topical composition releases nitric oxide in a cumulative amount of about 180 nmol of NO/mg of the topical composition to 1000 nmol of NO/mg of the topical composition in a time period of 24 hours after administration of the topical composition to the skin of the subject, as measured by real time in vitro release testing.

9. The method of claim 1, wherein the topical composition provides a continuous release of nitric oxide for at least about 5 hours after administration of the topical composition to the skin of the subject, as measured by real time in vitro release testing.

10. The method of claim 9, wherein, during the continuous release of nitric oxide, the topical composition has a release of NO that, on average, is in a range of about 1 to about 500 pmol of NO/mg of the composition, as measured by real time in vitro release testing.

11. The method of claim 1, wherein the nitric oxide-releasing active pharmaceutical ingredient releases nitric oxide in an amount of at least about 50% in about 9 minutes or more after administration of the topical composition to the skin of the subject, based on a total NO release determined at 24 hours after administration and measured by real time in vitro release testing.

12. The method of claim 1, wherein the nitric oxide-releasing active pharmaceutical ingredient comprises a co-condensed silica network comprising diazeniumdiolated methylaminopropyl trimethoxysilane (MAP3) and tetra methyl orthosilicate (TMOS) and/or diazeniumdiolated methylaminopropyl trimethoxysilane (MAP3) and tetraethyl orthosilicate (TEOS).

13. A method of treating and/or preventing molluscum contagiosum in a subject in need thereof comprising:
    administering a topical composition to the skin of a subject,
    wherein the topical composition comprises a nitric oxide (NO)-releasing active pharmaceutical ingredient in an amount of about 0.5% to about 25% by weight of the topical composition and the NO-releasing active pharmaceutical ingredient is a NO-releasing compound comprising an NO donor selected from the group consisting of a diazeniumdiolate, nitrosothiol, nitrosamine, hydroxyl nitrosamine, hydroxyl amine and hydroxyurea; and
    wherein the topical composition has a $C_{max}$ of greater than 160 pmol of NO/mg, as measured by in vitro release testing, thereby treating and/or preventing molluscum contagiosum in the subject.

14. A method of reducing the appearance and/or size of a lesion on a subject in need thereof comprising:
    administering a topical composition to the lesion on the subject,
    wherein the topical composition comprises a nitric oxide (NO)-releasing active pharmaceutical ingredient in an amount of about 0.5% to about 25% by weight of the topical composition and the NO-releasing active pharmaceutical ingredient is a NO-releasing compound comprising an NO donor selected from the group consisting of a diazeniumdiolate, nitrosothiol, nitrosamine, hydroxyl nitrosamine, hydroxyl amine and hydroxyurea; and
    wherein the topical composition has a $C_{max}$ of greater than 160 pmol of NO/mg, as measured by in vitro release testing, thereby reducing the appearance and/or size of the lesion on the subject.

15. The method of claim 14, wherein the lesion is caused by cytomegalovirus (CMV), epstein-barr virus, varicella zoster virus (VZV), vaccinia virus, cowpox virus, monkeypox virus, herpes simplex virus (HSV), herpes zoster, human herpes virus 6 (HHV-6), human herpes virus 8 (HHV-8), papillomavirus, molluscum contagiosum, orf, variola, and/or coxsackie virus.

16. The method of claim 15, wherein the lesion is caused by a papillomavirus.

17. The method of claim 15, wherein the lesion is caused by herpes simplex type 1 and/or herpes simplex type 2.

18. The method of claim 15, wherein the lesion is caused by molluscum contagiosum.

19. The method of claim 14, wherein the lesion is a benign lesion.

20. The method of claim 14, wherein the lesion is a malignant lesion.

\* \* \* \* \*

UNITED STATES PATENT AND TRADEMARK OFFICE
CERTIFICATE OF CORRECTION

Page 1 of 1

PATENT NO. : 10,736,839 B2
APPLICATION NO. : 16/431214
DATED : August 11, 2020
INVENTOR(S) : McHale et al.

It is certified that error appears in the above-identified patent and that said Letters Patent is hereby corrected as shown below:

In the Specification

Column 13, Line 62: Please correct "100 m" to read -- 100 μm --

Column 24, Line 61: Please correct "10%0" to read -- 10% --

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*